US011529390B2

(12) United States Patent
Poirier et al.

(10) Patent No.: US 11,529,390 B2
(45) Date of Patent: Dec. 20, 2022

(54) PCSK9 INHIBITORY POLYPOLYPEPTIDES AND METHODS OF USE

(71) Applicant: INSTITUT DE CARDIOLOGIE DE MONTREAL, Montreal (CA)

(72) Inventors: Steve Poirier, Outremont (CA); Gaetan Mayer, Montreal (CA)

(73) Assignee: INSTITUT DE CARDIOLOGIE DE MONTREAL, Montreal (CA)

(*) Notice: Subject to any disclaimer, the term of this patent is extended or adjusted under 35 U.S.C. 154(b) by 50 days.

(21) Appl. No.: 17/095,992

(22) Filed: Nov. 12, 2020

(65) Prior Publication Data

US 2021/0162000 A1 Jun. 3, 2021

Related U.S. Application Data

(63) Continuation-in-part of application No. 15/558,013, filed as application No. PCT/IB2016/051559 on Mar. 19, 2016, now abandoned.

(60) Provisional application No. 62/135,668, filed on Mar. 19, 2015, provisional application No. 62/259,621, filed on Nov. 24, 2015.

(51) Int. Cl.

*A61K 38/16* (2006.01)
*A61K 47/69* (2017.01)

(52) U.S. Cl.

CPC .......... *A61K 38/16* (2013.01); *A61K 47/6937* (2017.08)

(58) Field of Classification Search

None

See application file for complete search history.

(56) References Cited

U.S. PATENT DOCUMENTS

| | | | | |
|---|---|---|---|---|
| 7,572,771 B1 * | 8/2009 | Remaley | C07K 14/775 514/1.1 | |
| 2005/0221395 A1 * | 10/2005 | Zabrecky | A61K 31/19 435/7.9 | |

OTHER PUBLICATIONS

Wu et al. "The molecular chaperone gp96/GRP94 interacts with Toll-like receptors and integrins via its C-terminal hydrophobic domain" J. Biol. Chem., Feb. 24, 2012, 287(9):6735-42.*

Poirier et al. GRP94 Regulates Circulating Cholesterol Levels through Blockade of PCSK9-Induced LDLR Degradation. Cell Reports vol. 13, Issue 10, Dec. 15, 2015, pp. 2064-2071.*

Abifadel, M., Rabes, J.P., Devillers, M., Munnich, A., Erlich, D., Junien, C., Varret, M., and Boileau, C. Mutations and polymorphisms in the proprotein convertase subtilisin kexin 9 (PCSK9) gene in cholesterol metabolism and disease. Hum. Mutat. Apr. 2009; 520-529, 30(4). Wiley, USA.

Abifadel, M., Varret, M., Rabes, J.P., Allard, D., Ouguerram, K., Devillers, M., Cruaud, C., Benjannet, S., Wickham, L., Erlich, D., et al. Mutations in PCSK9 cause autosomal dominant hypercholesterolemia. Nat. Genet. Jun. 2003; 154-156, 34(2). Nature Publishing, UK.

Aimiuwu, J., Wang, H., Chen, P., Xie, Z., Wang, J., Liu, S., Klisovic, R., Mims, A., Blum, W., Marcucci, G., et al. RNA-dependent inhibition of ribonucleotide reductase is a major pathway for 5-azacytidine activity in acute myeloid leukemia. Blood May 31, 2012; 5229-5238, 119(22). American Society of Hematology, USA.

Baigent, C., Blackwell, L., Emberson, J., Holland, L.E., Reith, C., Bhala, N., Peto, R., Barnes, E.H., Keech, A., Simes, J., et al. Efficacy and safety of more intensive lowering of LDL cholesterol: a meta-analysis of data from 170,000 participants in 26 randomised trials. Lancet Nov. 13, 2010; 1670-1681, 376(9753). Elsevier, USA.

Benjannet, S., Rhainds, D., Essalmani, R., Mayne, J., Wickham, L., Jin, W., Asselin, M.C., Hamelin, J., Varret, M., Allard, D., et al. NARC-1/PCSK9 and its natural mutants: zymogen cleavage and effects on the low density lipoprotein (LDL) receptor and LDL cholesterol. J. Biol. Chem. Nov. 19, 2004; 48865-48875, 279(47). American Society for Biochemistry and Molecular Biology, USA.

Benjannet, S., Rhainds, D., Hamelin, J., Nassoury, N., and Seidah, N.G. The proprotein convertase (PC) PCSK9 is inactivated by furin and/or PC5/6A: functional consequences of natural mutations and post-translational modifications. J. Biol. Chem. Oct. 13, 2006; 30561-30572, 281(41). American Society for Biochemistry and Molecular Biology, USA.

Berge, K.E., Ose, L., and Leren, T.P. Missense mutations in the PCSK9 gene are associated with hypocholesterolemia and possibly increased response to statin therapy. Arterioscler. Thromb. Vasc. Biol. May 2006; 1094-1100, 26(5). Lippincott, USA.

Brown, M.S., and Goldstein, J.L. A receptor-mediated pathway for cholesterol homeostasis. Science Apr. 4, 1986; 34-47, 232(4746). American Association for the Advancement of Science, USA.

Bruckert, E., Hayem, G., Dejager, S., Yau, C., and Begaud, B. Mild to moderate muscular symptoms with high-dosage statin therapy in hyperlipidemic patients—the PRIMO study. Cardiovasc. Drugs Ther. Dec. 2005; 403-414, 19(6). Springer, USA.

Chen, W.T., Tseng, C.C., Pfaffenbach, K., Kanel, G., Luo, B., Stiles, B.L., and Lee, A.S. Liver-specific knockout of GRP94 in mice disrupts cell adhesion, activates liver progenitor cells, and accelerates liver tumorigenesis. Hepatology Mar. 2014; 947-957, 59(3). Wiley, USA.

Cloutier, P., Al-Khoury, R., Lavallee-Adam, M., Faubert, D., Jiang, H., Poitras, C., Bouchard, A., Forget, D., Blanchette, M., and Coulombe, B. High-resolution mapping of the protein interaction network for the human transcription machinery and affinity purification of RNA polymerase II-associated complexes. Methods Aug. 2009; 381-386, 48(4). Elsevier, USA.

(Continued)

*Primary Examiner* — Maury A Audet

(57) ABSTRACT

The present invention relates to PCSK9 inhibitors and methods of use thereof. Specifically, the invention relates to PCSK9 cell-based assay, PCSK9 inhibiting polypeptides and derivatives thereof. The invention includes pharmaceutical compositions comprising a PCSK9 inhibitor polypeptide together with a pharmaceutically acceptable carrier and method for treating cardiovascular disorders, hyperlipidemia, inflammatory diseases or inflammatory response to infection.

13 Claims, 15 Drawing Sheets

Specification includes a Sequence Listing.

(56) References Cited

OTHER PUBLICATIONS

Cohen, J., Pertsemlidis, A., Kotowski, I.K., Graham, R., Garcia, C.K., and Hobbs, H.H. Low LDL cholesterol in individuals of African descent resulting from frequent nonsense mutations in PCSK9. Nat. Genet. Feb. 2005; 161-165, 37(2). Nature Publishing, UK.

Cohen, J.C., Boerwinkle, E., Mosley, T.H., Jr., and Hobbs, H.H. Sequence variations in PCSK9, low LDL, and protection against coronary heart disease. N. Engl. J. Med. Mar. 23, 2006; 1264-1272, 354(12). Massachusetts Medical Society, USA.

Cunningham, D., Danley, D.E., Geoghegan, K.F., Griffor, M.C., Hawkins, J.L., Subashi, T.A., Varghese, A.H., Ammirati, M.J., Culp, J.S., Hoth, L.R., et al. Structural and biophysical studies of PCSK9 and its mutants linked to familial hypercholesterolemia. Nat Struct Mol Biol. May 2007; 413-419, 14(5). Nature Publishing, UK.

Dollins, D.E., Warren, J.J., Immormino, R.M., and Gewirth, D.T. Structures of GRP94-nucleotide complexes reveal mechanistic differences between the hsp90 chaperones. Mol. Cell Oct. 12, 2007; 41-56, 28(1). Cell Press, Elsevier, USA.

Dubuc, G., Chamberland, A., Wassef, H., Davignon, J., Seidah, N.G., Bernier, L., and Prat, A. Statins upregulate PCSK9, the gene encoding the proprotein convertase neural apoptosis-regulated convertase-1 implicated in familial hypercholesterolemia. Arterioscler. Thromb. Vasc. Biol. Aug. 2004; 1454-1459, 24(8). Lippincott, USA.

Goldstein, J.L., and Brown, M.S. Regulation of low-density lipoprotein receptors: implications for pathogenesis and therapy of hypercholesterolemia and atherosclerosis. Circulation Sep. 1987; 504-507, 76(3). Lippincott, USA.

Heidenreich, P.A., Trogdon, J.G., Khavjou, O.A., Butler, J., Dracup, K., Ezekowitz, M.D., Finkelstein, E.A., Hong, Y., Johnston, S.C., Khera, A., et al. Forecasting the future of cardiovascular disease in the United States: a policy statement from the American Heart Association. Circulation Mar. 1, 2011; 933-944, 123(8). Lippincott, USA.

Hooper, A.J., Marais, A.D., Tanyanyiwa, D.M., and Burnett, J.R. The C679X mutation in PCSK9 is present and lowers blood cholesterol in a Southern African population. Atherosclerosis Aug. 2007; 445-448, 193(2). Elsevier, USA.

Horton, J.D., Shah, N.A., Warrington, J.A., Anderson, N.N., Park, S.W., Brown, M.S., and Goldstein, J.L. Combined analysis of oligonucleotide microarray data from transgenic and knockout mice identifies direct SREBP target genes. Proc. Natl. Acad. Sci. U. S. A. Oct. 14, 2003; 12027-12032, 100(21). National Academy of Science, USA.

Hou, R., and Goldberg, A.C. Lowering low-density lipoprotein cholesterol: statins, ezetimibe, bile acid sequestrants, and combinations: comparative efficacy and safety. Endocrinol. Metab. Clin. North Am. Mar. 2009; 79-97, 38(1). Elsevier, USA.

Jorgensen, M.M., Jensen, O.N., Holst, H.U., Hansen, J.J., Corydon, T.J., Bross, P., Bolund, L., and Gregersen, N. Grp78 is involved in retention of mutant low density lipoprotein receptor protein in the endoplasmic reticulum. J. Biol. Chem. Oct. 27, 2000; 33861-33868, 275(43). American Society for Biochemistry and Molecular Biology, USA.

Kannel, W.B., Dawber, T.R., Kagan, A., Revotskie, N., and Stokes, J., 3rd. Factors of risk in the development of coronary heart disease—six year follow-up experience. The Framingham Study. Ann. Intern. Med. Jul. 1961; 33-50, 55. American College of Physicians, USA.

Kapur, N.K., and Musunuru, K. Clinical efficacy and safety of statins in managing cardiovascular risk. Vasc Health Risk Manag. May 2008; 341-353, 4(2). Dove Press, UK.

Kwon, H.J., Lagace, T.A., McNutt, M.C., Horton, J.D., and Deisenhofer, J. Molecular basis for LDL receptor recognition by PCSK9. Proc. Natl. Acad. Sci. U. S. A. Feb. 12, 2008; 1820-1825, 105(6). National Academy of Science, USA.

Lagace, T.A., Curtis, D.E., Garuti, R., McNutt, M.C., Park, S.W., Prather, H.B., Anderson, N.N., Ho, Y.K., Hammer, R.E., and Horton, J.D. Secreted PCSK9 decreases the number of LDL receptors in hepatocytes and in livers of parabiotic mice. J. Clin. Invest. Nov. 2006; 2995-3005, 116(11). American Society for Clinical Investigation, USA.

Lee, A.S. Glucose-regulated proteins in cancer: molecular mechanisms and therapeutic potential. Nature Reviews. Cancer Apr. 2014; 263-276, 14(4). Nature Publishing, UK.

Leigh, S.E., Foster, A.H., Whittall, R.A., Hubbart, C.S., and Humphries, S.E. Update and analysis of the University College London low density lipoprotein receptor familial hypercholesterolemia database. Ann. Hum. Genet. Jul. 2008; 485-498, 72(Pt 4). Wiley, USA.

Leigh, S.E., Leren, T.P., and Humphries, S.E. Commentary PCSK9 variants: A new database. Atherosclerosis Mar. 2009; 32-33, 203(1). Elsevier, USA.

Lusis, A.J. Atherosclerosis. Nature Sep. 14, 2000; 233-241, 407(6801). Nature Publishing, UK.

Macer, D.R., and Koch, G.L. Identification of a set of calcium-binding proteins in reticuloplasm, the luminal content of the endoplasmic reticulum. J. Cell Sci. Sep. 1988; 61-70, 91 (Pt 1). Company of Biologists, UK.

Mackay, J., and Mensah, G.A. The Atlas of Heart Disease and Stroke. World Health Organization, 2004;112p. World Health Organization, Switzerland.

Maki, R.G., Old, L.J., and Srivastava, P.K. Human homologue of murine tumor rejection antigen gp96: 5'-regulatory and coding regions and relationship to stress-induced proteins. Proc. Natl. Acad. Sci. U. S. A. Aug. 1990; 5658-5662, 87(15). National Academy of Science, USA.

Marduel, M., Ouguerram, K., Serre, V., Bonnefont-Rousselot, D., Marques-Pinheiro, A., Erik Berge, K., Devillers, M., Luc, G., Lecerf, J.M., Tosolini, L., et al. Description of a large family with autosomal dominant hypercholesterolemia associated with the APOE p.Leu167del mutation. Hum. Mutat. Jan. 2013; 83-87, 34(1). Wiley, USA.

Maxwell, K.N., and Breslow, J.L. Adenoviral-mediated expression of Pcsk9 in mice results in a low-density lipoprotein receptor knockout phenotype. Proc. Natl. Acad. Sci. U. S. A. May 4, 2004; 7100-7105, 101(18). National Academy of Science, USA.

Maxwell, K.N., Fisher, E.A., and Breslow, J.L. Overexpression of PCSK9 accelerates the degradation of the LDLR in a post-endoplasmic reticulum compartment. Proc. Natl. Acad. Sci. U. S. A. Feb. 8, 2005; 2069-2074, 102(6). National Academy of Science, USA.

Maxwell, K.N., Soccio, R.E., Duncan, E.M., Sehayek, E., and Breslow, J.L. Novel putative SREBP and LXR target genes identified by microarray analysis in liver of cholesterol-fed mice. J. Lipid Res. Nov. 2003; 2109-2119, 44(11). American Society for Biochemistry and Molecular Biology, USA.

McLaughlin, M., and Vandenbroeck, K. The endoplasmic reticulum protein folding factory and its chaperones: new targets for drug discovery? Br. J. Pharmacol. Jan. 2011; 328-345, 162(2). Wiley, USA.

McNutt, M.C., Lagace, T.A., and Horton, J.D. Catalytic activity is not required for secreted PCSK9 to reduce low density lipoprotein receptors in HepG2 cells. J. Biol. Chem. Jul. 20, 2007; 20799-20803, 282(29). American Society for Biochemistry and Molecular Biology, USA.

Müller, C. Xanthoma, hypercholesterolemia, angina pectoris. Acta Med Scand Suppl. Jan./Dec. 1938; 75-84, 95(S89). Wiley, USA.

Nassoury, N., Blasiole, D.A., Tebon Oler, A., Benjannet, S., Hamelin, J., Poupon, V., McPherson, P.S., Attie, A.D., Prat, A., and Seidah, N.G. The cellular trafficking of the secretory proprotein convertase PCSK9 and its dependence on the LDLR. Traffic Jun. 2007; 718-732, 8(6). Wiley, USA.

O'Keefe, J.H., Jr., Cordain, L., Harris, W.H., Moe, R.M., and Vogel, R. Optimal low-density lipoprotein is 50 to 70 mg/dl: lower is better and physiologically normal. J. Am. Coll. Cardiol. Jun. 2, 2004; 2142-2146, 43(11). Elsevier, USA.

Park, S.W., Moon, Y.A., and Horton, J.D. Post-transcriptional regulation of low density lipoprotein receptor protein by proprotein convertase subtilisin/kexin type 9a in mouse liver. J. Biol. Chem.

(56) References Cited

OTHER PUBLICATIONS

Nov. 26, 2004; 50630-50638, 279(48). American Society for Biochemistry and Molecular Biology, USA.
Pena, F., Jansens, A., van Zadelhoff, G., and Braakman, I. Calcium as a crucial cofactor for low density lipoprotein receptor folding in the endoplasmic reticulum. J. Biol. Chem. Mar. 19, 2010; 8656-8664, 285(12). American Society for Biochemistry and Molecular Biology, USA.
Poirier, S., and Mayer, G. The biology of PCSK9 from the endoplasmic reticulum to lysosomes: new and emerging therapeutics to control low-density lipoprotein cholesterol. Drug design, development and therapy Oct. 4, 2013; 1135-1148, 7. Dove Press, UK.
Poirier, S., Mayer, G., Benjannet, S., Bergeron, E., Marcinkiewicz, J., Nassoury, N., Mayer, H., Nimpf, J., Prat, A., and Seidah, N.G. The proprotein convertase PCSK9 induces the degradation of low density lipoprotein receptor (LDLR) and its closest family members VLDLR and ApoER2. J. Biol. Chem. Jan. 25, 2008; 2363-2372, 283(4). American Society for Biochemistry and Molecular Biology, USA.
Poirier, S., Mayer, G., Poupon, V., McPherson, P.S., Desjardins, R., Ly, K., Asselin, M.C., Day, R., Duclos, F.J., Witmer, M., et al. Dissection of the endogenous cellular pathways of PCSK9-induced low density lipoprotein receptor degradation: evidence for an intracellular route. J. Biol. Chem. Oct. 16, 2009; 28856-28864, 284(42). American Society for Biochemistry and Molecular Biology, USA.
Poirier, S., Samami, S., Mamarbachi, M., Demers, A., Chang, T.Y., Vance, D.E., Hatch, G.M., and Mayer, G. The epigenetic drug 5-azacytidine interferes with cholesterol and lipid metabolism. J. Biol. Chem. Jul. 4, 2014; 18736-18751, 289(27). American Society for Biochemistry and Molecular Biology, USA.
Rader, D.J., Cohen, J., and Hobbs, H.H. Monogenic hypercholesterolemia: new insights in pathogenesis and treatment. J. Clin. Invest. Jun. 2003; 1795-1803, 111(12). American Society for Clinical Investigation, USA.
Rashid, S., Curtis, D.E., Garuti, R., Anderson, N.N., Bashmakov, Y., Ho, Y.K., Hammer, R.E., Moon, Y.A., and Horton, J.D. Decreased plasma cholesterol and hypersensitivity to statins in mice lacking Pcsk9. Proc. Natl. Acad. Sci. U. S. A. Apr. 12, 2005; 5374-5379, 102(15). National Academy of Science, USA.
Examination report dated Jul. 2, 2019 for European Patent Application 16764326.1 corresponding to the present application.
Kliger, y et al., Peptides modulating conformational changes in secreted chaperones: From in silico design to preclinical proof of concept, PNAS Aug. 18, 2009 106 (33) pp. 13797-13801.
Chan JC et al. A proprotein convertase subtilisin/kexin type 9 neutralizing antibody reduces serum cholesterol in mice and nonhuman primates. Proc Natl Acad Sci U S A. Jun. 2009;106(24):9820-9825.
Sabatine MS et al.Efficacy and safety of evolocumab in reducing lipids and cardiovascular events. N Engl J Med. Apr. 2015;372(16):1500-1509.
Seidah, N.G., Benjannet, S., Wickham, L., Marcinkiewicz, J., Jasmin, S.B, Stifani, S., Basak, A., Prat, A., and Chretien, M. The secretory proprotein convertase neural apoptosis-regulated convertase 1 (NARC-1): liver regeneration and neuronal differentiation. Proc. Natl. Acad. Sci. U. S. A. Feb. 4, 2003; 928-933, 100(3). National Academy of Science, USA.
Stebbins, C.E., Russo, A.A., Schneider, C., Rosen, N., Hartl, F.U., and Pavletich, N.P. Crystal structure of an Hsp90-geldanamycin complex: targeting of a protein chaperone by an antitumor agent. Cell Apr. 18, 1997; 239-250, 89(2). Cell Press, USA.
Walley, K.R., Thain, K.R., Russell, J.A., Reilly, M.P., Meyer, N.J., Ferguson, J.F., Christie, J.D., Nakada, T.A., Fjell, C.D, Thair, S.A., et al. PCSK9 is a critical regulator of the innate immune response and septic shock outcome. Science Translational Medicine Oct. 15, 2014; 258ra143, 6(258). American Association for the Advancement of Science, USA.
Wang, Y., Huang, Y., Hobbs, H.H., and Cohen, J.C. Molecular characterization of proprotein convertase subtilisin/kexin type 9-mediated degradation of the LDLR. J. Lipid Res. Sep. 2012; 1932-1943, 53(9). American Society for Biochemistry and Molecular Biology, USA.
Weekes, M.P., Antrobus, R., Talbot, S., Hor, S., Simecek, N., Smith, D.L., Bloor, S., Randow, F., and Lehner, P.J. Proteomic plasma membrane profiling reveals an essential role for gp96 in the cell surface expression of LDLR family members, including the LDL receptor and LRP6. J Proteome Res. Mar. 2, 2012; 1475-1484, 11(3). American Chemical Society, USA.
Wenner Moyer, M. The search beyond statins. Nat. Med. Feb. 2010; 150-153, 16(2). Springer Nature, USA.
Wu, S., Hong, F., Gewirth, D., Guo, B., Liu, B., and Li, Z. The molecular chaperone gp96/GRP94 interacts with Toll-like receptors and integrins via its C-terminal hydrophobic domain. J. Biol. Chem. Feb. 24, 2012; 6735-6742, 287(9). American Society for Biochemistry and Molecular Biology, USA.
Yamamoto, T., Lu, C., and Ryan, R.O. A two-step binding model of PCSK9 interaction with the low density lipoprotein receptor. J. Biol. Chem. Feb. 18, 2011; 5464-5470, 286(7). American Society for Biochemistry and Molecular Biology, USA.
Yusuf, S., Hawken, S., Ounpuu, S., Dans, T., Avezum, A., Lanas, F., McQueen, M., Budaj, A., Pais, P., Varigos, J., et al. Effect of potentially modifiable risk factors associated with myocardial infarction in 52 countries (the INTERHEART study): case-control study. Lancet Sep. 11-17, 2004; 937-952, 364(9438). Elsevier, USA.
Zaid, A., Roubtsova, A., Essalmani, R., Marcinkiewicz, J., Chamberland, A., Hamelin, J., Tremblay, M., Jacques, H., Jin, W., Davignon, J., et al. Proprotein convertase subtilisin/kexin type 9 (PCSK9): hepatocyte-specific low-density lipoprotein receptor degradation and critical role in mouse liver regeneration. Hepatology Aug. 2008; 646-654, 48(2). Wiley, USA.
Zhang, D.W., Garuti, R., Tang, W.J., Cohen, J.C., and Hobbs, H.H. Structural requirements for PCSK9-mediated degradation of the low-density lipoprotein receptor. Proc. Natl. Acad. Sci. U. S. A. Sep. 2, 2008; 13045-13050, 105(35). National Academy of Science, USA.
Zhang, D.W., Lagace, T.A., Garuti, R., Zhao, Z., McDonald, M., Horton, J.D., Cohen, J.C., and Hobbs, H.H. Binding of proprotein convertase subtilisin/kexin type 9 to epidermal growth factor-like repeat A of low density lipoprotein receptor decreases receptor recycling and increases degradation. J. Biol. Chem. Jun. 22, 2007; 18602-18612, 282(25). American Society for Biochemistry and Molecular Biology, USA.
Zhao, Z., Tuakli-Wosornu, Y., Lagace, T.A., Kinch, L., Grishin, N.V., Horton, J.D., Cohen, J.C., and Hobbs, H.H. Molecular characterization of loss-of-function mutations in PCSK9 and identification of a compound heterozygote. Am. J. Hum. Genet. Sep. 2006; 514-523, 79(3). American Society of Human Genetics, USA.
International search report for PCT application PCT/IB2016/051559 filed Mar. 19, 2016, from which the present application is a national phase entry.
Written opinion for PCT application PCT/IB2016/051559 filed Mar. 19, 2016, from which the present application is a national phase entry.
Seidah et al. Annexin A2 Is a Natural Extrahepatic Inhibitor of the PCSK9-Induced LDL Receptor Degradation, Jul. 2012, PLoS ONE 7(7): e41865.
Poirier et al. Dissection of the endogenous cellular pathways of PCSK9-induced low density lipoprotein receptor degradation: evidence for an intracellular route. Oct. 16, 2009; J Biol Chem. 284(42):28856-64.
Poirier et al. GRP94 Regulates Circulating Cholesterol Levels through Blockade of PCSK9-Induced LDLR Degradation, Nov. 2015, Cell reports vol. 13, Issue 10, p. 2064-2071.
Gouni-Berthold et al.PCSK9 Antibodies for the Treatment of Hypercholesterolemia, Dec. 2014, Nutrients. 6(12): 5517-5533.
Extended search report dated Jul. 2, 2018 for European Patent Application 16764326.1 corresponding to the present application.
Poirier S et al. , "GRP94 regulates circulating cholesterol levels through blockade of PCSK9-induced LDLR degradation", J. Artheriosclerosis, Jul. 2015, , p. e16, vol. 241, Issue 1.

(56) References Cited

OTHER PUBLICATIONS

Anonymous—UniProt Consortium UniParc databse record UPI0000577ABE—Sequence first seen Aug. 2005—Retrieved from the Internet by examiner for European Patent Application 16764326.1 on Jun. 15, 2018.
Anonymous—UniProt Consortium UniParc databse record UPI00001E5310—Sequence first seen Nov. 2003—Retrieved from the Internet by examiner for European Patent Application 16764326.1 on Jun. 15, 2018.
Anonymous—UniProt Consortium UniParc databse record UPI00042BBF57—Sequence first seen Mar. 2014—Retrieved from the Internet by examiner for European Patent Application 16764326.1 on Jun. 15, 2018.
Sequence No. 18555 of the sequence listing of PCT Patent application publication WO200164835A2 of Tang et al. published Sep. 7, 2001, cited by European Search report dated Jul. 2, 2018 for European Patent Application 16764326.1 corresponding to the present application.

* cited by examiner a
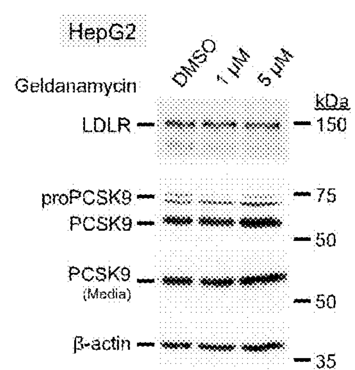
b
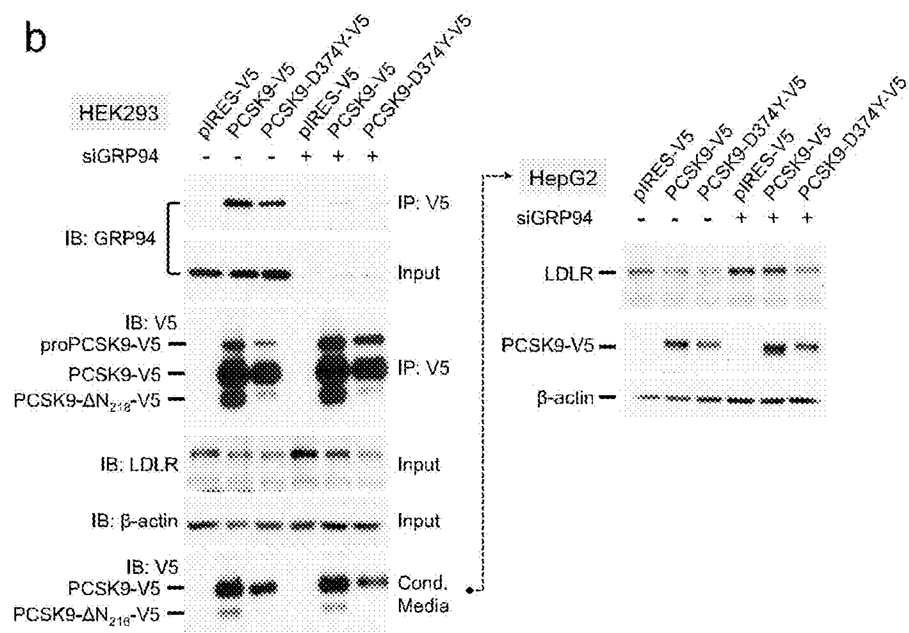
Figure 3

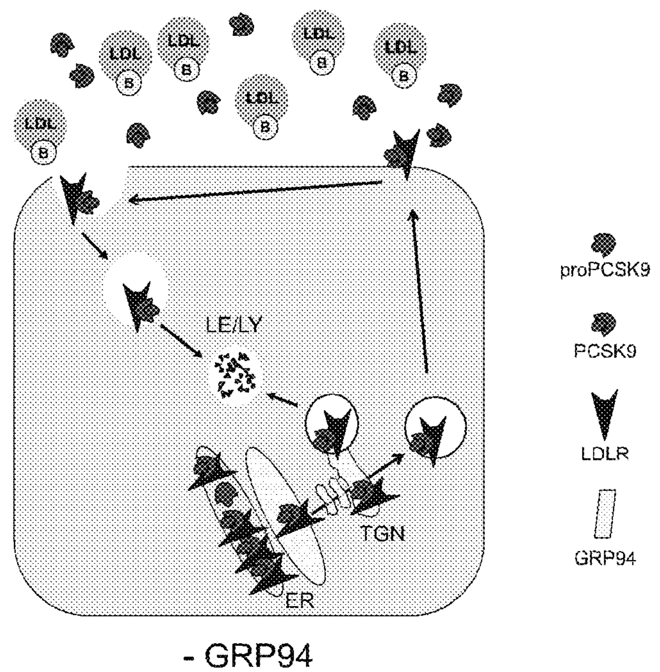
- GRP94
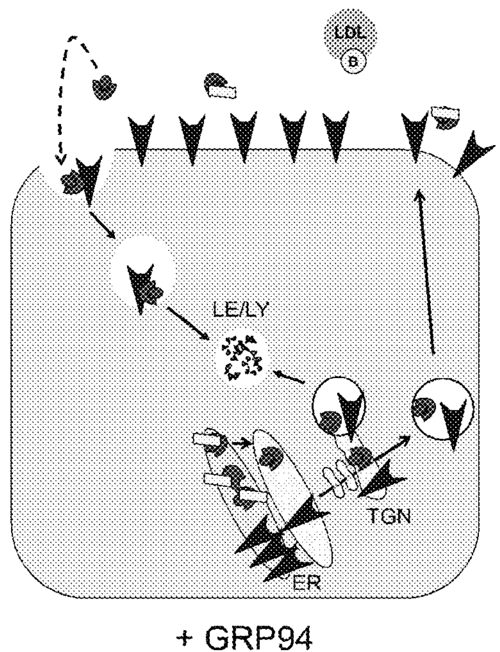
+ GRP94
Figure 9

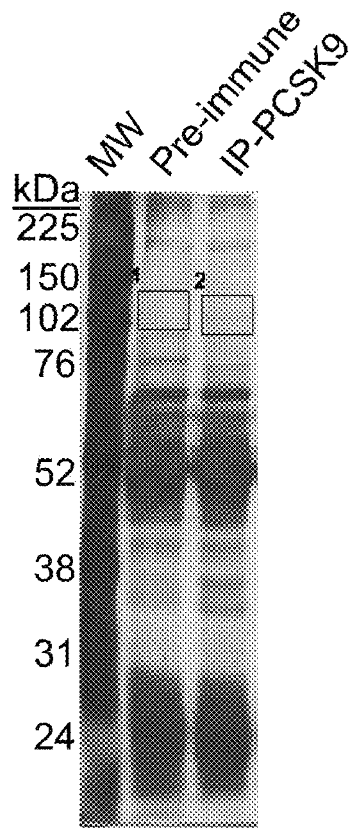

Band 1

| prot_hit_num | prot_acc | prot_desc | prot_score | prot_mass | prot_matches | prot_cover | prot_len | prot_pi |
|---|---|---|---|---|---|---|---|---|
| 1 | gi\|11935049 | keratin 1 [Homo sapiens] | 1719 | 66027 | 67 | 41.1 | 644 | 8.16 |
| 2 | gi\|21961605 | Keratin 10 [Homo sapiens] | 1109 | 58792 | 39 | 39.4 | 584 | 5.09 |
| 3 | gi\|55956899 | keratin 9 [Homo sapiens] | 796 | 62027 | 20 | 26.0 | 623 | 5.14 |
| 4 | gi\|12803709 | Keratin 14 [Homo sapiens] | 698 | 51619 | 30 | 27.1 | 472 | 5.09 |
| 5 | gi\|24430192 | keratin 16 [Homo sapiens] | 614 | 51236 | 31 | 26.0 | 473 | 4.99 |
| 6 | gi\|47132620 | keratin 2 [Homo sapiens] | 418 | 65393 | 9 | 15.3 | 639 | 8.07 |
| 7 | gi\|119617032 | keratin 6B, isoform CRA_a [Homo sapiens] | 234 | 59874 | 5 | 7.1 | 563 | 8.38 |
| 8 | gi\|386849 | keratin type II [Homo sapiens] | 209 | 59916 | 5 | 6.9 | 563 | 8.05 |
| 9 | gi\|28592 | serum albumin [Homo sapiens] | 129 | 69321 | 5 | 5.9 | 609 | 6.05 |
| 10 | gi\|185362 | IgG [Homo sapiens] | 56 | 52060 | 6 | 3.2 | 476 | 8.60 |

Band 2

| prot_hit_num | prot_acc | prot_desc | prot_score | prot_mass | prot_matches | prot_cover | prot_len | prot_pi |
|---|---|---|---|---|---|---|---|---|
| 1 | gi\|11935049 | keratin 1 [Homo sapiens] | 1777 | 66027 | 66 | 42.4 | 644 | 8.16 |
| 2 | gi\|21961605 | Keratin 10 [Homo sapiens] | 1009 | 58792 | 33 | 31.3 | 584 | 5.09 |
| 3 | gi\|55956899 | keratin 9 [Homo sapiens] | 705 | 62027 | 24 | 23.4 | 623 | 5.14 |
| 4 | gi\|15010550 | heat shock protein gp96 precursor [Homo sapiens] | 623 | 90138 | 28 | 22.0 | 782 | 4.73 |
| 5 | gi\|1195531 | type I keratin 16 [Homo sapiens] | 533 | 51206 | 23 | 22.4 | 473 | 4.99 |
| 6 | gi\|12803709 | Keratin 14 [Homo sapiens] | 527 | 51619 | 23 | 21.8 | 472 | 5.09 |
| 7 | gi\|47132620 | keratin 2 [Homo sapiens] | 493 | 65393 | 11 | 9.4 | 639 | 8.07 |
| 8 | gi\|386849 | keratin type II [Homo sapiens] | 254 | 59916 | 7 | 5.3 | 563 | 8.05 |
| 9 | gi\|28592 | serum albumin [Homo sapiens] | 94 | 69321 | 3 | 3.9 | 609 | 6.05 |
| 10 | gi\|185362 | IgG [Homo sapiens] | 63 | 52060 | 11 | 3.2 | 476 | 8.60 |

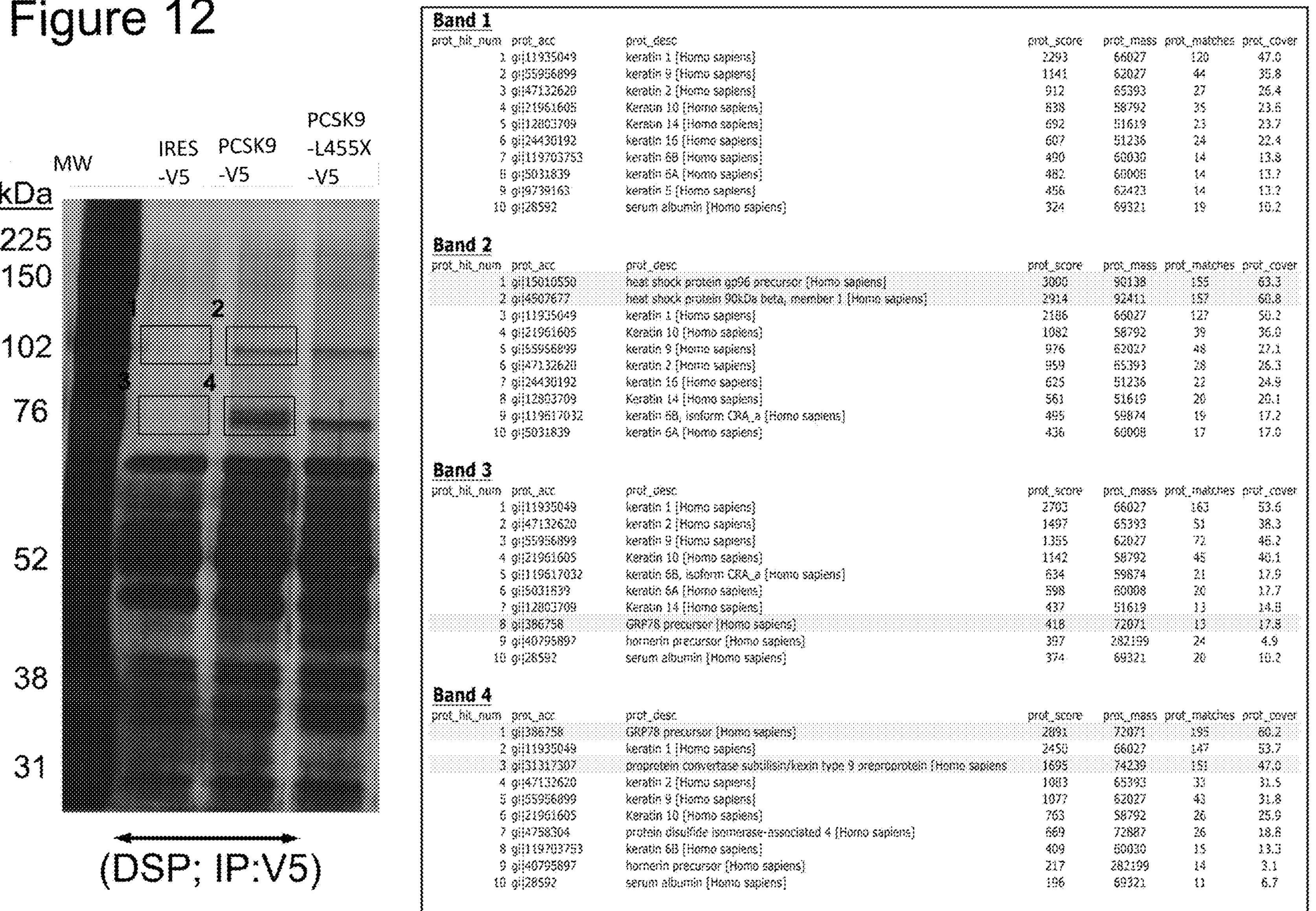

Band 1

| prot_hit_num | prot_acc | prot_desc | prot_score | prot_mass | prot_matches | prot_cover |
|---|---|---|---|---|---|---|
| 1 | gi\|11935049 | keratin 1 [Homo sapiens] | 2293 | 66027 | 120 | 47.0 |
| 2 | gi\|55956899 | keratin 9 [Homo sapiens] | 1141 | 62027 | 44 | 35.8 |
| 3 | gi\|47132620 | keratin 2 [Homo sapiens] | 912 | 65393 | 27 | 26.4 |
| 4 | gi\|21961605 | Keratin 10 [Homo sapiens] | 838 | 58792 | 35 | 23.6 |
| 5 | gi\|12803709 | Keratin 14 [Homo sapiens] | 692 | 51619 | 23 | 23.7 |
| 6 | gi\|24430192 | keratin 16 [Homo sapiens] | 607 | 51236 | 24 | 22.4 |
| 7 | gi\|119703753 | keratin 6B [Homo sapiens] | 490 | 60030 | 14 | 13.8 |
| 8 | gi\|5031839 | keratin 6A [Homo sapiens] | 482 | 60008 | 14 | 13.7 |
| 9 | gi\|9739163 | keratin 5 [Homo sapiens] | 456 | 62423 | 14 | 13.2 |
| 10 | gi\|28592 | serum albumin [Homo sapiens] | 324 | 69321 | 19 | 10.2 |

Band 2

| prot_hit_num | prot_acc | prot_desc | prot_score | prot_mass | prot_matches | prot_cover |
|---|---|---|---|---|---|---|
| 1 | gi\|15010550 | heat shock protein gp96 precursor [Homo sapiens] | 3000 | 90138 | 155 | 63.3 |
| 2 | gi\|4507677 | heat shock protein 90kDa beta, member 1 [Homo sapiens] | 2914 | 92411 | 157 | 60.8 |
| 3 | gi\|11935049 | keratin 1 [Homo sapiens] | 2186 | 66027 | 127 | 50.2 |
| 4 | gi\|21961605 | Keratin 10 [Homo sapiens] | 1082 | 58792 | 39 | 36.0 |
| 5 | gi\|55956899 | keratin 9 [Homo sapiens] | 976 | 62027 | 48 | 27.1 |
| 6 | gi\|47132620 | keratin 2 [Homo sapiens] | 959 | 65393 | 28 | 26.3 |
| 7 | gi\|24430192 | keratin 16 [Homo sapiens] | 625 | 51236 | 22 | 24.9 |
| 8 | gi\|12803709 | Keratin 14 [Homo sapiens] | 561 | 51619 | 20 | 20.1 |
| 9 | gi\|119617032 | keratin 6B, isoform CRA_a [Homo sapiens] | 495 | 59874 | 19 | 17.2 |
| 10 | gi\|5031839 | keratin 6A [Homo sapiens] | 436 | 60008 | 17 | 17.0 |

Band 3

| prot_hit_num | prot_acc | prot_desc | prot_score | prot_mass | prot_matches | prot_cover |
|---|---|---|---|---|---|---|
| 1 | gi\|11935049 | keratin 1 [Homo sapiens] | 2703 | 66027 | 163 | 53.6 |
| 2 | gi\|47132620 | keratin 2 [Homo sapiens] | 1497 | 65393 | 51 | 38.3 |
| 3 | gi\|55956899 | keratin 9 [Homo sapiens] | 1355 | 62027 | 72 | 46.2 |
| 4 | gi\|21961605 | Keratin 10 [Homo sapiens] | 1142 | 58792 | 45 | 40.1 |
| 5 | gi\|119617032 | keratin 6B, isoform CRA_a [Homo sapiens] | 634 | 59874 | 21 | 17.9 |
| 6 | gi\|5031839 | keratin 6A [Homo sapiens] | 598 | 60008 | 20 | 17.7 |
| 7 | gi\|12803709 | Keratin 14 [Homo sapiens] | 437 | 51619 | 13 | 14.8 |
| 8 | gi\|386758 | GRP78 precursor [Homo sapiens] | 418 | 72071 | 13 | 17.8 |
| 9 | gi\|40795897 | hornerin precursor [Homo sapiens] | 397 | 282199 | 24 | 4.9 |
| 10 | gi\|28592 | serum albumin [Homo sapiens] | 374 | 69321 | 20 | 10.2 |

Band 4

| prot_hit_num | prot_acc | prot_desc | prot_score | prot_mass | prot_matches | prot_cover |
|---|---|---|---|---|---|---|
| 1 | gi\|386758 | GRP78 precursor [Homo sapiens] | 2891 | 72071 | 195 | 60.2 |
| 2 | gi\|11935049 | keratin 1 [Homo sapiens] | 2450 | 66027 | 147 | 53.7 |
| 3 | gi\|31317307 | proprotein convertase subtilisin/kexin type 9 preproprotein [Homo sapiens | 1695 | 74239 | 151 | 47.0 |
| 4 | gi\|47132620 | keratin 2 [Homo sapiens] | 1083 | 65393 | 33 | 31.5 |
| 5 | gi\|55956899 | keratin 9 [Homo sapiens] | 1077 | 62027 | 43 | 31.8 |
| 6 | gi\|21961605 | Keratin 10 [Homo sapiens] | 763 | 58792 | 26 | 25.9 |
| 7 | gi\|4758304 | protein disulfide isomerase-associated 4 [Homo sapiens] | 669 | 72887 | 26 | 18.8 |
| 8 | gi\|119703753 | keratin 6B [Homo sapiens] | 409 | 60030 | 15 | 13.3 |
| 9 | gi\|40795897 | hornerin precursor [Homo sapiens] | 217 | 282199 | 14 | 3.1 |
| 10 | gi\|28592 | serum albumin [Homo sapiens] | 196 | 69321 | 11 | 6.7 |

| | **Forward (5'->3')** | **Reverse (5'->3')** |
|---|---|---|
| pCMV-SPORT6-hGRP94ΔKDEL-HA | PCR1: ACTGTCTGGGACTGGGAACTT<br>PCR2: CAGCAAAGGAATCTACAGCTGAATACCCATATGAC; AGCTGAATACCCATATGACGTCCCGGATTACGCT | PCR1: GTCATATGGGTATTCAGCTGTAGATTCCTTTGC<br>PCR2: AGCCTCGAGTTAAGCGTAATCCGGGACGTCAT |
| pCMV-SPORT6-hGRP94-AA1-ΔKDEL-HA | PCR1: ACTGTCTGGGACTGGGAACTT<br>PCR2: CGCAGCGTCTGCCGCAGCTGCTGCAATCATGAAA GCACAAGCGTACC | PCR1: CAGCTGCGGCAGACGCTGCGTACTGCCTGGCCAC<br>PCR2: ACGGCCAGTGCCTAGCTTAT |
| pCMV-SPORT6-hGRP94-AA2-ΔKDEL-HA | PCR1: ACTGTCTGGGACTGGGAACTT<br>PCR2: ACGGGCAAGGCCATCTCTACAAATGCCGCTGCGAGT CAGAAG | PCR1: GCATTTGTAGAGATGGCCTTGCCCGTTGCGTAA GCTTGTGCTTTCA<br>PCR2: ACGGCCAGTGCCTAGCTTAT |
| pcDNA3.1-hCBD-CT-ΔKDEL-HA | PCR1: ACAGGATCCATGAGGGCCCTGTGGGTG<br>PCR2: TCGGTCAGAGCTTACGGATGGTCTGGCAA | PCR1: CAGACCATCCGTAAGCTCTGACCGACCCGA<br>PCR2: ACGGCCAGTGCCTAGCTTAT |
| pZac2.1-hCBD-CT-ΔKDEL-HA | ACAGGATCCATGAGGGCCCTGTGGGTG | CAGACCATCCGTAAGCTCTGACCGACCCGA |
| pET24b(+)-hCBD-CT-ΔKDEL-HA-$His_6$ | ATGGCTAGCTACGGATGGTCTGGCAACATGGA | ATACTCGAGAGCGTAATCCGGGACGTCATATGGG |
| pIRES-hPCSK9-V5-$His_6$ | PCR1: CAGACCGGTAAGCCTATCCCTAACCCTTTACTCGG-TCTCGATT; AACCCTTTACTCGGTCTCGATTCTACGCATCA-TCA | PCR1: CGGATCCCTAGTGATGATGATGATGATGCGTAGAA; GGAGGGAGAGGGGCGGATCCCTAGTGATGATGATGA |
| pCMV-hLDLR-EGFP | PCR2: TAGGGATCCGCCCCTCTCCCTC<br>TAACACCGGTATGGTGAGCAAGGGCGAGGAGC | PCR2: GGTCGCTACAGACGTTGTTT<br>CTCTACAAATGTGGTATGGCTGA |
| | **Single stranded DNA (5'->3')** | |
| pU6 ITR-shScramble | TAACCCTCACTAAAGGGACTCAAGCTTTTCCAAAAAA***CCTAAGGTTAAGTCGCCCTCG***CTCTTGA***CGAGGGCGACTTAACCTTAGG***CGGGATCCATCGAGCCCTATAGTGAGTCGTATTA | |
| pU6 ITR-shGrp94 | TAACCCTCACTAAAGGGACTCAAGCTTTTCCAAAAAA***GCTATTCAGTTGGATGGGTTA***CTCTTGA***TAACCCATCCAACTGAATAGC***CGGGATCCATCGAGCCCTATAGTGAGTCGTATTA | |
| Amplification primers | TAACCCTCACTAAAGGGACTC | TAATACGACTCACTATAGGGCTC |

Figure 13

SEQUENCE LISTING

<160> NUMBER OF SEQ ID NOS: 79

<210> SEQ ID NO 1
<211> LENGTH: 692
<212> TYPE: PRT
<213> ORGANISM: Homo Sapiens

<400> SEQUENCE: 1

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365
```

```
Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690


<210> SEQ ID NO 2
<211> LENGTH: 860
<212> TYPE: PRT
<213> ORGANISM: Homo Sapiens

<400> SEQUENCE: 2

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45
```

```
Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460
```

```
Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860


<210> SEQ ID NO 3
<211> LENGTH: 803
<212> TYPE: PRT
```

```
<213> ORGANISM: Homo Sapiens

<400> SEQUENCE: 3

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
    290                 295                 300

Glu Ser Asp Asp Glu Ala Ala Val Glu Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400
```

```
Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685

Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Glu Pro Glu Glu Glu Pro Glu Glu Thr Ala Glu
        755                 760                 765

Asp Thr Thr Glu Asp Thr Glu Gln Asp Glu Asp Glu Glu Met Asp Val
    770                 775                 780

Gly Thr Asp Glu Glu Glu Glu Thr Ala Lys Glu Ser Thr Ala Glu Lys
785                 790                 795                 800

Asp Glu Leu
```

<210> SEQ ID NO 4

<211> LENGTH: 27
<212> TYPE: PRT
<213> ORGANISM: Artificial Sequence
<220> FEATURE:
<223> OTHER INFORMATION: Synthetic

<400> SEQUENCE: 4

```
Tyr Gly Trp Ser Gly Asn Met Glu Arg Ile Met Lys Ala Gln Ala Tyr
1               5                   10                  15

Gln Thr Gly Lys Asp Ile Ser Thr Asn Tyr Tyr
            20                  25
```

<210> SEQ ID NO 5
<211> LENGTH: 48
<212> TYPE: PRT
<213> ORGANISM: Artificial Sequence
<220> FEATURE:
<223> OTHER INFORMATION: Synthetic

<400> SEQUENCE: 5

```
Met Arg Ala Leu Trp Val Leu Gly Leu Cys Cys Val Leu Leu Thr Phe
1               5                   10                  15

Gly Ser Val Arg Ala Tyr Gly Trp Ser Gly Asn Met Glu Arg Ile Met
            20                  25                  30

Lys Ala Gln Ala Tyr Gln Thr Gly Lys Asp Ile Ser Thr Asn Tyr Tyr
        35                  40                  45
```

<210> SEQ ID NO 6
<211> LENGTH: 148
<212> TYPE: PRT
<213> ORGANISM: Artificial Sequence
<220> FEATURE:
<223> OTHER INFORMATION: Synthetic

<400> SEQUENCE: 6

```
Tyr Gly Trp Ser Gly Asn Met Glu Arg Ile Met Lys Ala Gln Ala Tyr
1               5                   10                  15

Gln Thr Gly Lys Asp Ile Ser Thr Asn Tyr Tyr Ala Ser Gln Lys Lys
            20                  25                  30

Thr Phe Glu Ile Asn Pro Arg His Pro Leu Ile Arg Asp Met Leu Arg
        35                  40                  45

Arg Ile Lys Glu Asp Glu Asp Asp Lys Thr Val Leu Asp Leu Ala Val
    50                  55                  60

Val Leu Phe Glu Thr Ala Thr Leu Arg Ser Gly Tyr Leu Leu Pro Asp
65                  70                  75                  80

Thr Lys Ala Tyr Gly Asp Arg Ile Glu Arg Met Leu Arg Leu Ser Leu
                85                  90                  95

Asn Ile Asp Pro Asp Ala Lys Val Glu Glu Glu Pro Glu Glu Glu Pro
            100                 105                 110

Glu Glu Thr Ala Glu Asp Thr Thr Glu Asp Thr Glu Gln Asp Glu Asp
        115                 120                 125

Glu Glu Met Asp Val Gly Thr Asp Glu Glu Glu Glu Thr Ala Lys Glu
    130                 135                 140

Ser Thr Ala Glu
145
```

<210> SEQ ID NO 7
<211> LENGTH: 169
<212> TYPE: PRT
<213> ORGANISM: Artificial Sequence
<220> FEATURE:

<223> OTHER INFORMATION: Synthetic

<400> SEQUENCE: 7

```
Met Arg Ala Leu Trp Val Leu Gly Leu Cys Cys Val Leu Leu Thr Phe
1               5                   10                  15

Gly Ser Val Arg Ala Tyr Gly Trp Ser Gly Asn Met Glu Arg Ile Met
            20                  25                  30

Lys Ala Gln Ala Tyr Gln Thr Gly Lys Asp Ile Ser Thr Asn Tyr Tyr
        35                  40                  45

Ala Ser Gln Lys Lys Thr Phe Glu Ile Asn Pro Arg His Pro Leu Ile
    50                  55                  60

Arg Asp Met Leu Arg Arg Ile Lys Glu Asp Glu Asp Asp Lys Thr Val
65                  70                  75                  80

Leu Asp Leu Ala Val Val Leu Phe Glu Thr Ala Thr Leu Arg Ser Gly
                85                  90                  95

Tyr Leu Leu Pro Asp Thr Lys Ala Tyr Gly Asp Arg Ile Glu Arg Met
            100                 105                 110

Leu Arg Leu Ser Leu Asn Ile Asp Pro Asp Ala Lys Val Glu Glu Glu
        115                 120                 125

Pro Glu Glu Glu Pro Glu Glu Thr Ala Glu Asp Thr Thr Glu Asp Thr
    130                 135                 140

Glu Gln Asp Glu Asp Glu Glu Met Asp Val Gly Thr Asp Glu Glu Glu
145                 150                 155                 160

Glu Thr Ala Lys Glu Ser Thr Ala Glu
                165
```

<210> SEQ ID NO 8
<211> LENGTH: 27
<212> TYPE: PRT
<213> ORGANISM: Artificial Sequence
<220> FEATURE:
<223> OTHER INFORMATION: Synthetic

<400> SEQUENCE: 8

```
Tyr Gly Trp Thr Gly Asn Met Glu Arg Ile Met Lys Ala Gln Ala Tyr
1               5                   10                  15

Gln Thr Gly Lys Asp Ile Ser Thr Asn Tyr Tyr
            20                  25
```

<210> SEQ ID NO 9
<211> LENGTH: 27
<212> TYPE: PRT
<213> ORGANISM: Artificial Sequence
<220> FEATURE:
<223> OTHER INFORMATION: Synthetic

<400> SEQUENCE: 9

```
Tyr Gly Trp Ser Gly Asn Ser Glu Arg Ile Met Lys Ala Gln Ala Tyr
1               5                   10                  15

Gln Thr Gly Lys Asp Ile Ser Thr Asn Tyr Tyr
            20                  25
```

<210> SEQ ID NO 10
<211> LENGTH: 27
<212> TYPE: PRT
<213> ORGANISM: Artificial Sequence
<220> FEATURE:
<223> OTHER INFORMATION: Synthetic

<400> SEQUENCE: 10

```
Tyr Gly Trp Ser Gly Asn Ser Glu Arg Ile Met Lys Ala Gln Ala Tyr
1               5                   10                  15

Gln Thr Gly Lys Asp Ile Ser Thr Asn Tyr Tyr
            20                  25


<210> SEQ ID NO 11
<211> LENGTH: 27
<212> TYPE: PRT
<213> ORGANISM: Artificial Sequence
<220> FEATURE:
<223> OTHER INFORMATION: Synthetic

<400> SEQUENCE: 11

Tyr Gly Trp Ser Gly Asn Met Asn Arg Ile Met Lys Ala Gln Ala Tyr
1               5                   10                  15

Gln Thr Gly Lys Asp Ile Ser Thr Asn Tyr Tyr
            20                  25


<210> SEQ ID NO 12
<211> LENGTH: 27
<212> TYPE: PRT
<213> ORGANISM: Artificial Sequence
<220> FEATURE:
<223> OTHER INFORMATION: Synthetic

<400> SEQUENCE: 12

Tyr Gly Trp Ser Gly Asn Met Glu Lys Ile Met Lys Ala Gln Ala Tyr
1               5                   10                  15

Gln Thr Gly Lys Asp Ile Ser Thr Asn Tyr Tyr
            20                  25


<210> SEQ ID NO 13
<211> LENGTH: 27
<212> TYPE: PRT
<213> ORGANISM: Artificial Sequence
<220> FEATURE:
<223> OTHER INFORMATION: Synthetic

<400> SEQUENCE: 13

Tyr Gly Trp Ser Gly Asn Met Glu Arg Leu Met Lys Ala Gln Ala Tyr
1               5                   10                  15

Gln Thr Gly Lys Asp Ile Ser Thr Asn Tyr Tyr
            20                  25


<210> SEQ ID NO 14
<211> LENGTH: 27
<212> TYPE: PRT
<213> ORGANISM: Artificial Sequence
<220> FEATURE:
<223> OTHER INFORMATION: Synthetic

<400> SEQUENCE: 14

Tyr Gly Trp Ser Gly Asn Met Glu Arg Val Met Lys Ala Gln Ala Tyr
1               5                   10                  15

Gln Thr Gly Lys Asp Ile Ser Thr Asn Tyr Tyr
            20                  25


<210> SEQ ID NO 15
<211> LENGTH: 27
<212> TYPE: PRT
<213> ORGANISM: Artificial Sequence
<220> FEATURE:
<223> OTHER INFORMATION: Synthetic

<400> SEQUENCE: 15
```

```
Tyr Gly Trp Ser Gly Asn Met Glu Arg Ile Ser Lys Ala Gln Ala Tyr
1               5                   10                  15

Gln Thr Gly Lys Asp Ile Ser Thr Asn Tyr Tyr
            20                  25


<210> SEQ ID NO 16
<211> LENGTH: 27
<212> TYPE: PRT
<213> ORGANISM: Artificial Sequence
<220> FEATURE:
<223> OTHER INFORMATION: Synthetic

<400> SEQUENCE: 16

Tyr Gly Trp Ser Gly Asn Met Glu Arg Ile Met Arg Ala Gln Ala Tyr
1               5                   10                  15

Gln Thr Gly Lys Asp Ile Ser Thr Asn Tyr Tyr
            20                  25


<210> SEQ ID NO 17
<211> LENGTH: 27
<212> TYPE: PRT
<213> ORGANISM: Artificial Sequence
<220> FEATURE:
<223> OTHER INFORMATION: Synthetic

<400> SEQUENCE: 17

Tyr Gly Trp Ser Gly Asn Met Glu Arg Ile Met Lys Leu Gln Ala Tyr
1               5                   10                  15

Gln Thr Gly Lys Asp Ile Ser Thr Asn Tyr Tyr
            20                  25


<210> SEQ ID NO 18
<211> LENGTH: 27
<212> TYPE: PRT
<213> ORGANISM: Artificial Sequence
<220> FEATURE:
<223> OTHER INFORMATION: Synthetic

<400> SEQUENCE: 18

Tyr Gly Trp Ser Gly Asn Met Glu Arg Ile Met Lys Val Gln Ala Tyr
1               5                   10                  15

Gln Thr Gly Lys Asp Ile Ser Thr Asn Tyr Tyr
            20                  25


<210> SEQ ID NO 19
<211> LENGTH: 27
<212> TYPE: PRT
<213> ORGANISM: Artificial Sequence
<220> FEATURE:
<223> OTHER INFORMATION: Synthetic

<400> SEQUENCE: 19

Tyr Gly Trp Ser Gly Asn Met Glu Arg Ile Met Lys Ala Asn Ala Tyr
1               5                   10                  15

Gln Thr Gly Lys Asp Ile Ser Thr Asn Tyr Tyr
            20                  25


<210> SEQ ID NO 20
<211> LENGTH: 27
<212> TYPE: PRT
<213> ORGANISM: Artificial Sequence
<220> FEATURE:
<223> OTHER INFORMATION: Synthetic
```

<400> SEQUENCE: 20

```
Tyr Gly Trp Ser Gly Asn Met Glu Arg Ile Met Lys Ala Gln Val Tyr
1               5                   10                  15

Gln Thr Gly Lys Asp Ile Ser Thr Asn Tyr Tyr
            20                  25
```

<210> SEQ ID NO 21
<211> LENGTH: 27
<212> TYPE: PRT
<213> ORGANISM: Artificial Sequence
<220> FEATURE:
<223> OTHER INFORMATION: Synthetic

<400> SEQUENCE: 21

```
Tyr Gly Trp Ser Gly Asn Met Glu Arg Ile Met Lys Ala Gln Leu Tyr
1               5                   10                  15

Gln Thr Gly Lys Asp Ile Ser Thr Asn Tyr Tyr
            20                  25
```

<210> SEQ ID NO 22
<211> LENGTH: 27
<212> TYPE: PRT
<213> ORGANISM: Artificial Sequence
<220> FEATURE:
<223> OTHER INFORMATION: Synthetic

<400> SEQUENCE: 22

```
Tyr Gly Trp Ser Gly Asn Met Glu Arg Ile Met Lys Ala Gln Ile Tyr
1               5                   10                  15

Gln Thr Gly Lys Asp Ile Ser Thr Asn Tyr Tyr
            20                  25
```

<210> SEQ ID NO 23
<211> LENGTH: 27
<212> TYPE: PRT
<213> ORGANISM: Artificial Sequence
<220> FEATURE:
<223> OTHER INFORMATION: Synthetic

<400> SEQUENCE: 23

```
Tyr Gly Trp Ser Gly Asn Met Glu Arg Ile Met Lys Ala Gln Ala Tyr
1               5                   10                  15

Asn Thr Gly Lys Asp Ile Ser Thr Asn Tyr Tyr
            20                  25
```

<210> SEQ ID NO 24
<211> LENGTH: 27
<212> TYPE: PRT
<213> ORGANISM: Artificial Sequence
<220> FEATURE:
<223> OTHER INFORMATION: Synthetic

<400> SEQUENCE: 24

```
Tyr Gly Trp Ser Gly Asn Met Glu Arg Ile Met Lys Ala Gln Ala Tyr
1               5                   10                  15

Gln Ser Gly Lys Asp Ile Ser Thr Asn Tyr Tyr
            20                  25
```

<210> SEQ ID NO 25
<211> LENGTH: 27
<212> TYPE: PRT
<213> ORGANISM: Artificial Sequence
<220> FEATURE:
<223> OTHER INFORMATION: Synthetic

<400> SEQUENCE: 25

Tyr Gly Trp Ser Gly Asn Met Glu Arg Ile Met Lys Ala Gln Ala Tyr
1 5 10 15

Gln Thr Gly Arg Asp Ile Ser Thr Asn Tyr Tyr
20 25

<210> SEQ ID NO 26
<211> LENGTH: 27
<212> TYPE: PRT
<213> ORGANISM: Artificial Sequence
<220> FEATURE:
<223> OTHER INFORMATION: Synthetic

<400> SEQUENCE: 26

Tyr Gly Trp Ser Gly Asn Met Glu Arg Ile Met Lys Ala Gln Ala Tyr
1 5 10 15

Gln Thr Gly Lys Glu Ile Ser Thr Asn Tyr Tyr
20 25

<210> SEQ ID NO 27
<211> LENGTH: 27
<212> TYPE: PRT
<213> ORGANISM: Artificial Sequence
<220> FEATURE:
<223> OTHER INFORMATION: Synthetic

<400> SEQUENCE: 27

Tyr Gly Trp Ser Gly Asn Met Glu Arg Ile Met Lys Ala Gln Ala Tyr
1 5 10 15

Gln Thr Gly Lys Asp Leu Ser Thr Asn Tyr Tyr
20 25

<210> SEQ ID NO 28
<211> LENGTH: 27
<212> TYPE: PRT
<213> ORGANISM: Artificial Sequence
<220> FEATURE:
<223> OTHER INFORMATION: Synthetic

<400> SEQUENCE: 28

Tyr Gly Trp Ser Gly Asn Met Glu Arg Ile Met Lys Ala Gln Ala Tyr
1 5 10 15

Gln Thr Gly Lys Asp Val Ser Thr Asn Tyr Tyr
20 25

<210> SEQ ID NO 29
<211> LENGTH: 27
<212> TYPE: PRT
<213> ORGANISM: Artificial Sequence
<220> FEATURE:
<223> OTHER INFORMATION: Synthetic

<400> SEQUENCE: 29

Tyr Gly Trp Ser Gly Asn Met Glu Arg Ile Met Lys Ala Gln Ala Tyr
1 5 10 15

Gln Thr Gly Lys Asp Ala Ser Thr Asn Tyr Tyr
20 25

<210> SEQ ID NO 30
<211> LENGTH: 27
<212> TYPE: PRT
<213> ORGANISM: Artificial Sequence
<220> FEATURE:

<223> OTHER INFORMATION: Synthetic

<400> SEQUENCE: 30

```
Tyr Gly Trp Ser Gly Asn Met Glu Arg Ile Met Lys Ala Gln Ala Tyr
1               5                   10                  15

Gln Thr Gly Lys Asp Ile Thr Thr Asn Tyr Tyr
            20                  25
```

<210> SEQ ID NO 31
<211> LENGTH: 27
<212> TYPE: PRT
<213> ORGANISM: Artificial Sequence
<220> FEATURE:
<223> OTHER INFORMATION: Synthetic

<400> SEQUENCE: 31

```
Tyr Gly Trp Ser Gly Asn Met Glu Arg Ile Met Lys Ala Gln Ala Tyr
1               5                   10                  15

Gln Thr Gly Lys Asp Ile Ser Ser Asn Tyr Tyr
            20                  25
```

<210> SEQ ID NO 32
<211> LENGTH: 27
<212> TYPE: PRT
<213> ORGANISM: Artificial Sequence
<220> FEATURE:
<223> OTHER INFORMATION: Synthetic

<400> SEQUENCE: 32

```
Tyr Gly Trp Ser Gly Asn Met Glu Arg Ile Met Lys Ala Gln Ala Tyr
1               5                   10                  15

Gln Thr Gly Lys Asp Ile Ser Thr Gln Tyr Tyr
            20                  25
```

<210> SEQ ID NO 33
<211> LENGTH: 81
<212> TYPE: DNA
<213> ORGANISM: Artificial Sequence
<220> FEATURE:
<223> OTHER INFORMATION: Synthetic

<400> SEQUENCE: 33

```
tacggatggt ctggcaacat ggagagaatc atgaaagcac aagcgtacca aacgggcaag     60

gacatctcta caaattacta t                                               81
```

<210> SEQ ID NO 34
<211> LENGTH: 147
<212> TYPE: DNA
<213> ORGANISM: Artificial Sequence
<220> FEATURE:
<223> OTHER INFORMATION: Synthetic

<400> SEQUENCE: 34

```
atgagggccc tgtgggtgct gggcctctgc tgcgtcctgc tgaccttcgg gtcggtcaga     60

gcttacggat ggtctggcaa catggagaga atcatgaaag cacaagcgta ccaaacgggc    120

aaggacatct ctacaaatta ctattaa                                        147
```

<210> SEQ ID NO 35
<211> LENGTH: 444
<212> TYPE: DNA
<213> ORGANISM: Artificial Sequence
<220> FEATURE:
<223> OTHER INFORMATION: Synthetic

<400> SEQUENCE: 35

```
tacggatggt ctggcaacat ggagagaatc atgaaagcac aagcgtacca aacgggcaag     60

gacatctcta caaattacta tgcgagtcag aagaaaacat ttgaaattaa tcccagacac    120

ccgctgatca gagacatgct tcgacgaatt aaggaagatg aagatgataa aacagttttg    180

gatcttgctg tggttttgtt tgaaacagca acgcttcggt cagggtatct tttaccagac    240

actaaagcat atggagatag aatagaaaga atgcttcgcc tcagtttgaa cattgaccct    300

gatgcaaagg tggaagaaga gcctgaagaa gaacctgaag agacagcaga agacacaaca    360

gaagacacag agcaagacga agatgaagaa atggatgtgg gaacagatga agaagaagaa    420

acagcaaagg aatctacagc tgaa                                           444
```

<210> SEQ ID NO 36
<211> LENGTH: 510
<212> TYPE: DNA
<213> ORGANISM: Artificial Sequence
<220> FEATURE:
<223> OTHER INFORMATION: Synthetic

<400> SEQUENCE: 36

```
atgagggccc tgtgggtgct gggcctctgc tgcgtcctgc tgaccttcgg gtcggtcaga     60

gcttacggat ggtctggcaa catggagaga atcatgaaag cacaagcgta ccaaacgggc    120

aaggacatct ctacaaatta ctatgcgagt cagaagaaaa catttgaaat taatcccaga    180

cacccgctga tcagagacat gcttcgacga attaaggaag atgaagatga taaaacagtt    240

ttggatcttg ctgtggtttt gtttgaaaca gcaacgcttc ggtcagggta tcttttacca    300

gacactaaag catatggaga tagaatagaa agaatgcttc gcctcagttt gaacattgac    360

cctgatgcaa aggtggaaga agagcctgaa gaagaacctg aagagacagc agaagacaca    420

acagaagaca cagagcaaga cgaagatgaa gaaatggatg tgggaacaga tgaagaagaa    480

gaaacagcaa aggaatctac agctgaataa                                     510
```

<210> SEQ ID NO 37
<211> LENGTH: 108
<212> TYPE: PRT
<213> ORGANISM: Artificial Sequence
<220> FEATURE:
<223> OTHER INFORMATION: Synthetic

<400> SEQUENCE: 37

```
Thr Ala Cys Gly Gly Ala Thr Gly Gly Thr Cys Thr Gly Gly Cys Ala
1               5                   10                  15

Ala Cys Ala Thr Gly Gly Ala Gly Ala Gly Ala Ala Thr Cys Ala Thr
            20                  25                  30

Gly Ala Ala Ala Gly Cys Ala Cys Ala Ala Gly Cys Gly Thr Ala Cys
        35                  40                  45

Cys Ala Ala Ala Cys Gly Gly Gly Cys Ala Ala Gly Gly Ala Cys Ala
    50                  55                  60

Thr Cys Thr Cys Thr Ala Cys Ala Ala Ala Thr Thr Ala Cys Thr Ala
65                  70                  75                  80

Thr Thr Ala Cys Cys Cys Ala Thr Ala Thr Gly Ala Cys Gly Thr Cys
                85                  90                  95

Cys Cys Gly Gly Ala Thr Thr Ala Cys Gly Cys Thr
            100                 105
```

```
<210> SEQ ID NO 38
<211> LENGTH: 99
<212> TYPE: PRT
<213> ORGANISM: Artificial Sequence
<220> FEATURE:
<223> OTHER INFORMATION: Synthetic

<400> SEQUENCE: 38

Thr Ala Cys Gly Gly Ala Thr Gly Gly Thr Cys Thr Gly Gly Cys Ala
1               5                   10                  15

Ala Cys Ala Thr Gly Gly Ala Gly Ala Gly Ala Ala Thr Cys Ala Thr
            20                  25                  30

Gly Ala Ala Ala Gly Cys Ala Cys Ala Ala Gly Cys Gly Thr Ala Cys
        35                  40                  45

Cys Ala Ala Ala Cys Gly Gly Gly Cys Ala Ala Gly Gly Ala Cys Ala
    50                  55                  60

Thr Cys Thr Cys Thr Ala Cys Ala Ala Ala Thr Thr Ala Cys Thr Ala
65                  70                  75                  80

Thr Cys Ala Cys Cys Ala Cys Cys Ala Cys Cys Ala Cys Cys Ala Cys
                85                  90                  95

Cys Ala Cys


<210> SEQ ID NO 39
<211> LENGTH: 126
<212> TYPE: PRT
<213> ORGANISM: Artificial Sequence
<220> FEATURE:
<223> OTHER INFORMATION: Synthetic

<400> SEQUENCE: 39

Thr Ala Cys Gly Gly Ala Thr Gly Gly Thr Cys Thr Gly Gly Cys Ala
1               5                   10                  15

Ala Cys Ala Thr Gly Gly Ala Gly Ala Gly Ala Ala Thr Cys Ala Thr
            20                  25                  30

Gly Ala Ala Ala Gly Cys Ala Cys Ala Ala Gly Cys Gly Thr Ala Cys
        35                  40                  45

Cys Ala Ala Ala Cys Gly Gly Gly Cys Ala Ala Gly Gly Ala Cys Ala
    50                  55                  60

Thr Cys Thr Cys Thr Ala Cys Ala Ala Ala Thr Thr Ala Cys Thr Ala
65                  70                  75                  80

Thr Thr Ala Cys Cys Cys Ala Thr Ala Thr Gly Ala Cys Gly Thr Cys
                85                  90                  95

Cys Cys Gly Gly Ala Thr Thr Ala Cys Gly Cys Thr Cys Ala Cys Cys
            100                 105                 110

Ala Cys Cys Ala Cys Cys Ala Cys Cys Ala Cys Cys Ala Cys
        115                 120                 125


<210> SEQ ID NO 40
<211> LENGTH: 57
<212> TYPE: PRT
<213> ORGANISM: Artificial Sequence
<220> FEATURE:
<223> OTHER INFORMATION: Synthetic

<400> SEQUENCE: 40

Met Arg Ala Leu Trp Val Leu Gly Leu Cys Cys Val Leu Leu Thr Phe
1               5                   10                  15

Gly Ser Val Arg Ala Tyr Gly Trp Ser Gly Asn Met Glu Arg Ile Met
            20                  25                  30
```

```
Lys Ala Gln Ala Tyr Gln Thr Gly Lys Asp Ile Ser Thr Asn Tyr Tyr
        35                  40                  45

Tyr Pro Tyr Asp Val Pro Asp Tyr Ala
    50                  55


<210> SEQ ID NO 41
<211> LENGTH: 189
<212> TYPE: PRT
<213> ORGANISM: Artificial Sequence
<220> FEATURE:
<223> OTHER INFORMATION: Synthetic

<400> SEQUENCE: 41

Ala Thr Gly Ala Gly Gly Gly Cys Cys Cys Thr Gly Thr Gly Gly Gly
1               5                   10                  15

Thr Gly Cys Thr Gly Gly Gly Cys Cys Thr Cys Thr Gly Cys Thr Gly
            20                  25                  30

Cys Gly Thr Cys Cys Thr Gly Cys Thr Gly Ala Cys Cys Thr Thr Cys
        35                  40                  45

Gly Gly Gly Thr Cys Gly Gly Thr Cys Ala Gly Ala Gly Cys Thr Thr
    50                  55                  60

Ala Cys Gly Gly Ala Thr Gly Gly Thr Cys Thr Gly Gly Cys Ala Ala
65                  70                  75                  80

Cys Ala Thr Gly Gly Ala Gly Ala Gly Ala Ala Thr Cys Ala Thr Gly
                85                  90                  95

Ala Ala Ala Gly Cys Ala Cys Ala Ala Gly Cys Gly Thr Ala Cys Cys
            100                 105                 110

Ala Ala Ala Cys Gly Gly Gly Cys Ala Ala Gly Gly Ala Cys Ala Thr
        115                 120                 125

Cys Thr Cys Thr Ala Cys Ala Ala Ala Thr Thr Ala Cys Thr Ala Thr
    130                 135                 140

Thr Ala Cys Cys Cys Ala Thr Ala Thr Gly Ala Cys Gly Thr Cys Cys
145                 150                 155                 160

Cys Gly Gly Ala Thr Thr Ala Cys Gly Cys Thr Cys Ala Cys Cys Ala
                165                 170                 175

Cys Cys Ala Cys Cys Ala Cys Cys Ala Cys Cys Ala Cys
            180                 185


<210> SEQ ID NO 42
<211> LENGTH: 126
<212> TYPE: PRT
<213> ORGANISM: Artificial Sequence
<220> FEATURE:
<223> OTHER INFORMATION: Synthetic

<400> SEQUENCE: 42

Thr Ala Cys Gly Gly Ala Thr Gly Gly Thr Cys Thr Gly Gly Cys Ala
1               5                   10                  15

Ala Cys Ala Thr Gly Gly Ala Gly Ala Gly Ala Ala Thr Cys Ala Thr
            20                  25                  30

Gly Ala Ala Ala Gly Cys Ala Cys Ala Ala Gly Cys Gly Thr Ala Cys
        35                  40                  45

Cys Ala Ala Ala Cys Gly Gly Gly Cys Ala Ala Gly Gly Ala Cys Ala
    50                  55                  60

Thr Cys Thr Cys Thr Ala Cys Ala Ala Ala Thr Thr Ala Cys Thr Ala
65                  70                  75                  80

Thr Thr Ala Cys Cys Cys Ala Thr Ala Thr Gly Ala Cys Gly Thr Cys
                85                  90                  95
```

```
Cys Cys Gly Gly Ala Thr Thr Ala Cys Gly Cys Thr Cys Ala Cys Cys
            100                 105                 110

Ala Cys Cys Ala Cys Cys Ala Cys Cys Ala Cys Cys Ala Cys
        115                 120                 125


<210> SEQ ID NO 43
<211> LENGTH: 157
<212> TYPE: PRT
<213> ORGANISM: Artificial Sequence
<220> FEATURE:
<223> OTHER INFORMATION: Synthetic

<400> SEQUENCE: 43

Tyr Gly Trp Ser Gly Asn Met Glu Arg Ile Met Lys Ala Gln Ala Tyr
1               5                   10                  15

Gln Thr Gly Lys Asp Ile Ser Thr Asn Tyr Tyr Ala Ser Gln Lys Lys
            20                  25                  30

Thr Phe Glu Ile Asn Pro Arg His Pro Leu Ile Arg Asp Met Leu Arg
        35                  40                  45

Arg Ile Lys Glu Asp Glu Asp Asp Lys Thr Val Leu Asp Leu Ala Val
    50                  55                  60

Val Leu Phe Glu Thr Ala Thr Leu Arg Ser Gly Tyr Leu Leu Pro Asp
65                  70                  75                  80

Thr Lys Ala Tyr Gly Asp Arg Ile Glu Arg Met Leu Arg Leu Ser Leu
                85                  90                  95

Asn Ile Asp Pro Asp Ala Lys Val Glu Glu Glu Pro Glu Glu Glu Pro
            100                 105                 110

Glu Glu Thr Ala Glu Asp Thr Thr Glu Asp Thr Glu Gln Asp Glu Asp
        115                 120                 125

Glu Glu Met Asp Val Gly Thr Asp Glu Glu Glu Glu Thr Ala Lys Glu
    130                 135                 140

Ser Thr Ala Glu Tyr Pro Tyr Asp Val Pro Asp Tyr Ala
145                 150                 155


<210> SEQ ID NO 44
<211> LENGTH: 163
<212> TYPE: PRT
<213> ORGANISM: Artificial Sequence
<220> FEATURE:
<223> OTHER INFORMATION: Synthetic

<400> SEQUENCE: 44

Tyr Gly Trp Ser Gly Asn Met Glu Arg Ile Met Lys Ala Gln Ala Tyr
1               5                   10                  15

Gln Thr Gly Lys Asp Ile Ser Thr Asn Tyr Tyr Ala Ser Gln Lys Lys
            20                  25                  30

Thr Phe Glu Ile Asn Pro Arg His Pro Leu Ile Arg Asp Met Leu Arg
        35                  40                  45

Arg Ile Lys Glu Asp Glu Asp Asp Lys Thr Val Leu Asp Leu Ala Val
    50                  55                  60

Val Leu Phe Glu Thr Ala Thr Leu Arg Ser Gly Tyr Leu Leu Pro Asp
65                  70                  75                  80

Thr Lys Ala Tyr Gly Asp Arg Ile Glu Arg Met Leu Arg Leu Ser Leu
                85                  90                  95

Asn Ile Asp Pro Asp Ala Lys Val Glu Glu Glu Pro Glu Glu Glu Pro
            100                 105                 110

Glu Glu Thr Ala Glu Asp Thr Thr Glu Asp Thr Glu Gln Asp Glu Asp
```

```
        115                 120                 125

Glu Glu Met Asp Val Gly Thr Asp Glu Glu Glu Glu Thr Ala Lys Glu
    130                 135                 140

Ser Thr Ala Glu Tyr Pro Tyr Asp Val Pro Asp Tyr Ala His His His
145                 150                 155                 160

His His His


<210> SEQ ID NO 45
<211> LENGTH: 154
<212> TYPE: PRT
<213> ORGANISM: Artificial Sequence
<220> FEATURE:
<223> OTHER INFORMATION: Synthetic

<400> SEQUENCE: 45

Tyr Gly Trp Ser Gly Asn Met Glu Arg Ile Met Lys Ala Gln Ala Tyr
1               5                   10                  15

Gln Thr Gly Lys Asp Ile Ser Thr Asn Tyr Tyr Ala Ser Gln Lys Lys
            20                  25                  30

Thr Phe Glu Ile Asn Pro Arg His Pro Leu Ile Arg Asp Met Leu Arg
        35                  40                  45

Arg Ile Lys Glu Asp Glu Asp Asp Lys Thr Val Leu Asp Leu Ala Val
    50                  55                  60

Val Leu Phe Glu Thr Ala Thr Leu Arg Ser Gly Tyr Leu Leu Pro Asp
65                  70                  75                  80

Thr Lys Ala Tyr Gly Asp Arg Ile Glu Arg Met Leu Arg Leu Ser Leu
                85                  90                  95

Asn Ile Asp Pro Asp Ala Lys Val Glu Glu Glu Pro Glu Glu Glu Pro
            100                 105                 110

Glu Glu Thr Ala Glu Asp Thr Thr Glu Asp Thr Glu Gln Asp Glu Asp
        115                 120                 125

Glu Glu Met Asp Val Gly Thr Asp Glu Glu Glu Glu Thr Ala Lys Glu
    130                 135                 140

Ser Thr Ala Glu His His His His His His
145                 150


<210> SEQ ID NO 46
<211> LENGTH: 178
<212> TYPE: PRT
<213> ORGANISM: Artificial Sequence
<220> FEATURE:
<223> OTHER INFORMATION: Synthetic

<400> SEQUENCE: 46

Met Arg Ala Leu Trp Val Leu Gly Leu Cys Cys Val Leu Leu Thr Phe
1               5                   10                  15

Gly Ser Val Arg Ala Tyr Gly Trp Ser Gly Asn Met Glu Arg Ile Met
            20                  25                  30

Lys Ala Gln Ala Tyr Gln Thr Gly Lys Asp Ile Ser Thr Asn Tyr Tyr
        35                  40                  45

Ala Ser Gln Lys Lys Thr Phe Glu Ile Asn Pro Arg His Pro Leu Ile
    50                  55                  60

Arg Asp Met Leu Arg Arg Ile Lys Glu Asp Glu Asp Asp Lys Thr Val
65                  70                  75                  80

Leu Asp Leu Ala Val Val Leu Phe Glu Thr Ala Thr Leu Arg Ser Gly
                85                  90                  95

Tyr Leu Leu Pro Asp Thr Lys Ala Tyr Gly Asp Arg Ile Glu Arg Met
```

```
            100                 105                 110

Leu Arg Leu Ser Leu Asn Ile Asp Pro Asp Ala Lys Val Glu Glu Glu
        115                 120                 125

Pro Glu Glu Glu Pro Glu Glu Thr Ala Glu Asp Thr Thr Glu Asp Thr
    130                 135                 140

Glu Gln Asp Glu Asp Glu Glu Met Asp Val Gly Thr Asp Glu Glu Glu
145                 150                 155                 160

Glu Thr Ala Lys Glu Ser Thr Ala Glu Tyr Pro Tyr Asp Val Pro Asp
                165                 170                 175

Tyr Ala


<210> SEQ ID NO 47
<211> LENGTH: 184
<212> TYPE: PRT
<213> ORGANISM: Artificial Sequence
<220> FEATURE:
<223> OTHER INFORMATION: Synthetic

<400> SEQUENCE: 47

Met Arg Ala Leu Trp Val Leu Gly Leu Cys Cys Val Leu Leu Thr Phe
1               5                   10                  15

Gly Ser Val Arg Ala Tyr Gly Trp Ser Gly Asn Met Glu Arg Ile Met
            20                  25                  30

Lys Ala Gln Ala Tyr Gln Thr Gly Lys Asp Ile Ser Thr Asn Tyr Tyr
        35                  40                  45

Ala Ser Gln Lys Lys Thr Phe Glu Ile Asn Pro Arg His Pro Leu Ile
    50                  55                  60

Arg Asp Met Leu Arg Arg Ile Lys Glu Asp Glu Asp Asp Lys Thr Val
65                  70                  75                  80

Leu Asp Leu Ala Val Val Leu Phe Glu Thr Ala Thr Leu Arg Ser Gly
                85                  90                  95

Tyr Leu Leu Pro Asp Thr Lys Ala Tyr Gly Asp Arg Ile Glu Arg Met
            100                 105                 110

Leu Arg Leu Ser Leu Asn Ile Asp Pro Asp Ala Lys Val Glu Glu Glu
        115                 120                 125

Pro Glu Glu Glu Pro Glu Glu Thr Ala Glu Asp Thr Thr Glu Asp Thr
    130                 135                 140

Glu Gln Asp Glu Asp Glu Glu Met Asp Val Gly Thr Asp Glu Glu Glu
145                 150                 155                 160

Glu Thr Ala Lys Glu Ser Thr Ala Glu Tyr Pro Tyr Asp Val Pro Asp
                165                 170                 175

Tyr Ala His His His His His His
            180


<210> SEQ ID NO 48
<211> LENGTH: 175
<212> TYPE: PRT
<213> ORGANISM: Artificial Sequence
<220> FEATURE:
<223> OTHER INFORMATION: Synthetic

<400> SEQUENCE: 48

Met Arg Ala Leu Trp Val Leu Gly Leu Cys Cys Val Leu Leu Thr Phe
1               5                   10                  15

Gly Ser Val Arg Ala Tyr Gly Trp Ser Gly Asn Met Glu Arg Ile Met
            20                  25                  30

Lys Ala Gln Ala Tyr Gln Thr Gly Lys Asp Ile Ser Thr Asn Tyr Tyr
```

```
        35                  40                  45

Ala Ser Gln Lys Lys Thr Phe Glu Ile Asn Pro Arg His Pro Leu Ile
    50                  55                  60

Arg Asp Met Leu Arg Arg Ile Lys Glu Asp Glu Asp Asp Lys Thr Val
65                  70                  75                  80

Leu Asp Leu Ala Val Val Leu Phe Glu Thr Ala Thr Leu Arg Ser Gly
                85                  90                  95

Tyr Leu Leu Pro Asp Thr Lys Ala Tyr Gly Asp Arg Ile Glu Arg Met
            100                 105                 110

Leu Arg Leu Ser Leu Asn Ile Asp Pro Asp Ala Lys Val Glu Glu Glu
        115                 120                 125

Pro Glu Glu Glu Pro Glu Glu Thr Ala Glu Asp Thr Thr Glu Asp Thr
    130                 135                 140

Glu Gln Asp Glu Asp Glu Glu Met Asp Val Gly Thr Asp Glu Glu Glu
145                 150                 155                 160

Glu Thr Ala Lys Glu Ser Thr Ala Glu His His His His His His
                165                 170                 175
```

<210> SEQ ID NO 49
<211> LENGTH: 489
<212> TYPE: DNA
<213> ORGANISM: Artificial Sequence
<220> FEATURE:
<223> OTHER INFORMATION: Synthetic

<400> SEQUENCE: 49

```
tacggatggt ctggcaacat ggagagaatc atgaaagcac aagcgtacca aacgggcaag      60

gacatctcta caaattacta tgcgagtcag aagaaaacat ttgaaattaa tcccagacac     120

ccgctgatca gagacatgct tcgacgaatt aaggaagatg aagatgataa aacagttttg     180

gatcttgctg tggttttgtt tgaaacagca acgcttcggt cagggtatct tttaccagac     240

actaaagcat atggagatag aatagaaaga atgcttcgcc tcagtttgaa cattgaccct     300

gatgcaaagg tggaagaaga gcctgaagaa gaacctgaag agacagcaga agacacaaca     360

gaagacacag agcaagacga agatgaagaa atggatgtgg gaacagatga agaagaagaa     420

acagcaaagg aatctacagc tgaataccca tatgacgtcc cggattacgc tcaccaccac     480

caccaccac                                                             489
```

<210> SEQ ID NO 50
<211> LENGTH: 116
<212> TYPE: DNA
<213> ORGANISM: Artificial Sequence
<220> FEATURE:
<223> OTHER INFORMATION: Synthetic

<400> SEQUENCE: 50

```
atggctagct acggatggtc tggcaacatg gagagaatca tgaaagcaca agcgtaccaa      60

acgggcaagg acatctctac aaattactat tcgagcacca ccaccaccac cactaa         116
```

<210> SEQ ID NO 51
<211> LENGTH: 126
<212> TYPE: DNA
<213> ORGANISM: Artificial Sequence
<220> FEATURE:
<223> OTHER INFORMATION: Synthetic

<400> SEQUENCE: 51

```
tacggatggt ctggcaacat ggagagaatc atgaaagcac aagcgtacca aacgggcaag      60
```

```
gacatctcta caaattacta ttacccatat gacgtcccgg attacgctca ccaccaccac    120

caccac                                                                126


<210> SEQ ID NO 52
<211> LENGTH: 189
<212> TYPE: DNA
<213> ORGANISM: Artificial Sequence
<220> FEATURE:
<223> OTHER INFORMATION: Synthetic

<400> SEQUENCE: 52

atgagggccc tgtgggtgct gggcctctgc tgcgtcctgc tgaccttcgg gtcggtcaga     60

gcttacggat ggtctggcaa catggagaga atcatgaaag cacaagcgta ccaaacgggc    120

aaggacatct ctacaaatta ctattaccca tatgacgtcc cggattacgc tcaccaccac    180

caccaccac                                                             189


<210> SEQ ID NO 53
<211> LENGTH: 189
<212> TYPE: DNA
<213> ORGANISM: Artificial Sequence
<220> FEATURE:
<223> OTHER INFORMATION: Synthetic

<400> SEQUENCE: 53

atgagggccc tgtgggtgct gggcctctgc tgcgtcctgc tgaccttcgg gtcggtcaga     60

gcttacggat ggtctggcaa catggagaga atcatgaaag cacaagcgta ccaaacgggc    120

aaggacatct ctacaaatta ctattaccca tatgacgtcc cggattacgc tcaccaccac    180

caccaccac                                                             189


<210> SEQ ID NO 54
<211> LENGTH: 462
<212> TYPE: DNA
<213> ORGANISM: Artificial Sequence
<220> FEATURE:
<223> OTHER INFORMATION: Synthetic

<400> SEQUENCE: 54

tacggatggt ctggcaacat ggagagaatc atgaaagcac aagcgtacca aacgggcaag     60

gacatctcta caaattacta tgcgagtcag aagaaaacat ttgaaattaa tcccagacac    120

ccgctgatca gagacatgct tcgacgaatt aaggaagatg aagatgataa aacagttttg    180

gatcttgctg tggttttgtt tgaaacagca acgcttcggt cagggtatct tttaccagac    240

actaaagcat atggagatag aatagaaaga atgcttcgcc tcagtttgaa cattgaccct    300

gatgcaaagg tggaagaaga gcctgaagaa gaacctgaag agacagcaga agacacaaca    360

gaagacacag agcaagacga agatgaagaa atggatgtgg gaacagatga agaagaagaa    420

acagcaaagg aatctacagc tgaacaccac caccaccacc ac                        462


<210> SEQ ID NO 55
<211> LENGTH: 471
<212> TYPE: DNA
<213> ORGANISM: Artificial Sequence
<220> FEATURE:
<223> OTHER INFORMATION: Synthetic

<400> SEQUENCE: 55

tacggatggt ctggcaacat ggagagaatc atgaaagcac aagcgtacca aacgggcaag     60
```

```
gacatctcta caaattacta tgcgagtcag aagaaaacat ttgaaattaa tcccagacac    120

ccgctgatca gagacatgct tcgacgaatt aaggaagatg aagatgataa aacagttttg    180

gatcttgctg tggttttgtt tgaaacagca acgcttcggt cagggtatct tttaccagac    240

actaaagcat atggagatag aatagaaaga atgcttcgcc tcagtttgaa cattgaccct    300

gatgcaaagg tggaagaaga gcctgaagaa gaacctgaag agacagcaga agacacaaca    360

gaagacacag agcaagacga agatgaagaa atggatgtgg gaacagatga agaagaagaa    420

acagcaaagg aatctacagc tgaataccca tatgacgtcc cggattacgc t             471
```

```
<210> SEQ ID NO 56
<211> LENGTH: 507
<212> TYPE: DNA
<213> ORGANISM: Artificial Sequence
<220> FEATURE:
<223> OTHER INFORMATION: Synthetic

<400> SEQUENCE: 56

atggctagct acggatggtc tggcaacatg gagagaatca tgaaagcaca agcgtaccaa     60

acgggcaagg acatctctac aaattactat gcgagtcaga agaaaacatt tgaaattaat    120

cccagacacc cgctgatcag agacatgctt cgacgaatta aggaagatga agatgataaa    180

acagttttgg atcttgctgt ggttttgttt gaaacagcaa cgcttcggtc agggtatctt    240

ttaccagaca ctaaagcata tggagataga atagaaagaa tgcttcgcct cagtttgaac    300

attgaccctg atgcaaaggt ggaagaagag cctgaagaag aacctgaaga gacagcagaa    360

gacacaacag aagacacaga gcaagacgaa gatgaagaaa tggatgtggg aacagatgaa    420

gaagaagaaa cagcaaagga atctacagct gaatacccat atgacgtccc ggattacgct    480

ctcgagcacc accaccacca ccactaa                                         507
```

```
<210> SEQ ID NO 57
<211> LENGTH: 479
<212> TYPE: DNA
<213> ORGANISM: Artificial Sequence
<220> FEATURE:
<223> OTHER INFORMATION: Synthetic

<400> SEQUENCE: 57

atggctagct acggatggtc tggcaacatg gagagaatca tgaaagcaca agcgtaccaa     60

acgggcaagg acatctctac aaattactat gcgagtcaga agaaaacatt tgaaattaat    120

cccagacacc cgctgatcag agacatgctt cgacgaatta aggaagatga agatgataaa    180

acagttttgg atcttgctgt ggttttgttt gaaacagcaa cgcttcggtc agggtatctt    240

ttaccagaca ctaaagcata tggagataga atagaaagaa tgcttcgcct cagtttgaac    300

attgaccctg atgcaaaggt ggaagaagag cctgaagaag aacctgaaga gacagcagaa    360

gacacaacag aagacacaga gcaagacgaa gatgaagaaa tggatgtggg aacagatgaa    420

gaagaagaaa cagcaaagga atctacagct gaatcgagca ccaccaccac caccactaa     479
```

```
<210> SEQ ID NO 58
<211> LENGTH: 537
<212> TYPE: DNA
<213> ORGANISM: Artificial Sequence
<220> FEATURE:
<223> OTHER INFORMATION: Synthetic

<400> SEQUENCE: 58

atgagggccc tgtgggtgct gggcctctgc tgcgtcctgc tgaccttcgg gtcggtcaga     60
```

```
gcttacggat ggtctggcaa catggagaga atcatgaaag cacaagcgta ccaaacgggc    120

aaggacatct ctacaaatta ctatgcgagt cagaagaaaa catttgaaat taatcccaga    180

cacccgctga tcagagacat gcttcgacga attaaggaag atgaagatga taaaacagtt    240

ttggatcttg ctgtggtttt gtttgaaaca gcaacgcttc ggtcagggta tcttttacca    300

gacactaaag catatggaga tagaatagaa agaatgcttc gcctcagttt gaacattgac    360

cctgatgcaa aggtggaaga agagcctgaa gaagaacctg aagagacagc agaagacaca    420

acagaagaca cagagcaaga cgaagatgaa gaaatggatg tgggaacaga tgaagaagaa    480

gaaacagcaa aggaatctac agctgaatac ccatatgacg tcccggatta cgcttaa       537
```

<210> SEQ ID NO 59
<211> LENGTH: 552
<212> TYPE: DNA
<213> ORGANISM: Artificial Sequence
<220> FEATURE:
<223> OTHER INFORMATION: Synthetic

<400> SEQUENCE: 59

```
atgagggccc tgtgggtgct gggcctctgc tgcgtcctgc tgaccttcgg gtcggtcaga     60

gcttacggat ggtctggcaa catggagaga atcatgaaag cacaagcgta ccaaacgggc    120

aaggacatct ctacaaatta ctatgcgagt cagaagaaaa catttgaaat taatcccaga    180

cacccgctga tcagagacat gcttcgacga attaaggaag atgaagatga taaaacagtt    240

ttggatcttg ctgtggtttt gtttgaaaca gcaacgcttc ggtcagggta tcttttacca    300

gacactaaag catatggaga tagaatagaa agaatgcttc gcctcagttt gaacattgac    360

cctgatgcaa aggtggaaga agagcctgaa gaagaacctg aagagacagc agaagacaca    420

acagaagaca cagagcaaga cgaagatgaa gaaatggatg tgggaacaga tgaagaagaa    480

gaaacagcaa aggaatctac agctgaatac ccatatgacg tcccggatta cgctcaccac    540

caccaccacc ac                                                        552
```

<210> SEQ ID NO 60
<211> LENGTH: 525
<212> TYPE: DNA
<213> ORGANISM: Artificial Sequence
<220> FEATURE:
<223> OTHER INFORMATION: Synthetic

<400> SEQUENCE: 60

```
atgagggccc tgtgggtgct gggcctctgc tgcgtcctgc tgaccttcgg gtcggtcaga     60

gcttacggat ggtctggcaa catggagaga atcatgaaag cacaagcgta ccaaacgggc    120

aaggacatct ctacaaatta ctatgcgagt cagaagaaaa catttgaaat taatcccaga    180

cacccgctga tcagagacat gcttcgacga attaaggaag atgaagatga taaaacagtt    240

ttggatcttg ctgtggtttt gtttgaaaca gcaacgcttc ggtcagggta tcttttacca    300

gacactaaag catatggaga tagaatagaa agaatgcttc gcctcagttt gaacattgac    360

cctgatgcaa aggtggaaga agagcctgaa gaagaacctg aagagacagc agaagacaca    420

acagaagaca cagagcaaga cgaagatgaa gaaatggatg tgggaacaga tgaagaagaa    480

gaaacagcaa aggaatctac agctgaacac caccaccacc accac                    525
```

<210> SEQ ID NO 61
<211> LENGTH: 134
<212> TYPE: PRT

<213> ORGANISM: Homo Sapiens

<400> SEQUENCE: 61

```
Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130
```

<210> SEQ ID NO 62
<211> LENGTH: 126
<212> TYPE: PRT
<213> ORGANISM: Homo Sapiens

<400> SEQUENCE: 62

```
Met His Leu Ser Gln Leu Leu Ala Cys Ala Leu Leu Leu Thr Leu Leu
1               5                   10                  15

Ser Leu Arg Pro Ser Glu Ala Lys Pro Gly Ala Pro Pro Lys Val Pro
            20                  25                  30

Arg Thr Pro Pro Ala Glu Glu Leu Ala Glu Pro Gln Ala Ala Gly Gly
        35                  40                  45

Gly Gln Lys Lys Gly Asp Lys Ala Pro Gly Gly Gly Gly Ala Asn Leu
    50                  55                  60

Lys Gly Asp Arg Ser Arg Leu Leu Arg Asp Leu Arg Val Asp Thr Lys
65                  70                  75                  80

Ser Arg Ala Ala Trp Ala Arg Leu Leu Gln Glu His Pro Asn Ala Arg
                85                  90                  95

Lys Tyr Lys Gly Ala Asn Lys Lys Gly Leu Ser Lys Gly Cys Phe Gly
            100                 105                 110

Leu Lys Leu Asp Arg Ile Gly Ser Met Ser Gly Leu Gly Cys
        115                 120                 125
```

<210> SEQ ID NO 63
<211> LENGTH: 153
<212> TYPE: PRT
<213> ORGANISM: Homo Sapiens

<400> SEQUENCE: 63

```
Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45
```

```
Glu Lys Met Pro Leu Glu Asp Glu Val Val Pro Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr Arg Arg
145                 150


<210> SEQ ID NO 64
<211> LENGTH: 808
<212> TYPE: PRT
<213> ORGANISM: Homo Sapiens

<400> SEQUENCE: 64

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
```

```
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Glu Ala Ala Lys Glu Glu Lys Glu
    290                 295                 300

Glu Ser Asp Asp Glu Ala Ala Val Glu Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Ala Ala Ser Ala
                645                 650                 655

Ala Ala Ala Ala Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685
```

```
Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Glu Pro Glu Glu Glu Pro Glu Glu Thr Ala Glu
        755                 760                 765

Asp Thr Thr Glu Asp Thr Glu Gln Asp Glu Asp Glu Glu Met Asp Val
    770                 775                 780

Gly Thr Asp Glu Glu Glu Glu Thr Ala Lys Glu Ser Thr Ala Glu Tyr
785                 790                 795                 800

Pro Tyr Asp Val Pro Asp Tyr Ala
                805


<210> SEQ ID NO 65
<211> LENGTH: 808
<212> TYPE: PRT
<213> ORGANISM: Homo Sapiens

<400> SEQUENCE: 65

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
```

```
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Glu Ala Ala Lys Glu Glu Lys Glu
    290                 295                 300

Glu Ser Asp Asp Glu Ala Ala Val Glu Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Ala Thr Gly Lys Ala
            660                 665                 670
```

```
Ile Ser Thr Asn Ala Ala Ala Ser Gln Lys Lys Thr Phe Glu Ile Asn
        675                 680                 685

Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Glu Pro Glu Glu Glu Pro Glu Glu Thr Ala Glu
        755                 760                 765

Asp Thr Thr Glu Asp Thr Glu Gln Asp Glu Asp Glu Glu Met Asp Val
    770                 775                 780

Gly Thr Asp Glu Glu Glu Glu Thr Ala Lys Glu Ser Thr Ala Glu Tyr
785                 790                 795                 800

Pro Tyr Asp Val Pro Asp Tyr Ala
                805


<210> SEQ ID NO 66
<211> LENGTH: 808
<212> TYPE: PRT
<213> ORGANISM: Artificial Sequence
<220> FEATURE:
<223> OTHER INFORMATION: Synthetic

<400> SEQUENCE: 66

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220
```

```
Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Glu Ala Ala Lys Glu Glu Lys Glu
    290                 295                 300

Glu Ser Asp Asp Glu Ala Ala Val Glu Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620

Lys Ala Leu Lys Asp Lys Ile Glu Lys Ala Val Val Ser Gln Arg Leu
625                 630                 635                 640
```

```
Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685

Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Glu Pro Glu Glu Glu Pro Glu Glu Thr Ala Glu
        755                 760                 765

Asp Thr Thr Glu Asp Thr Glu Gln Asp Glu Asp Glu Glu Met Asp Val
    770                 775                 780

Gly Thr Asp Glu Glu Glu Glu Thr Ala Lys Glu Ser Thr Ala Glu Tyr
785                 790                 795                 800

Pro Tyr Asp Val Pro Asp Tyr Ala
                805


<210> SEQ ID NO 67
<211> LENGTH: 799
<212> TYPE: PRT
<213> ORGANISM: Homo Sapiens

<400> SEQUENCE: 67

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205
```

```
Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Glu Ala Ala Lys Glu Glu Lys Glu
    290                 295                 300

Glu Ser Asp Asp Glu Ala Ala Val Glu Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620
```

```
Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685

Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Glu Pro Glu Glu Glu Pro Glu Glu Thr Ala Glu
        755                 760                 765

Asp Thr Thr Glu Asp Thr Glu Gln Asp Glu Asp Glu Glu Met Asp Val
    770                 775                 780

Gly Thr Asp Glu Glu Glu Glu Thr Ala Lys Glu Ser Thr Ala Glu
785                 790                 795


<210> SEQ ID NO 68
<211> LENGTH: 2799
<212> TYPE: DNA
<213> ORGANISM: Artificial Sequence
<220> FEATURE:
<223> OTHER INFORMATION: Synthetic

<400> SEQUENCE: 68

atgggcaccg tcagctccag gcggtcctgg tggccgctgc cactgctgct gctgctgctg      60

ctgctcctgg gtcccgcggg cgcccgtgcg caggaggacg aggacggcga ctacgaggag     120

ctggtgctag ccttgcgttc cgaggaggac ggcctggccg aagcacccga gcacggaacc     180

acagccacct tccaccgctg cgccaaggat ccgtggaggt tgcctggcac ctacgtggtg     240

gtgctgaagg aggagaccca cctctcgcag tcagagcgca ctgcccgccg cctgcaggcc     300

caggctgccc gccggggata cctcaccaag atcctgcatg tcttccatgg ccttcttcct     360

ggcttcctgg tgaagatgag tggcgacctg ctggagctgg ccttgaagtt gccccatgtc     420

gactacatcg aggaggactc ctctgtcttt gcccagagca tcccgtggaa cctggagcgg     480

attacccctc cacggtaccg ggcggatgaa taccagcccc ccgacggagg cagcctggtg     540

gaggtgtatc tcctagacac cagcatacag agtgaccacc gggaaatcga gggcagggtc     600

atggtcaccg acttcgagaa tgtgcccgag gaggacggga cccgcttcca cagacaggcc     660

agcaagtgtg acagtcatgg cacccacctg gcaggggtgg tcagcggccg ggatgccggc     720

gtggccaagg gtgccagcat gcgcagcctg cgcgtgctca actgccaagg gaagggcacg     780

gttagcggca ccctcatagg cctggagttt attcggaaaa gccagctggt ccagcctgtg     840

gggccactgg tggtgctgct gcccctggcg ggtgggtaca gccgcgtcct caacgccgcc     900

tgccagcgcc tggcgagggc tggggtcgtg ctggtcaccg ctgccggcaa cttccgagac     960

gatgcctgcc tctactcccc agcctcagct cccgaggtca tcacagttgg ggccaccaat    1020

gcccaggacc agccggtgac cctggggact ttggggacca actttggccg ctgtgtggac    1080
```

```
ctctttgccc caggggagga catcattggt gcctccagcg actgcagcac ctgctttgtg   1140

tcacagagtg ggacatcaca ggctgctgcc cacgtggctg gcattgcagc catgatgctg   1200

tctgccgagc cggagctcac cctggccgag ttgaggcaga gactgatcca cttctctgcc   1260

aaagatgtca tcaatgaggc ctggttccct gaggaccagc gggtactgac ccccaacctg   1320

gtggccgccc tgccccccag cacccatggg gcaggttggc agctgttttg caggactgtg   1380

tggtcagcac actcggggcc tacacggatg gccacagcca tcgcccgctg cgccccagat   1440

gaggagctgc tgagctgctc cagtttctcc aggagtggga agcggcgggg cgagcgcatg   1500

gaggcccaag gggcaagct ggtctgccgg gcccacaacg cttttggggg tgagggtgtc   1560

tacgccattg ccaggtgctg cctgctaccc caggccaact gcagcgtcca cacagctcca   1620

ccagctgagg ccagcatggg gacccgtgtc cactgccacc aacagggcca cgtcctcaca   1680

ggctgcagct cccactggga ggtggaggac cttggcaccc acaagccgcc tgtgctgagg   1740

ccacgaggtc agcccaacca gtgcgtgggc cacagggagg ccagcatcca cgcttcctgc   1800

tgccatgccc caggtctgga atgcaaagtc aaggagcatg gaatcccggc ccctcaggag   1860

caggtgaccg tggcctgcga ggagggctgg accctgactg gctgcagtgc cctccctggg   1920

acctcccacg tcctgggggc ctacgccgta gacaacacgt gtgtagtcag gagccgggac   1980

gtcagcacta caggcagcac cagcgaagag gccgtgacag ccgttgccat ctgctgccgg   2040

agccggcacc tggcgcaggc ctcccaggag ctacagaccg gtcgccacat ggtgagcaag   2100

ggcgaggagg ataacatggc catcatcaag gagttcatgc gcttcaaggt gcacatggag   2160

ggctccgtga acggccacga gttcgagatc gagggcgagg gcgagggccg cccctacgag   2220

ggcacccaga ccgccaagct gaaggtgacc aagggtggcc ccctgccctt cgcctgggac   2280

atcctgtccc ctcagttcat gtacggctcc aaggcctacg tgaagcaccc cgccgacatc   2340

cccgactact tgaagctgtc cttccccgag ggcttcaagt gggagcgcgt gatgaacttc   2400

gaggacggcg gcgtggtgac cgtgacccag gactcctccc tgcaggacgg cgagttcatc   2460

tacaaggtga agctgcgcgg caccaacttc ccctccgacg gccccgtaat gcagaagaag   2520

accatgggct gggaggcctc ctccgagcgg atgtaccccg aggacggcgc cctgaagggc   2580

gagatcaagc agaggctgaa gctgaaggac ggcggccact acgacgctga ggtcaagacc   2640

acctacaagg ccaagaagcc cgtgcagctg cccggcgcct acaacgtcaa catcaagttg   2700

gacatcacct cccacaacga ggactacacc atcgtggaac agtacgaacg cgccgagggc   2760

cgccactcca ccggcggcat ggacgagctg tacaagtaa                          2799
```

<210> SEQ ID NO 69
<211> LENGTH: 7267
<212> TYPE: DNA
<213> ORGANISM: Artificial Sequence
<220> FEATURE:
<223> OTHER INFORMATION: Synthetic

<400> SEQUENCE: 69

```
cccattgacg caaatgggcg gtaggcgtgt acggtgggag gtctatataa gcagagctgg     60

tttagtgaac cgtcagatcc gctagcctcg agaattcatg atcagcttaa tacacaatgg    120

ggccctgggg ctggaaattg cgctggaccg tcgccttgct cctcgccgcg gcggggactg    180

cagtgggcga cagatgtgaa agaaacgagt tccagtgcca agacgggaaa tgcatctcct    240

acaagtgggt ctgcgatggc agcgctgagt gccaggatgg ctctgatgag tcccaggaga    300

cgtgcttgtc tgtcacctgc aaatccgggg acttcagctg tgggggccgt gtcaaccgct    360
```

```
gcattcctca gttctggagg tgcgatggcc aagtggactg cgacaacggc tcagacgagc    420
aaggctgtcc ccccaagacg tgctcccagg acgagtttcg ctgccacgat gggaagtgca    480
tctctcggca gttcgtctgt gactcagacc gggactgctt ggacggctca gacgaggcct    540
cctgcccggt gctcacctgt ggtcccgcca gcttccagtg caacagctcc acctgcatcc    600
cccagctgtg ggcctgcgac aacgaccccg actgcgaaga tggctcggat gagtggccgc    660
agcgctgtag gggtctttac gtgttccaag ggacagtag cccctgctcg gccttcgagt    720
tccactgcct aagtggcgag tgcatccact ccagctggcg ctgtgatggt ggccccgact    780
gcaaggacaa atctgacgag gaaaactgcg ctgtggccac ctgtcgccct gacgaattcc    840
agtgctctga tggaaactgc atccatggca gccggcagtg tgaccgggaa tatgactgca    900
aggacatgag cgatgaagtt ggctgcgtta atgtgacact ctgcgaggga cccaacaagt    960
tcaagtgtca cagcggcgaa tgcatcaccc tggacaaagt ctgcaacatg gctagagact   1020
gccgggactg gtcagatgaa cccatcaaag agtgcgggac caacgaatgc ttggacaaca   1080
acggcggctg ttcccacgtc tgcaatgacc ttaagatcgg ctacgagtgc ctgtgccccg   1140
acggcttcca gctggtggcc cagcgaagat gcgaagatat cgatgagtgt caggatcccg   1200
acacctgcag ccagctctgc gtgaacctgg agggtggcta caagtgccag tgtgaggaag   1260
gcttccagct ggacccccac acgaaggcct gcaaggctgt gggctccatc gcctacctct   1320
tcttcaccaa ccggcacgag gtcaggaaga tgacgctgga ccggagcgag tacaccagcc   1380
tcatccccaa cctgaggaac gtggtcgctc tggacacgga ggtggccagc aatagaatct   1440
actggtctga cctgtcccag agaatgatct gcagcaccca gcttgacaga gcccacggcg   1500
tctcttccta tgacaccgtc atcagcaggg acatccaggc ccccgacggg ctggctgtgg   1560
actggatcca cagcaacatc tactggaccg actctgtcct gggcactgtc tctgttgcgg   1620
ataccaaggg cgtgaagagg aaaacgttat tcagggagaa cggctccaag ccaagggcca   1680
tcgtggtgga tcctgttcat ggcttcatgt actggactga ctggggaact cccgccaaga   1740
tcaagaaagg gggcctgaat ggtgtggaca tctactcgct ggtgactgaa aacattcagt   1800
ggcccaatgg catcacccta gatctcctca gtggccgcct ctactgggtt gactccaaac   1860
ttcactccat ctcaagcatc gatgtcaatg gggcaaccg gaagaccatc ttggaggatg   1920
aaaagaggct ggcccacccc ttctccttgg ccgtctttga ggacaaagta ttttggacag   1980
atatcatcaa cgaagccatt ttcagtgcca accgcctcac aggttccgat gtcaacttgt   2040
tggctgaaaa cctactgtcc ccagaggata tggtcctctt ccacaacctc acccagccaa   2100
gaggagtgaa ctggtgtgag aggaccaccc tgagcaatgg cggctgccag tatctgtgcc   2160
tccctgcccc gcagatcaac ccccactcgc ccaagtttac ctgcgcctgc ccggacggca   2220
tgctgctggc cagggacatg aggagctgcc tcacagaggc tgaggctgca gtggccaccc   2280
aggagacatc caccgtcagg ctaaaggtca gctccacagc cgtaaggaca cagcacacaa   2340
ccacccggcc tgttcccgac acctcccggc tgcctggggc cacccctggg ctcaccacgg   2400
tggagatagt gacaatgtct caccaagctc tgggcgacgt tgctggcaga ggaaatgaga   2460
agaagcccag tagcgtgagg gctctgtcca ttgtcctccc catcgtgctc ctcgtcttcc   2520
tttgcctggg ggtcttcctt ctatggaaga actggcggct taagaacatc aacagcatca   2580
actttgacaa ccccgtctat cagaagacca cagaggatga ggtccacatt tgccacaacc   2640
aggacggcta cagctacccc tcgagacaga tggtcagtct ggaggatgac gtggcgaccg   2700
```

```
gtatggtgag caagggcgag gagctgttca ccggggtggt gcccatcctg gtcgagctgg   2760
acggcgacgt aaacggccac aagttcagcg tgtccggcga gggcgagggc gatgccacct   2820
acggcaagct gaccctgaag ttcatctgca ccaccggcaa gctgcccgtg ccctggccca   2880
ccctcgtgac caccctgacc tacggcgtgc agtgcttcag ccgctacccc gaccacatga   2940
agcagcacga cttcttcaag tccgccatgc ccgaaggcta cgtccaggag cgcaccatct   3000
tcttcaagga cgacggcaac tacaagaccc gcgccgaggt gaagttcgag ggcgacaccc   3060
tggtgaaccg catcgagctg aagggcatcg acttcaagga ggacggcaac atcctggggc   3120
acaagctgga gtacaactac aacagccaca acgtctatat catggccgac aagcagaaga   3180
acggcatcaa ggtgaacttc aagatccgcc acaacatcga ggacggcagc gtgcagctcg   3240
ccgaccacta ccagcagaac acccccatcg gcgacggccc cgtgctgctg cccgacaacc   3300
actacctgag cacccagtcc gccctgagca aagaccccaa cgagaagcgc gatcacatgg   3360
tcctgctgga gttcgtgacc gccgccggga tcactctcgg catggacgag ctgtacaagt   3420
aaagcggccg cgactctaga tcataatcag ccataccaca tttgtagagg ttttacttgc   3480
tttaaaaaac ctcccacacc tccccctgaa cctgaaacat aaaatgaatg caattgttgt   3540
tgttaacttg tttattgcag cttataatgg ttacaaataa agcaatagca tcacaaattt   3600
cacaaataaa gcattttttt cactgcattc tagttgtggt ttgtccaaac tcatcaatgt   3660
atcttaaggc gtaaattgta agcgttaata ttttgttaaa attcgcgtta aatttttgtt   3720
aaatcagctc attttttaac caataggccg aaatcggcaa aatcccttat aaatcaaaag   3780
aatagaccga gatagggttg agtgttgttc cagtttggaa caagagtcca ctattaaaga   3840
acgtggactc caacgtcaaa gggcgaaaaa ccgtctatca gggcgatggc ccactacgtg   3900
aaccatcacc ctaatcaagt tttttggggt cgaggtgccg taaagcacta aatcggaacc   3960
ctaaagggag cccccgattt agagcttgac ggggaaagcc ggcgaacgtg gcgagaaagg   4020
aagggaagaa agcgaaagga gcgggcgcta gggcgctggc aagtgtagcg gtcacgctgc   4080
gcgtaaccac cacacccgcc gcgcttaatg cgccgctaca gggcgcgtca ggtggcactt   4140
ttcggggaaa tgtgcgcgga acccctattt gtttattttt ctaaatacat tcaaatatgt   4200
atccgctcat gagacaataa ccctgataaa tgcttcaata atattgaaaa aggaagagtc   4260
ctgaggcgga aagaaccagc tgtggaatgt gtgtcagtta gggtgtggaa agtccccagg   4320
ctccccagca ggcagaagta tgcaaagcat gcatctcaat tagtcagcaa ccaggtgtgg   4380
aaagtcccca ggctccccag caggcagaag tatgcaaagc atgcatctca attagtcagc   4440
aaccatagtc ccgcccctaa ctccgcccat cccgccccta actccgccca gttccgccca   4500
ttctccgccc catggctgac taattttttt tatttatgca gaggccgagg ccgcctcggc   4560
ctctgagcta ttccagaagt agtgaggagg cttttttgga ggcctaggct tttgcaaaga   4620
tcgatcaaga gacaggatga ggatcgtttc gcatgattga acaagatgga ttgcacgcag   4680
gttctccggc cgcttgggtg gagaggctat tcggctatga ctgggcacaa cagacaatcg   4740
gctgctctga tgccgccgtg ttccggctgt cagcgcaggg gcgcccggtt ctttttgtca   4800
agaccgacct gtccggtgcc ctgaatgaac tgcaagacga ggcagcgcgg ctatcgtggc   4860
tggccacgac gggcgttcct tgcgcagctg tgctcgacgt tgtcactgaa gcgggaaggg   4920
actggctgct attgggcgaa gtgccggggc aggatctcct gtcatctcac cttgctcctg   4980
ccgagaaagt atccatcatg gctgatgcaa tgcggcggct gcatacgctt gatccggcta   5040
cctgcccatt cgaccaccaa gcgaaacatc gcatcgagcg agcacgtact cggatggaag   5100
```

```
ccggtcttgt cgatcaggat gatctggacg aagagcatca ggggctcgcg ccagccgaac   5160
tgttcgccag gctcaaggcg agcatgcccg acggcgagga tctcgtcgtg acccatggcg   5220
atgcctgctt gccgaatatc atggtggaaa atggccgctt ttctggattc atcgactgtg   5280
gccggctggg tgtggcggac cgctatcagg acatagcgtt ggctacccgt gatattgctg   5340
aagagcttgg cggcgaatgg gctgaccgct tcctcgtgct ttacggtatc gccgctcccg   5400
attcgcagcg catcgccttc tatcgccttc ttgacgagtt cttctgagcg ggactctggg   5460
gttcgaaatg accgaccaag cgacgcccaa cctgccatca cgagatttcg attccaccgc   5520
cgccttctat gaaaggttgg gcttcggaat cgttttccgg gacgccggct ggatgatcct   5580
ccagcgcggg gatctcatgc tggagttctt cgcccaccct aggggggaggc taactgaaac   5640
acggaaggag acaataccgg aaggaacccg cgctatgacg gcaataaaaa gacagaataa   5700
aacgcacggt gttgggtcgt ttgttcataa acgcggggtt cggtcccagg gctggcactc   5760
tgtcgatacc ccaccgagac cccattgggg ccaatacgcc cgcgtttctt ccttttcccc   5820
accccacccc ccaagttcgg gtgaaggccc agggctcgca gccaacgtcg gggcggcagg   5880
ccctgccata gcctcaggtt actcatatat actttagatt gatttaaaac ttcattttta   5940
atttaaaagg atctaggtga agatcctttt tgataatctc atgaccaaaa tcccttaacg   6000
tgagttttcg ttccactgag cgtcagaccc cgtagaaaag atcaaaggat cttcttgaga   6060
tcctttttt ctgcgcgtaa tctgctgctt gcaaacaaaa aaaccaccgc taccagcggt   6120
ggtttgtttg ccggatcaag agctaccaac tctttttccg aaggtaactg gcttcagcag   6180
agcgcagata ccaaatactg tccttctagt gtagccgtag ttaggccacc acttcaagaa   6240
ctctgtagca ccgcctacat acctcgctct gctaatcctg ttaccagtgg ctgctgccag   6300
tggcgataag tcgtgtctta ccgggttgga ctcaagacga tagttaccgg ataaggcgca   6360
gcggtcgggc tgaacggggg gttcgtgcac acagcccagc ttggagcgaa cgacctacac   6420
cgaactgaga tacctacagc gtgagctatg agaaagcgcc acgcttcccg aagggagaaa   6480
ggcggacagg tatccggtaa gcggcagggt cggaacagga gagcgcacga gggagcttcc   6540
agggggaaac gcctggtatc tttatagtcc tgtcgggttt cgccacctct gacttgagcg   6600
tcgatttttg tgatgctcgt caggggggcg gagcctatgg aaaaacgcca gcaacgcggc   6660
ctttttacgg ttcctggcct tttgctggcc ttttgctcac atgttctttc ctgcgttatc   6720
ccctgattct gtggataacc gtattaccgc catgcattag ttattaatag taatcaatta   6780
cggggtcatt agttcatagc ccatatatgg agttccgcgt tacataactt acggtaaatg   6840
gcccgcctgg ctgaccgccc aacgaccccc gcccattgac gtcaataatg acgtatgttc   6900
ccatagtaac gccaataggg actttccatt gacgtcaatg ggtggagtat ttacggtaaa   6960
ctgcccactt ggcagtacat caagtgtatc atatgccaag tacgccccct attgacgtca   7020
atgacggtaa atggcccgcc tggcattatg cccagtacat gaccttatgg gactttccta   7080
cttggcagta catctacgta ttagtcatcg ctattaccat ggtgatgcgg ttttggcagt   7140
acatcaatgg gcgtggatag cggtttgact cacggggatt tccaagtctc caccccattg   7200
acgtcaatgg gagtttgttt tggcaccaaa atcaacggga ctttccaaaa tgtcgtaaca   7260
actccgc                                                             7267
```

<210> SEQ ID NO 70
<211> LENGTH: 2427
<212> TYPE: DNA

<213> ORGANISM: Artificial Sequence
<220> FEATURE:
<223> OTHER INFORMATION: Synthetic

<400> SEQUENCE: 70

```
atgagggccc tgtgggtgct gggcctctgc tgcgtcctgc tgaccttcgg gtcggtcaga     60
gctgacgatg aagttgatgt ggatggtaca gtagaagagg atctgggtaa aagtagagaa    120
ggatcaagga cggatgatga agtagtacag agagaggaag aagctattca gttggatgga    180
ttaaatgcat cacaaataag agaacttaga gagaagtcgg aaaagtttgc cttccaagcc    240
gaagttaaca gaatgatgaa acttatcatc aattcattgt ataaaaataa agagattttc    300
ctgagagaac tgatttcaaa tgcttctgat gctttagata agataaggct aatatcactg    360
actgatgaaa atgctctttc tggaaatgag gaactaacag tcaaaattaa gtgtgataag    420
gagaagaacc tgctgcatgt cacagacacc ggtgtaggaa tgaccagaga agagttggtt    480
aaaaaccttg gtaccatagc caaatctggg acaagcgagt tttaaacaa aatgactgaa    540
gcacaggaag atggccagtc aacttctgaa ttgattggcc agtttggtgt cggtttctat    600
tccgccttcc ttgtagcaga taaggttatt gtcacttcaa aacacaacaa cgatacccag    660
cacatctggg agtctgactc caatgaattt tctgtaattg ctgacccaag aggaaacact    720
ctaggacggg gaacgacaat tacccttgtc ttaaaagaag aagcatctga ttaccttgaa    780
ttggatacaa ttaaaaatct cgtcaaaaaa tattcacagt tcataaactt tcctatttat    840
gtatggagca gcaagactga aactgttgag gagcccatgg aggaagaaga agcagccaaa    900
gaagagaaag aagaatctga tgatgaagct gcagtagagg aagaagaaga agaaaagaaa    960
ccaaagacta aaaaagttga aaaaactgtc tgggactggg aacttatgaa tgatatcaaa   1020
ccaatatggc agagaccatc aaaagaagta gaagaagatg aatacaaagc tttctacaaa   1080
tcattttcaa aggaaagtga tgaccccatg gcttatattc actttactgc tgaaggggaa   1140
gttaccttca aatcaatttt atttgtaccc acatctgctc cacgtggtct gtttgacgaa   1200
tatggatcta aaaagagcga ttacattaag ctctatgtgc gccgtgtatt catcacagac   1260
gacttccatg atatgatgcc taaatacctc aattttgtca agggtgtggt ggactcagat   1320
gatctcccct tgaatgtttc ccgcgagact cttcagcaac ataaactgct taaggtgatt   1380
aggaagaagc ttgttcgtaa aacgctggac atgatcaaga agattgctga tgataaatac   1440
aatgatactt tttggaaaga atttggtacc aacatcaagc ttggtgtgat tgaagaccac   1500
tcgaatcgaa cacgtcttgc taaacttctt aggttccagt cttctcatca tccaactgac   1560
attactagcc tagaccagta tgtggaaaga atgaaggaaa aacaagacaa aatctacttc   1620
atggctgggt ccagcagaaa agaggctgaa tcttctccat ttgttgagcg acttctgaaa   1680
aagggctatg aagttattta cctcacagaa cctgtggatg aatactgtat tcaggccctt   1740
cccgaatttg atgggaagag gttccagaat gttgccaagg aaggagtgaa gttcgatgaa   1800
agtgagaaaa ctaaggagag tcgtgaagca gttgagaaag aatttgagcc tctgctgaat   1860
tggatgaaag ataaagccct taaggacaag attgaaaagg ctgtggtgtc tcagcgcctg   1920
acagaatctc cgtgtgcttt ggtggccagc cagtacgcag cgtctgccgc agctgctgca   1980
atcatgaaag cacaagcgta ccaaacgggc aaggacatct ctacaaatta ctatgcgagt   2040
cagaagaaaa catttgaaat taatcccaga cacccgctga tcagagacat gcttcgacga   2100
attaaggaag atgaagatga taaaacagtt ttggatcttg ctgtggtttt gtttgaaaca   2160
gcaacgcttc ggtcagggta tcttttacca gacactaaag catatggaga tagaatagaa   2220
```

```
agaatgcttc gcctcagttt gaacattgac cctgatgcaa aggtggaaga agagcctgaa   2280
gaagaacctg aagagacagc agaagacaca acagaagaca cagagcaaga cgaagatgaa   2340
gaaatggatg tgggaacaga tgaagaagaa gaaacagcaa aggaatctac agctgaatac   2400
ccatatgacg tcccggatta cgcttaa                                       2427
```

<210> SEQ ID NO 71
<211> LENGTH: 2428
<212> TYPE: DNA
<213> ORGANISM: Artificial Sequence
<220> FEATURE:
<223> OTHER INFORMATION: Synthetic

<400> SEQUENCE: 71

```
atgagggccc tgtgggtgct gggcctctgc tgcgtcctgc tgaccttcgg gtcggtcaga     60
gctgacgatg aagttgatgt ggatggtaca gtagaagagg atctgggtaa aagtagagaa    120
ggatcaagga cggatgatga agtagtacag agagaggaag aagctattca gttggatgga    180
ttaaatgcat cacaaataag agaacttaga gagaagtcgg aaaagtttgc cttccaagcc    240
gaagttaaca gaatgatgaa acttatcatc aattcattgt ataaaaataa agagattttc    300
ctgagagaac tgatttcaaa tgcttctgat gctttagata agataaggct aatatcactg    360
actgatgaaa atgctctttc tggaaatgag gaactaacag tcaaaattaa gtgtgataag    420
gagaagaacc tgctgcatgt cacagacacc ggtgtaggaa tgaccagaga agagttggtt    480
aaaaaccttg gtaccatagc caaatctggg acaagcgagt ttttaaacaa aatgactgaa    540
gcacaggaag atggccagtc aacttctgaa ttgattggcc agtttggtgt cggtttctat    600
tccgccttcc ttgtagcaga taaggttatt gtcacttcaa aacacaacaa cgatacccag    660
cacatctggg agtctgactc caatgaattt tctgtaattg ctgacccaag aggaaacact    720
ctaggacggg gaacgacaat taccettgtc ttaaaagaag aagcatctga ttaccttgaa    780
ttggatacaa ttaaaaatct cgtcaaaaaa tattcacagt tcataaactt tcctatttat    840
gtatggagca gcaagactga aactgttgag gagcccatgg aggaagaaga agcagccaaa    900
gaagagaaag aagaatctga tgatgaagct gcagtagagg aagaagaaga agaaaagaaa    960
ccaaagacta aaaaagttga aaaaactgtc tgggactggg aacttatgaa tgatatcaaa   1020
ccaatatggc agagaccatc aaaagaagta gaagaagatg aatacaaagc tttctacaaa   1080
tcattttcaa aggaaagtga tgaccccatg gcttatattc actttactgc tgaaggggaa   1140
gttaccttca aatcaatttt atttgtaccc acatctgctc cacgtggtct gtttgacgaa   1200
tatggatcta aaaagagcga ttacattaag ctctatgtgc gccgtgtatt catcacagac   1260
gacttccatg atatgatgcc taaatacctc aattttgtca agggtgtggt ggactcagat   1320
gatctcccct tgaatgtttc ccgcgagact cttcagcaac ataaactgct taaggtgatt   1380
aggaagaagc ttgttcgtaa aacgctggac atgatcaaga agattgctga tgataaatac   1440
aatgatactt tttggaaaga atttggtacc aacatcaagc ttggtgtgat tgaagaccac   1500
tcgaatcgaa cacgtcttgc taaacttctt aggttccagt cttctcatca tccaactgac   1560
attactagcc tagaccagta tgtggaaaga atgaaggaaa aacaagacaa aatctacttc   1620
atggctgggt ccagcagaaa agaggctgaa tcttctccat ttgttgagcg acttctgaaa   1680
aagggctatg aagttattta cctcacagaa cctgtggatg aatactgtat tcaggccctt   1740
cccgaatttg atgggaagag gttccagaat gttgccaagg aaggagtgaa gttcgatgaa   1800
```

```
agtgagaaaa ctaaggagag tcgtgaagca gttgagaaag aatttgagcc tctgctgaat   1860

tggatgaaag ataaagccct taaggacaag attgaaaagg ctgtggtgtc tcagcgcctg   1920

acagaatctc cgtgtgcttt ggtggccagc cagtacggat ggtctggcaa catggagaga   1980

atcatgaaag cacaagctta cgcaacgggc aaggccatct ctacaaatgc cgctgcgagt   2040

cagaagaaaa catttgaaat taattcccag acacccgctg atcagagaca tgcttcgacg   2100

aattaaggaa gatgaagatg ataaaacagt tttggatctt gctgtggttt tgtttgaaac   2160

agcaacgctt cggtcagggt atctttttacc agacactaaa gcatatggag atagaataga   2220

aagaatgctt cgcctcagtt tgaacattga ccctgatgca aaggtggaag aagagcctga   2280

agaagaacct gaagagacag cagaagacac aacagaagac acagagcaag acgaagatga   2340

agaaatggat gtgggaacag atgaagaaga agaaacagca aaggaatcta cagctgaata   2400

cccatatgac gtcccggatt acgcttaa                                       2428
```

<210> SEQ ID NO 72
<211> LENGTH: 2400
<212> TYPE: DNA
<213> ORGANISM: Homo Sapiens

<400> SEQUENCE: 72

```
atgagggccc tgtgggtgct gggcctctgc tgcgtcctgc tgaccttcgg gtcggtcaga     60

gctgacgatg aagttgatgt ggatggtaca gtagaagagg atctgggtaa aagtagagaa    120

ggatcaagga cggatgatga agtagtacag agagaggaag aagctattca gttggatgga    180

ttaaatgcat cacaaataag agaacttaga gagaagtcgg aaaagtttgc cttccaagcc    240

gaagttaaca gaatgatgaa acttatcatc aattcattgt ataaaaataa agagattttc    300

ctgagagaac tgatttcaaa tgcttctgat gctttagata agataaggct aatatcactg    360

actgatgaaa atgctctttc tggaaatgag gaactaacag tcaaaattaa gtgtgataag    420

gagaagaacc tgctgcatgt cacagacacc ggtgtaggaa tgaccagaga agagttggtt    480

aaaaaccttg gtaccatagc caaatctggg acaagcgagt ttttaaacaa aatgactgaa    540

gcacaggaag atggccagtc aacttctgaa ttgattggcc agtttggtgt cggtttctat    600

tccgccttcc ttgtagcaga taaggttatt gtcacttcaa aacacaacaa cgatacccag    660

cacatctggg agtctgactc caatgaattt tctgtaattg ctgacccaag aggaaacact    720

ctaggacggg gaacgacaat tacccttgtc ttaaaagaag aagcatctga ttaccttgaa    780

ttggatacaa ttaaaaatct cgtcaaaaaa tattcacagt tcataaactt tcctatttat    840

gtatggagca gcaagactga aactgttgag gagcccatgg aggaagaaga agcagccaaa    900

gaagagaaag aagaatctga tgatgaagct gcagtagagg aagaagaaga agaaaagaaa    960

ccaaagacta aaaaagttga aaaaactgtc tgggactggg aacttatgaa tgatatcaaa   1020

ccaatatggc agagaccatc aaaagaagta gaagaagatg aatacaaagc tttctacaaa   1080

tcattttcaa aggaaagtga tgaccccatg gcttatattc actttactgc tgaaggggaa   1140

gttaccttca aatcaatttt atttgtaccc acatctgctc cacgtggtct gtttgacgaa   1200

tatggatcta aaaagagcga ttacattaag ctctatgtgc gccgtgtatt catcacagac   1260

gacttccatg atatgatgcc taaatacctc aattttgtca agggtgtggt ggactcagat   1320

gatctcccct tgaatgtttc ccgcgagact cttcagcaac ataaactgct taaggtgatt   1380

aggaagaagc ttgttcgtaa aacgctggac atgatcaaga agattgctga tgataaatac   1440

aatgatactt tttggaaaga atttggtacc aacatcaagc ttggtgtgat tgaagaccac   1500
```

tcgaatcgaa cacgtcttgc taaacttctt aggttccagt cttctcatca tccaactgac 1560
attactagcc tagaccagta tgtggaaaga atgaaggaaa aacaagacaa aatctacttc 1620
atggctgggt ccagcagaaa agaggctgaa tcttctccat ttgttgagcg acttctgaaa 1680
aagggctatg aagttattta cctcacagaa cctgtggatg aatactgtat tcaggccctt 1740
cccgaatttg atgggaagag gttccagaat gttgccaagg aaggagtgaa gttcgatgaa 1800
agtgagaaaa ctaaggagag tcgtgaagca gttgagaaag aatttgagcc tctgctgaat 1860
tggatgaaag ataaagccct taaggacaag attgaaaagg ctgtggtgtc tcagcgcctg 1920
acagaatctc cgtgtgcttt ggtggccagc cagtacggat ggtctggcaa catggagaga 1980
atcatgaaag cacaagcgta ccaaacgggc aaggacatct ctacaaatta ctatgcgagt 2040
cagaagaaaa catttgaaat taatcccaga cacccgctga tcagagacat gcttcgacga 2100
attaaggaag atgaagatga taaaacagtt ttggatcttg ctgtggtttt gtttgaaaca 2160
gcaacgcttc ggtcagggta tcttttacca gacactaaag catatggaga tagaatagaa 2220
agaatgcttc gcctcagttt gaacattgac cctgatgcaa aggtggaaga agagcctgaa 2280
gaagaacctg aagagacagc agaagacaca acagaagaca cagagcaaga cgaagatgaa 2340
gaaatggatg tgggaacaga tgaagaagaa gaaacagcaa aggaatctac agctgaataa 2400

<210> SEQ ID NO 73
<211> LENGTH: 2427
<212> TYPE: DNA
<213> ORGANISM: Artificial Sequence
<220> FEATURE:
<223> OTHER INFORMATION: Synthetic

<400> SEQUENCE: 73
atgagggccc tgtgggtgct gggcctctgc tgcgtcctgc tgaccttcgg gtcggtcaga 60
gctgacgatg aagttgatgt ggatggtaca gtagaagagg atctgggtaa aagtagagaa 120
ggatcaagga cggatgatga agtagtacag agagaggaag aagctattca gttggatgga 180
ttaaatgcat cacaaataag agaacttaga gagaagtcgg aaaagtttgc cttccaagcc 240
gaagttaaca gaatgatgaa acttatcatc aattcattgt ataaaaataa agagattttc 300
ctgagagaac tgatttcaaa tgcttctgat gctttagata agataaggct aatatcactg 360
actgatgaaa atgctctttc tggaaatgag gaactaacag tcaaaattaa gtgtgataag 420
gagaagaacc tgctgcatgt cacagacacc ggtgtaggaa tgaccagaga agagttggtt 480
aaaaaccttg gtaccatagc caaatctggg acaagcgagt tttaaacaa aatgactgaa 540 gcacaggaag atggccagtc aacttctgaa ttgattggcc agtttggtgt cggtttctat 600
tccgccttcc ttgtagcaga taaggttatt gtcacttcaa aacacaacaa cgatacccag 660
cacatctggg agtctgactc caatgaattt tctgtaattg ctgacccaag aggaaacact 720
ctaggacggg gaacgacaat tacccttgtc ttaaaagaag aagcatctga ttaccttgaa 780
ttggatacaa ttaaaaatct cgtcaaaaaa tattcacagt tcataaactt tcctatttat 840
gtatggagca gcaagactga aactgttgag gagcccatgg aggaagaaga agcagccaaa 900
gaagagaaag aagaatctga tgatgaagct gcagtagagg aagaagaaga agaaaagaaa 960
ccaaagacta aaaaagttga aaaaactgtc tgggactggg aacttatgaa tgatatcaaa 1020
ccaatatggc agagaccatc aaaagaagta gaagaagatg aatacaaagc tttctacaaa 1080
tcattttcaa aggaaagtga tgaccccatg gcttatattc actttactgc tgaaggggaa 1140

```
gttaccttca aatcaatttt atttgtaccc acatctgctc cacgtggtct gtttgacgaa   1200
tatggatcta aaaagagcga ttacattaag ctctatgtgc gccgtgtatt catcacagac   1260
gacttccatg atatgatgcc taaatacctc aattttgtca agggtgtggt ggactcagat   1320
gatctcccct tgaatgtttc ccgcgagact cttcagcaac ataaactgct taaggtgatt   1380
aggaagaagc ttgttcgtaa aacgctggac atgatcaaga agattgctga tgataaatac   1440
aatgatactt tttggaaaga atttggtacc aacatcaagc ttggtgtgat tgaagaccac   1500
tcgaatcgaa cacgtcttgc taaacttctt aggttccagt cttctcatca tccaactgac   1560
attactagcc tagaccagta tgtggaaaga atgaaggaaa aacaagacaa aatctacttc   1620
atggctgggt ccagcagaaa agaggctgaa tcttctccat ttgttgagcg acttctgaaa   1680
aagggctatg aagttattta cctcacagaa cctgtggatg aatactgtat tcaggccctt   1740
cccgaatttg atgggaagag gttccagaat gttgccaagg aaggagtgaa gttcgatgaa   1800
agtgagaaaa ctaaggagag tcgtgaagca gttgagaaag aatttgagcc tctgctgaat   1860
tggatgaaag ataaagccct taaggacaag attgaaaagg ctgtggtgtc tcagcgcctg   1920
acagaatctc cgtgtgcttt ggtggccagc cagtacggat ggtctggcaa catggagaga   1980
atcatgaaag cacaagcgta ccaaacgggc aaggacatct ctacaaatta ctatgcgagt   2040
cagaagaaaa catttgaaat taatcccaga cacccgctga tcagagacat gcttcgacga   2100
attaaggaag atgaagatga taaaacagtt ttggatcttg ctgtggtttt gtttgaaaca   2160
gcaacgcttc ggtcagggta tcttttacca gacactaaag catatggaga tagaatagaa   2220
agaatgcttc gcctcagttt gaacattgac cctgatgcaa aggtggaaga agagcctgaa   2280
gaagaacctg aagagacagc agaagacaca acagaagaca cagagcaaga cgaagatgaa   2340
gaaatggatg tgggaacaga tgaagaagaa gaaacagcaa aggaatctac agctgaatac   2400
ccatatgacg tcccggatta cgcttaa                                       2427
```

<210> SEQ ID NO 74
<211> LENGTH: 2799
<212> TYPE: DNA
<213> ORGANISM: Artificial Sequence
<220> FEATURE:
<223> OTHER INFORMATION: Synthetic

<400> SEQUENCE: 74

```
atgggcaccg tcagctccag gcggtcctgg tggccgctgc cactgctgct gctgctgctg     60
ctgctcctgg gtcccgcggg cgcccgtgcg caggaggacg aggacggcga ctacgaggag    120
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg gaagggcacg    780
```

```
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgagac    960
gatgcctgcc tctactcccc agcctcagct cccgaggtca tcacagttgg ggccaccaat   1020
gcccaggacc agccggtgac cctggggact ttggggacca actttggccg ctgtgtggac   1080
ctctttgccc caggggagga catcattggt gcctccagct actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgccccccag cacccatggg gcaggttggc agctgttttg caggactgtg   1380
tggtcagcac actcggggcc tacacggatg gccacagcca tcgcccgctg cgccccagat   1440
gaggagctgc tgagctgctc cagtttctcc aggagtggga agcggcgggg cgagcgcatg   1500
gaggcccaag gggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacagggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctgggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctacagaccg gtcgccacat ggtgagcaag   2100
ggcgaggagg ataacatggc catcatcaag gagttcatgc gcttcaaggt gcacatggag   2160
ggctccgtga acggccacga gttcgagatc gagggcgagg gcgagggccg cccctacgag   2220
ggcacccaga ccgccaagct gaaggtgacc aagggtggcc ccctgccctt cgcctgggac   2280
atcctgtccc ctcagttcat gtacggctcc aaggcctacg tgaagcaccc cgccgacatc   2340
cccgactact tgaagctgtc cttccccgag ggcttcaagt gggagcgcgt gatgaacttc   2400
gaggacggcg gcgtggtgac cgtgacccag gactcctccc tgcaggacgg cgagttcatc   2460
tacaaggtga agctgcgcgg caccaacttc ccctccgacg gccccgtaat gcagaagaag   2520
accatgggct gggaggcctc ctccgagcgg atgtaccccg aggacggcgc cctgaagggc   2580
gagatcaagc agaggctgaa gctgaaggac ggcggccact acgacgctga ggtcaagacc   2640
acctacaagg ccaagaagcc cgtgcagctg cccggcgcct acaacgtcaa catcaagttg   2700
gacatcacct cccacaacga ggactacacc atcgtggaac agtacgaacg cgccgagggc   2760
cgccactcca ccggcggcat ggacgagctg tacaagtaa                          2799
```

<210> SEQ ID NO 75
<211> LENGTH: 932
<212> TYPE: PRT
<213> ORGANISM: Artificial Sequence
<220> FEATURE:
<223> OTHER INFORMATION: Synthetic

<400> SEQUENCE: 75

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
```

```
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln Thr Gly Arg His Met Val Ser Lys Gly Glu Glu Asp
    690                 695                 700

Asn Met Ala Ile Ile Lys Glu Phe Met Arg Phe Lys Val His Met Glu
705                 710                 715                 720

Gly Ser Val Asn Gly His Glu Phe Glu Ile Glu Gly Glu Gly Glu Gly
                725                 730                 735

Arg Pro Tyr Glu Gly Thr Gln Thr Ala Lys Leu Lys Val Thr Lys Gly
            740                 745                 750

Gly Pro Leu Pro Phe Ala Trp Asp Ile Leu Ser Pro Gln Phe Met Tyr
        755                 760                 765

Gly Ser Lys Ala Tyr Val Lys His Pro Ala Asp Ile Pro Asp Tyr Leu
    770                 775                 780

Lys Leu Ser Phe Pro Glu Gly Phe Lys Trp Glu Arg Val Met Asn Phe
785                 790                 795                 800

Glu Asp Gly Gly Val Val Thr Val Thr Gln Asp Ser Ser Leu Gln Asp
                805                 810                 815

Gly Glu Phe Ile Tyr Lys Val Lys Leu Arg Gly Thr Asn Phe Pro Ser
            820                 825                 830

Asp Gly Pro Val Met Gln Lys Lys Thr Met Gly Trp Glu Ala Ser Ser
        835                 840                 845
```

```
Glu Arg Met Tyr Pro Glu Asp Gly Ala Leu Lys Gly Glu Ile Lys Gln
    850                 855                 860

Arg Leu Lys Leu Lys Asp Gly Gly His Tyr Asp Ala Glu Val Lys Thr
865                 870                 875                 880

Thr Tyr Lys Ala Lys Lys Pro Val Gln Leu Pro Gly Ala Tyr Asn Val
                885                 890                 895

Asn Ile Lys Leu Asp Ile Thr Ser His Asn Glu Asp Tyr Thr Ile Val
            900                 905                 910

Glu Gln Tyr Glu Arg Ala Glu Gly Arg His Ser Thr Gly Gly Met Asp
        915                 920                 925

Glu Leu Tyr Lys
    930


<210> SEQ ID NO 76
<211> LENGTH: 932
<212> TYPE: PRT
<213> ORGANISM: Artificial Sequence
<220> FEATURE:
<223> OTHER INFORMATION: Synthetic

<400> SEQUENCE: 76

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270
```

```
Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Tyr Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685
```

```
Gln Glu Leu Gln Thr Gly Arg His Met Val Ser Lys Gly Glu Glu Asp
    690                 695                 700

Asn Met Ala Ile Ile Lys Glu Phe Met Arg Phe Lys Val His Met Glu
705                 710                 715                 720

Gly Ser Val Asn Gly His Glu Phe Glu Ile Glu Gly Glu Gly Glu Gly
                725                 730                 735

Arg Pro Tyr Glu Gly Thr Gln Thr Ala Lys Leu Lys Val Thr Lys Gly
            740                 745                 750

Gly Pro Leu Pro Phe Ala Trp Asp Ile Leu Ser Pro Gln Phe Met Tyr
        755                 760                 765

Gly Ser Lys Ala Tyr Val Lys His Pro Ala Asp Ile Pro Asp Tyr Leu
    770                 775                 780

Lys Leu Ser Phe Pro Glu Gly Phe Lys Trp Glu Arg Val Met Asn Phe
785                 790                 795                 800

Glu Asp Gly Gly Val Val Thr Val Thr Gln Asp Ser Ser Leu Gln Asp
                805                 810                 815

Gly Glu Phe Ile Tyr Lys Val Lys Leu Arg Gly Thr Asn Phe Pro Ser
            820                 825                 830

Asp Gly Pro Val Met Gln Lys Lys Thr Met Gly Trp Glu Ala Ser Ser
        835                 840                 845

Glu Arg Met Tyr Pro Glu Asp Gly Ala Leu Lys Gly Glu Ile Lys Gln
    850                 855                 860

Arg Leu Lys Leu Lys Asp Gly Gly His Tyr Asp Ala Glu Val Lys Thr
865                 870                 875                 880

Thr Tyr Lys Ala Lys Lys Pro Val Gln Leu Pro Gly Ala Tyr Asn Val
                885                 890                 895

Asn Ile Lys Leu Asp Ile Thr Ser His Asn Glu Asp Tyr Thr Ile Val
            900                 905                 910

Glu Gln Tyr Glu Arg Ala Glu Gly Arg His Ser Thr Gly Gly Met Asp
        915                 920                 925

Glu Leu Tyr Lys
    930


<210> SEQ ID NO 77
<211> LENGTH: 1101
<212> TYPE: PRT
<213> ORGANISM: Artificial Sequence
<220> FEATURE:
<223> OTHER INFORMATION: Synthetic

<400> SEQUENCE: 77

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110
```

```
Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
```

```
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala Thr Gly Met Val
    850                 855                 860

Ser Lys Gly Glu Glu Leu Phe Thr Gly Val Val Pro Ile Leu Val Glu
865                 870                 875                 880

Leu Asp Gly Asp Val Asn Gly His Lys Phe Ser Val Ser Gly Glu Gly
                885                 890                 895

Glu Gly Asp Ala Thr Tyr Gly Lys Leu Thr Leu Lys Phe Ile Cys Thr
            900                 905                 910

Thr Gly Lys Leu Pro Val Pro Trp Pro Thr Leu Val Thr Thr Leu Thr
        915                 920                 925

Tyr Gly Val Gln Cys Phe Ser Arg Tyr Pro Asp His Met Lys Gln His
    930                 935                 940

Asp Phe Phe Lys Ser Ala Met Pro Glu Gly Tyr Val Gln Glu Arg Thr
945                 950                 955                 960
```

```
Ile Phe Phe Lys Asp Asp Gly Asn Tyr Lys Thr Arg Ala Glu Val Lys
                965                 970                 975

Phe Glu Gly Asp Thr Leu Val Asn Arg Ile Glu Leu Lys Gly Ile Asp
            980                 985                 990

Phe Lys Glu Asp Gly Asn Ile Leu  Gly His Lys Leu Glu  Tyr Asn Tyr
        995                 1000                1005

Asn Ser  His Asn Val Tyr Ile  Met Ala Asp Lys Gln  Lys Asn Gly
    1010                1015                1020

Ile Lys  Val Asn Phe Lys Ile  Arg His Asn Ile Glu  Asp Gly Ser
    1025                1030                1035

Val Gln  Leu Ala Asp His Tyr  Gln Gln Asn Thr Pro  Ile Gly Asp
    1040                1045                1050

Gly Pro  Val Leu Leu Pro Asp  Asn His Tyr Leu Ser  Thr Gln Ser
    1055                1060                1065

Ala Leu  Ser Lys Asp Pro Asn  Glu Lys Arg Asp His  Met Val Leu
    1070                1075                1080

Leu Glu  Phe Val Thr Ala Ala  Gly Ile Thr Leu Gly  Met Asp Glu
    1085                1090                1095

Leu Tyr  Lys
    1100


<210> SEQ ID NO 78
<211> LENGTH: 27
<212> TYPE: PRT
<213> ORGANISM: Artificial Sequence
<220> FEATURE:
<223> OTHER INFORMATION: Synthetic

<400> SEQUENCE: 78

Tyr Ala Ala Ser Ala Ala Ala Ala Ala Ile Met Lys Ala Gln Ala Tyr
1               5                   10                  15

Gln Thr Gly Lys Asp Ile Ser Thr Asn Tyr Tyr
            20                  25


<210> SEQ ID NO 79
<211> LENGTH: 27
<212> TYPE: PRT
<213> ORGANISM: Artificial Sequence
<220> FEATURE:
<223> OTHER INFORMATION: Synthetic

<400> SEQUENCE: 79

Tyr Gly Trp Ser Gly Asn Met Glu Arg Ile Met Lys Ala Gln Ala Tyr
1               5                   10                  15

Ala Thr Gly Lys Ala Ile Ser Thr Asn Ala Ala
            20                  25
```

PCSK9 INHIBITORY POLYPOLYPEPTIDES AND METHODS OF USE

The present application hereby incorporates by reference the material in the text file 20111-191-SequenceListing-Dec11-2017-ST25.TXT created on Dec. 11, 2017 of size 146,512 bytes and filed concurrently herewith. This text file contains all the sequences mentioned in the present application.

FIELD OF THE INVENTION

The present invention belongs to the field of biomedicine. Specifically, the invention relates to polypeptides, derivatives thereof, and their use in the preparation of pharmaceutical compositions for treating cardiovascular or inflammatory disorders as well as in cell-based drug screening assay methods and systems.

BACKGROUND OF THE INVENTION

The high prevalence of cardiovascular disease (CVD) is a major public health problem that is expected to increase in the next decades (Heidenreich et al., 2011; Mackay and Mensah, 2004). Main risk factors include hypertension, diabetes, obesity and hypercholesterolemia. The most potent factor contributing to atherogenesis is longstanding hypercholesterolemia, high circulating levels of low-density lipoproteins (LDL) that result in excess cholesterol deposition in arterial vessel walls (Kannel et al., 1961; Müller, 1938; Yusuf et al., 2004).

Sub-endothelial retention of LDL particles within arterial walls is an important initiating event in atherosclerosis, leading to pathological accumulation of lipids, cell debris and chronic inflammation often culminating in coronary events and stroke (Lusis, 2000; Mackay and Mensah, 2004). Plasma LDL particles carry ~70% of total circulating cholesterol in humans. Clearance of LDL particles is initiated by binding of apolipoprotein B100 (ApoB) to hepatic LDL receptor (LDLR) present on the particle surface; mediating LDL particle endocytosis (Brown and Goldstein, 1986). Heterozygous familial hypercholesterolemia (HeFH) is characterized by elevated levels of circulating LDL due to a decreased LDL catabolism. HeFH occurs in approximately 1 in 500 people and is associated genetic variants of LDLR and also in APOB, ARH and APOE loci (Kannel et al., 1961; Marduel et al., 2013; Rader et al., 2003). The homozygous FH phenotype is even more severe and characterized by very high levels of circulating LDL, premature atherosclerosis and very high prevalence of cardiovascular complications at an early age.

Proprotein convertase subtilisin/kexin type 9 (SEQ. ID NO. 1; PCSK9) (Seidah et al., 2003) has been identified as a third locus associated with FH (Abifadel et al., 2003). PCSK9 acts a natural inducer of low density lipoprotein receptor (LDLR) degradation (Benjannet et al., 2004; Maxwell and Breslow, 2004; Park et al., 2004). Loss-of-function (LOF) mutations (Berge et al., 2006; Cohen et al., 2005; Hooper et al., 2007) or genetic invalidation (Rashid et al., 2005) at the PCSK9 locus robustly lowers circulating LDL level and is associated with reduced cardiovascular events. up to 88% reduction in humans (Cohen et al., 2006). To date >1700 LDLR and >160 PCSK9 allelic variants have been identified (Abifadel et al., 2009; Leigh et al., 2008; Leigh et al., 2009). In human genetic studies, PCSK9 inhibition has been demonstrated as a safe and potent approach for lowing LDL, reducing atherosclerosis progression and CVD risk (Cohen et al., 2006; Hooper et al., 2007; Zhao et al., 2006).

PCSK9 is almost exclusively expressed in the liver and to a lesser extent in other tissues such as the intestine and kidney (Seidah et al., 2003). PCSK9 plays an important role in controlling LDLR levels and therefore LDL-C uptake by the liver (Maxwell, K. N. (2004) *Proc. Natl. Acad. Sci. USA* 101, 7100-7105, Benjannet, S., et al. (2004) *J. Biol. Chem.* 279, 48865-48875, Park, S. W., (2004) *J. Biol. Chem.* 279, 50630-50638). In functional genomics studies, PCSK9 has been identified as a direct target of sterol regulatory element-binding protein-2 (SREBP-2) and shown to be co-regulated with 3-hydroxy-3-methylglutaryl coenzyme A (HMG-CoA) reductase (the rate-limiting enzyme for cholesterol synthesis) and LDLR (Horton et al., 2003; Maxwell et al., 2003).

Statin drugs (HMG-CoA reductase inhibitors), the most commonly used class of LDL-lowering drugs (Wenner Moyer), increase PCSK9 expression (Dubuc et al., 2004). Higher PCSK9 levels significantly attenuate statin-mediated increases in LDLR protein level (Rashid et al., 2005). Elevated PCSK9 appears to counter the therapeutic effect of statin therapy and explains why patients at high risk for CVD when treated with statins often to do achieve statin therapeutic goals with respect to LDL level.

PCSK9 induces the intracellular degradation of LDLR, VLDLR and ApoER2 in acidic compartments (Maxwell et al., 2005; Poirier et al., 2008) independently of its catalytic activity (McNutt et al., 2007) thereby causing LDL levels to rise (Benjannet et al., 2004; Maxwell and Breslow, 2004; Park et al., 2004; Rashid et al., 2005). So far, the exact mechanism by which PCSK9 induces LDLR degradation has remained elusive. The prevailing hypothesis is that intracellular or secreted PCSK9 interacts directly with the EGF-A domain of LDLR with a Kd of ~169 nM (Kwon et al., 2008; Zhang et al., 2007). PCSK9-LDLR complex is internalized from the plasma membrane to endosomes via clathrin-coated vesicles and the cytosolic adaptor protein ARH (Lagace et al., 2006; Nassoury et al., 2007; Wang et al., 2012). Within the acidic environment of endosomes, the affinity of PCSK9 for LDLR increases considerably (Kd ~1 nM), which is thought to create additional sites of interaction (Cunningham et al., 2007; Yamamoto et al., 2011). This two-step binding model may explain how PCSK9 hinders recycling of LDLR to the cell surface, (Zhang et al., 2008) thereby promoting its degradation by lysosomal hydrolases independently of ubiquitination, autophagy and the endosomal sorting complex (ESCRT) (Wang et al., 2012).

Several clinical trials have shown a strong positive correlation between LDL lowering and reduction in coronary heart disease risk (Baigent et al., 2010; O'Keefe et al., 2004). Statins, currently the most powerful class of lipid-lowering drugs, can decrease LDL level by 20-55% depending on the statin molecule and dosage (Kapur and Musunuru, 2008). In addition, combining of statins ezetimibe, bile-acid sequestrants, or niacin can produce an additional 10 to 20% decrease in LDL (Hou and Goldberg, 2009). However, even though these combination therapies achieve substantial reductions in circulating LDL, more efficient LDL-lowering therapies are still needed, especially for patients with very high initial LDL levels. Many of these patients (10-20%) have undesirable side effects with high-dose statins and/or fail to achieve recommended LDL targets (Bruckert et al., 2005). In order to fill these important clinical needs, PCSK9 antagonists are suited to increase LDLR levels and LDL clearance to prevent coronary heart diseases. Indeed, PCSK9 is a genetically and pharmacologically validated lipid-lowering target.

PCSK9 activity has also been implicated in infectious disease and inflammation. PCSK9-deficient mice or patients with PCSK9 loss-of-function mutations have significantly reduced septic inflammatory responses and enhanced clearance and detoxification of circulating pathogen lipids such as lipopolysaccharide (LPS) via LDLR (Walley et al., 2014).

Despite significant advances in understanding the role of PCSK9 in controlling LDLR level, mechanisms by which PCSK9 levels or activity can be reduced and development of a variety of PCSK9 modulating agents (Poirier and Mayer, 2013), there remains a need for PCSK9 modulators with improved therapeutic effects and cell-based assays that facilitate identification and evaluation of PCSK9 modulators.

SUMMARY OF THE INVENTION

The present invention provides polypeptides that bind to PCSK9 (SEQ. ID. NO. 1) inhibiting: (i) plasma membrane (PM) internalization of PCSK9-low-density lipoprotein receptor (e.g. SEQ. ID. NO. 2) complexes (PCSK9-LDLR), (ii) intracellular trafficking of PCSK9-LDLR to endosomes and (iii) degradation of the complex in endosomes. By reducing internalization and degradation of PCSK9-LDLR the polypeptides of the invention increase cell surface LDLR and reduce circulating LDL levels. The polypeptides of the invention are useful for treating conditions associated with elevated lipids including atherosclerosis and sepsis.

Polypeptides

The present invention provides a polypeptide of 27 to 169 amino acids in length comprising a contiguous amino acid sequence of at least 20 amino acids in length, wherein the contiguous sequence is substantially homologous to SEQ. ID. NO. 4. In one embodiment the contiguous amino acid sequence, or contiguous sequence, shares at least 90% sequence homology with SEQ. ID. NO. 4.

In one embodiment the invention provides a polypeptide of 27 to 169 amino acids in length comprising a contiguous amino acid sequence of at least 20 amino acids in length, wherein the contiguous sequence is selected from SEQ. ID. NO. 4, 5, 6, 7, 8, 9, 10, 11, 12, 13, 14, 15, 16, 17, 18, 19, 20, 21, 22, 23, 24, 25, 26, 27, 28, 29, 30, 31, 32, 37, 38, 39, 40, 41, 42, 43, 44, 45, 46, 47 or 48.

One embodiment of the invention relates to polypeptides that comprise SEQ. ID. 4, 5, 6 or 7. Another embodiment of the invention relates to polypeptides that comprise SEQ. ID. 8, 9, 10, 11, 12, 13, 14, 15, 16, 17, 18, 19, 20, 21, 22, 23, 24, 25, 26, 27, 28, 29, 30, 31, 32, 37, 38, 39, 40, 41, 42, 43, 44, 45, 46, 47 or 48.

In a further embodiment of the invention relates to polypeptides that consist of SEQ. ID. 4, 5, 6 or 7. Another embodiment relates to polypeptides that consist of SEQ. ID. 8, 9, 10, 11, 12, 13, 14, 15, 16, 17, 18, 19, 20, 21, 22, 23, 24, 25, 26, 27, 28, 29, 30, 31, 32, 37, 38, 39, 40, 41, 42, 43, 44, 45, 46, 47 or 48.

The polypeptides of the invention can be conjugated to various moieties or labels including fluorescent labels or polypeptide tags as known in the art and described herein. Polypeptides of the invention may further comprise for example Human influenza hemagglutinin (HA) tag, a polyhistidine-tag (his6) or both a HA-tag and his6-tag or an epitope tag such as V5-tag at the polypeptide C-terminus e.g. SEQ. ID NO. 37, 38, 39, 40, 41, 42, 43, 44, 45, 46, 47 or 48.

The present invention provides cell-based assay methods and systems for assessing (i) binding of PCSK9 (SEQ. ID. NO. 1 or a biologically active fragment thereof), to plasma membrane LDLR (SEQ. ID. NO. 2) and (ii) PCSK9 mediated cellular internalization of LDLR in cultured cells mediated by PCSK9-LDLR complex formation.

In one embodiment the invention provides fusion proteins for use in the cell-based assay methods. For example (i) LDLR (SEQ. ID. NO. 2 or a biologically active fragment thereof and (ii) a fluorescent polypeptide including but not limited to mCherry or fluorescent green protein, a fluorescent LDLR fusion protein e.g. SEQ. ID. NO. 77. The invention also provides fusion proteins for use in the cell-based assay methods of the invention comprising (i) PCSK9 (SEQ. ID. NO. 1 or a biologically active fragment thereof), or another polypeptide based PCSK9 analogue and (ii) a fluorescent polypeptide including but not limited to mCherry or fluorescent green protein, a fluorescent PCSK9 fusion protein e.g. SEQ. ID. NO. 75 or 76.

Polypeptides of the invention also include variants, derivatives and conjugates of the polypeptide sequences as disclosed herein.

Polynucleotides, Vectors, Plasmids

The invention also provides polynucleotides encoding the polypeptides of the invention e.g. SEQ. ID. NO. 33, 34, 35, or 36 as well as methods of preparing such polynucleotides or polypeptides; vectors comprising the polynucleotides, host cells for expressing a polypeptide of the invention and uses of such polypeptides for the treatment and screening methods described herein.

Polynucleotides of the invention include a polynucleotide of 81-510 nucleotides in length and comprising SEQ. ID. NO. 33, 34, 35, or 36, 49, 50, 51, 52, 53, 54, 55, 56, 57, 58, 59 or 60. Polynucleotides of the invention include a polynucleotide that encodes a polypeptide of 27 to 169 amino acids in length comprising a contiguous amino acid sequence of at least 20 amino acids in length, wherein the contiguous sequence is substantially homologous to SEQ. ID. NO. 4. Polynucleotides of the invention include a polynucleotide that encodes a polypeptide of 27 to 169 amino acids in length comprising a contiguous amino acid sequence of at least 20 amino acids in length, wherein the contiguous sequence is selected from SEQ. ID. NO. 4, 5, 6, 7, 8, 9, 10, 11, 12, 13, 14, 15, 16, 17, 18, 19, 20, 21, 22, 23, 24, 25, 26, 27, 28, 29, 30, 31, 32, 37, 38, 39, 40, 41, 42, 43, 44, 45, 46, 47 or 48. The invention further includes a vector or plasmids and the like comprising a polynucleotide of the invention, a polynucleotide of 81-510 nucleotides in length and comprising SEQ. ID. NO. 33, 34, 35, or 36, 49, 50, 51, 52, 53, 54, 55, 56, 57, 58, 59 or 60.

The invention also provides polynucleotides encoding the fusion proteins of the invention for use in the cell-based assays and systems disclosed herein. In one embodiment the invention provides polynucleotides encoding a PCSK9-fluorescent polypeptide fusion proteins (e.g. SEQ. ID. NO. 75 or 76). A PCSK9-fluorescent polypeptide fusion protein comprises PCSK (SEQ. ID. NO. 1) or biologically active fragment of PCSK9 fused to fluorescent polypeptide including but not limited to mCherry or eGFP. In another embodiment the invention provides polynucleotides encoding a LDLR-fluorescent polypeptide fusion proteins (e.g. SEQ. ID. NO. 77). A LDLR-fluorescent polypeptide fusion protein comprises LDLR (SEQ. ID. NO. 2) or biologically active fragment of LDLR fused to fluorescent polypeptide including but not limited to mCherry or eGFP.

In one embodiment the invention provides a gene expression vector e.g. pcDNA3, pIRES2 for mammalian cell expression or pET24b+ for recombinant bacterial protein production, comprising a polynucleotide selected from SEQ. ID. NO. 33, 34, 35, 36, 49, 50, 51, 52, 53, 54, 55, 56, 57, 58, 59, 60, 68, 69 or 70. Another embodiment relates to a gene expression vector comprising a polynucleotide that encodes a polypeptide of from 27 to 169 amino acids in length comprising a contiguous amino acid sequence of at least 20 amino acids in length, wherein the contiguous sequence that is at least 90% substantially homologous to SEQ. ID. NO. 4. Another embodiment relates to a gene expression vector comprising a polynucleotide that encodes a fluorescent PCSK9 fusion protein or fluorescent LDLR fusion protein as described herein.

A further embodiment of the invention relates to gene expression vectors that express a polynucleotide of the invention as described herein. Vectors of the invention include vectors comprising a polynucleotide that encodes a polypeptide substantially homologous to a polypeptide of 27 to 169 amino acids in length, wherein the polypeptide comprises a contiguous amino acid sequence that is homologous to SEQ. ID. NO. 4, 5, 6 or 7.

A further embodiment of the invention relates to a cell engineered to express a polypeptide of the invention, in particular cultured cells for manufacturing synthetic polypeptide. The invention also provides mammalian or bacterial cells comprising a vector or polypeptide of the invention. In some embodiments a cell is engineered to express a polypeptide of the by transfecting a bacterial or mammalian cell with a vector of comprising a polynucleotide of the invention. In one embodiment a cell is transfected with a vector comprising SEQ. ID. NO 33, 34, 35, 36, 49, 50, 51, 52, 53, 54, 55, 56, 57, 58, 59 or 60. In another embodiment a cell is transfected with a vector comprising SEQ. ID. NO. 68, 69 or 70.

Methods

The polypeptides of the invention are useful for treating cardiovascular disease associated with elevated circulating lipid levels and elevated cholesterol. In particular, the peptides of the invention can be used to treat atherosclerosis or hyperlipidemia.

In a one embodiment the invention relates to a method of providing anti-atherosclerosis therapy to a subject comprising administering an effective amount of a therapeutic composition comprising a polypeptide of the invention. In a further embodiment the invention relates to a method of providing anti-inflammatory therapy to a subject comprising administering an effective amount of a therapeutic composition comprising a polypeptide of the invention e.g. a polypeptide of 27 to 169 amino acids in length comprising a contiguous amino acid sequence of at least 20 amino acids in length, wherein the contiguous sequence is substantially homologous to SEQ. ID. NO. 4.

The polypeptides of the invention may be administered in the form of a pharmaceutical composition, as defined herein. Preferably, said polypeptide is administered in a therapeutically effective amount. The polypeptides of the invention may be administered orally, intravenously, intra-peritoneally, subcutaneously, parenteral, mucosal, topically or nasally.

The invention provides methods of blocking the activity of PCSK9 in vivo and reducing LDLR internalization comprising administering a therapeutically effective amount of a polypeptide of the invention to a mammal. The invention also provides a method of reducing circulating LDL-cholesterol levels comprising administering a therapeutically effective amount of a polypeptide of the invention to a mammal. Accordingly the invention provides therapeutic compositions and methods for: inducing atherosclerosis regression, slowing progression of atherosclerosis, treating cardiovascular disease including atherosclerosis, treating hyperlipidemia, reducing septic inflammatory response in viral infections, and reducing septic inflammatory response, etc.

In a further embodiment the invention provides a pharmaceutical composition comprising a therapeutically effective amount of a polypeptide of the invention e.g. 27 to 169 amino acids in length comprising a contiguous amino acid sequence of at least 20 amino acids in length, wherein the contiguous sequence is substantially homologous to SEQ. ID. NO. 4.

Pharmaceutical compositions of the invention can be used in combination with other lipid-lowering agent (i.e. statins, fibrates, niacin, dalcetrapib, ezetimibe, PCSK9 inhibitors (monoclonal antibody, siRNA, small molecules, etc.)), non-steroidal anti-inflammatory, anti-coagulants, or anti-atherosclerosis agents (i.e. beta blockers, ACE inhibitors, etc).

Another embodiment the invention relates to polypeptides and pharmaceutical compositions thereof for reducing circulating levels of pathogen lipids that contribute to sepsis. In a related embodiment the invention provides polypeptides and pharmaceutical compositions thereof for treating septic inflammatory response caused by pathogen lipids.

The polypeptides of the invention may be administered in the form of a pharmaceutical composition, as defined herein. Preferably, said polypeptide is administered in a therapeutically effective amount. In a further embodiment the invention provides pharmaceutical compositions or formulations comprising a polypeptide of the invention.

The invention further provides screening methods for identifying agents including but not limited to small molecules, peptidomimetics or antibodies, agents that may compete with a polypeptide of the present invention for binding to PCSK9 and may function to to prevent internalization of PM PCSK9-LDLR complex. In one embodiment the screening method comprises the step of analyzing the extent to which a polypeptide of the invention inhibits PCSK9-related activity and/or function such as increase LDLR levels and LDL clearance.

In another embodiment the screening method comprises the steps of: (i) administering a therapeutically effective amount of a polypeptide of the invention (e.g. 27 to 169 amino acids in length comprising a contiguous amino acid sequence of at least 20 amino acids in length, wherein the contiguous sequence is substantially homologous to SEQ. ID. NO. 4) to a mammal (ii) measuring the lipid-lowering or anti-inflammatory (cytokine and adhesion molecule expression) or anti-atherogenesis (extent of progression or regression of atherosclerotic plaque size) activities of PCSK9 in said animal model. In one embodiment the animal is an animal model such as wild-type mice, and/or hypercholesterolemic mice, genetically modified/humanized mice, non-human primates either on normal diets or high-fat, high-caloric, western diets.

In yet another embodiment the screening method comprises assessing the binding of a polypeptide of the invention to circulating PCSK9, or a fusion protein thereof (e.g. SEQ. ID. NO. 75 or SEQ. ID. NO. 76) by means of a label directly or indirectly associated with the polypeptide. Alternatively, the screening method may involve measuring or, qualitatively or quantitatively, assessing the ability of a polypeptide of the invention to modulate circulating LDL-cholesterol levels, inflammatory response, atherosclerosis regression, viral infection or a biological effect related to PCSK9.

The invention provides a method of preventing or reducing atherosclerosis in a subject diagnosed as having atherosclerosis, or in a subject at risk of developing atherosclerosis, comprising administering to the subject an effective amount of a pharmaceutical composition comprising a polypeptide of the invention.

Subjects considered at risk of atherosclerosis include individuals with chronic inflammation and may include but are not limited to individuals with dyslipidemia including hyperlipidemia, hypertension, diabetes or obesity.

The invention provides a method of reducing risk of coronary heart diseases or controlling inflammation in a subject diagnosed as having hyperlipidemia, premature coronary diseases, at risk of developing coronary diseases or in a condition of sepsis induced by pathogen lipids, comprising administering to the subject an effective amount of a pharmaceutical composition comprising a polypeptide of the invention.

The invention further provides assay methods for screening the activity of therapeutic compositions comprising a polypeptide of the invention e.g. a polypeptide of 27 to 169 amino acids in length comprising a contiguous amino acid sequence of at least 20 amino acids in length, wherein the contiguous sequence is substantially homologous to SEQ. ID. NO. 4. other antibody based on small molecule PCSK9 inhibitors, blockers or modulating agents.

In a further embodiment the screening methods of the invention comprises the step of analyzing the extent to which an agent or test compound reduces plasma membrane levels of PCSK9 or PCSK9-LDLR complex, intracellular levels of PCSK9-LDLR complex or extracellular levels of PCSK9. In another embodiment the screening method comprises the steps of: (i) administering a polypeptide of the invention to an animal and (ii) measuring pro-inflammatory (cytokine and adhesion molecule expression) or pro-atherogenesis (evolution of atherosclerotic plaque size) in said animal model. In yet another embodiment the screening method comprises measuring the binding of a polypeptide of the invention to PCSK9 or a to PCSK9-LDLR complex, or to a PCSK9 fusion protein (e.g. SEQ. ID. NO. 75 or 76). Alternatively, the screening method may involve measuring or, qualitatively or quantitatively, detecting ability of a polypeptide of the invention to modulate the inflammatory, atherogenic, leukocyte adhesion biological mechanisms associated with atherosclerosis OR either in vitro or in vivo.

In a further embodiment the invention provides assay methods, assay systems and assay kits for screening or evaluating agents or test compounds for effects on PCSK9 binding to LDLR or PCSK9 cellular internalization following binding to LDLR or both.

In one embodiment the present invention relates to a cell-based assay system comprising: (i) a PCSK9 molecule conjugated to a first fluorescent protein (PCSK9 fluorescent fusion protein) e.g. SEQ. ID. NO. 75 or 76, (ii) a LDLR molecule conjugated to a second fluorescent protein (LDLR fusion protein) e.g. SEQ. ID. NO. 77, wherein the LDLR conjugate is stably expressed by a hepatic cell line at the plasma membrane and said first and second fluorescent proteins emit at different wavelengths providing at least 3 distinguishable fluorescent signals. Distinguishable fluorescent signals include (1) when both the first and second fluorescent protein are detected, (2) when only the first fluorescent protein is detected or (3) when only the second fluorescent protein is detected A further embodiment is an in vitro method of evaluating the effect of at least 1 test compound on the binding of PCSK9 to an LDLR receptor expressed at the surface of a cultured cell or internalization of PCSK9 by the cell, said method comprising the steps of:

(i) contacting the test compound with an assay system comprising a PCSK9 conjugated to a first fluorescent protein (fluorescent PCSK9 fusion protein), and a cell transformed to express LDLR protein conjugated to a second fluorescent protein (fluorescent LDLR fusion protein) and (ii) detecting a fluorescent signal from the assay system corresponding to said first fluorescent protein, said second fluorescent protein or a combined signal derived from both the first and second fluorescent protein;

wherein the second fluorescent protein is conjugated to the C-terminus of LDLR and located intracellularily and detecting signal: (i) only from the fluorescent PCSK9 conjugate indicates that PCSK9 binding and internalization has not been blocked or inhibited by the test compound, (ii) only from the fluorescent LDLR conjugate indicates that PCSK9 binding to LDLR and internalized has been blocked or inhibited by the test compound and (iii) from the combination of the fluorescent PCSK9 conjugate and fluorescent LDLR conjugate indicates that PCSK9 binding to LDLR was not inhibited or blocked and that PCSK9 internalization was blocked or inhibited internalization by the test compound.

The present invention relates to an in vitro method of evaluating the effect of at least 1 test compound on cellular internalization of PCSK9 following binding of PCSK9 to an LDLR receptor expressed at the cell surface of a cultured cell said method comprising the steps of (i) contacting the test compound with an assay system comprising a PCSK9 conjugated to a first fluorescent protein sequence, and a cell transformed to express a LRLR protein conjugated to a second fluorescent protein sequence and (ii) detecting a fluorescent signal from the assay system corresponding to said first fluorescent protein, said second fluorescent protein or a combined signal derived from both the first and second fluorescent protein.

In a further embodiment, the invention provides an in vitro assay system comprising PCSK9 conjugated to a first fluorescent protein, preferably enhanced green fluorescent protein (eGFR), cultured cells expressing LDLR conjugated to a second fluorescent protein, preferably m-Cherry. In this case the signal from the first fluorescent protein (PCSK9 conjugate) is a red signal, the signal from the second fluorescent protein (LDLR conjugate) is a green and the composite signal is a yellow.

In another embodiment components of the assay system of the invention are in the form of a kit. The assay kit of the invention may comprise a vector or cDNA that encodes a PCSK9 fluorescent conjugate in cultured human cells, a vector or cDNA that encodes LDLR fluorescent conjugate in cultured human cells or purified PCSK9 fluorescent conjugate protein. Assay kits of the invention comprise instructions for use outlining steps of the cell-based dual fluorescence assay described herein for evaluating PCSK9 binding to LDLR or PCSK9 cellular internalization following LDLR binding.

In another broad aspect, the invention provides a method of preventing or treating hyperlipidemia in a subject in need thereof by reducing circulating LDL-cholesterol levels, the method comprising administering to the subject a therapeutically effective amount of a polypeptide comprising a contiguous amino acid sequence of at least 20 amino acids in length, wherein the contiguous amino acid sequence is substantially homologous to SEQ. ID. NO. 4, wherein at least part of the contiguous amino acid sequence is exposed after folding of the polypeptide, wherein the polypeptide is conjugated to one or more polymer moieties, and wherein the polypeptide binds to PSCK9.

Other aspects, embodiments, advantages and application of the invention will become clear from the further description provided herein. The detailed description and examples illustrate the preferred embodiments of the invention however various additional modifications are within the scope of the invention and will be apparent to those skilled in the art in light of the teachings of the present disclosure.

BRIEF DESCRIPTION OF THE DRAWINGS

FIG. 3: GRP94 is not a chaperone for PCSK9. (a) HepG2 cells were incubated overnight without (DMSO) or with 1 or 5 μM Geldanamycin. Total LDLR (SEQ. ID. NO. 2), PCSK9 (SEQ. ID. NO. 1) and β-actin (herein used as control) protein levels in cell lysates and conditioned media were analyzed by immune-blotting as indicated. (b) Left panel; At day 0, HEK293 cells were transfected either with a non-targeting siRNA (−) or with siRNAs against GRP94 (+). Eight hours later, cells were transfected without (pIRES-V5) or with plasmids encoding for PCSK9-V5 or PCSK9-D374Y-V5. At day 2, cells were washed and incubated overnight in conditioned media (DMEM; Cond. Media). PCSK9 was immune-precipitated from cell lysates using mAb-V5 antibody (IP: V5) and immune-blotted (IB) as indicated. Total GRP94, PCSK9, LDLR and β-actin protein levels were analyzed by immune-blotting in cell lysates (input) and conditioned media. Right panel; HepG2 cells were incubated for 24 h in conditioned media derived from HEK293 cells (left panel). Total LDLR, PCSK9-V5 and β-actin protein levels were analyzed by immune-blotting as indicated. Data are representative of at least three to four independent experiments.

FIG. 9: Proposed model for the role of GRP94 in the regulation of LDLR by PCSK9. Left; In the absence or GRP94, proPCSK9 (SEQ. ID. NO. 70) or mature PCSK9 might be more bioavailable for binding LDLR thus leading to enhance degradation and high circulating LDL-C. Right; In the presence of GRP94, LDLR protein levels are elevated most probably by preventing early binding of PCSK9 to LDLR and its subsequent intracellular degradation. Addition of exogenous full-length GRP94 or its CBD-CT in circulation may efficiently be used to reduce circulating LDL-Cholesterol or other PCSK9-related diseases. ER; endoplasmic reticulum, TGN; trans-Golgi network, LE/LY; late endosomes/lysosomes, B; apolipoprotein B, PCSK9; pro-protein convertase subtilisin/kexin 9, LDLR; low-density lipoprotein receptor, LDL; low-density lipoprotein, GRP94; Glucose-regulated protein 94.

FIG. 11: LC-MS analysis of excised bands. Raw data of polypeptides identified by mass spectrometry following as described in FIG. 1*a*.

FIG. 12: LC-MS analysis of excised bands. Raw data of polypeptides identified by mass spectrometry following as described in FIG. 1*b*.

FIG. 13: Oligonucleotides used for plasmid constructions for PCSK9 fluorescent protein conjugate and LDLR fluorescent protein conjugate.

DETAILED DESCRIPTION

Figure 1:
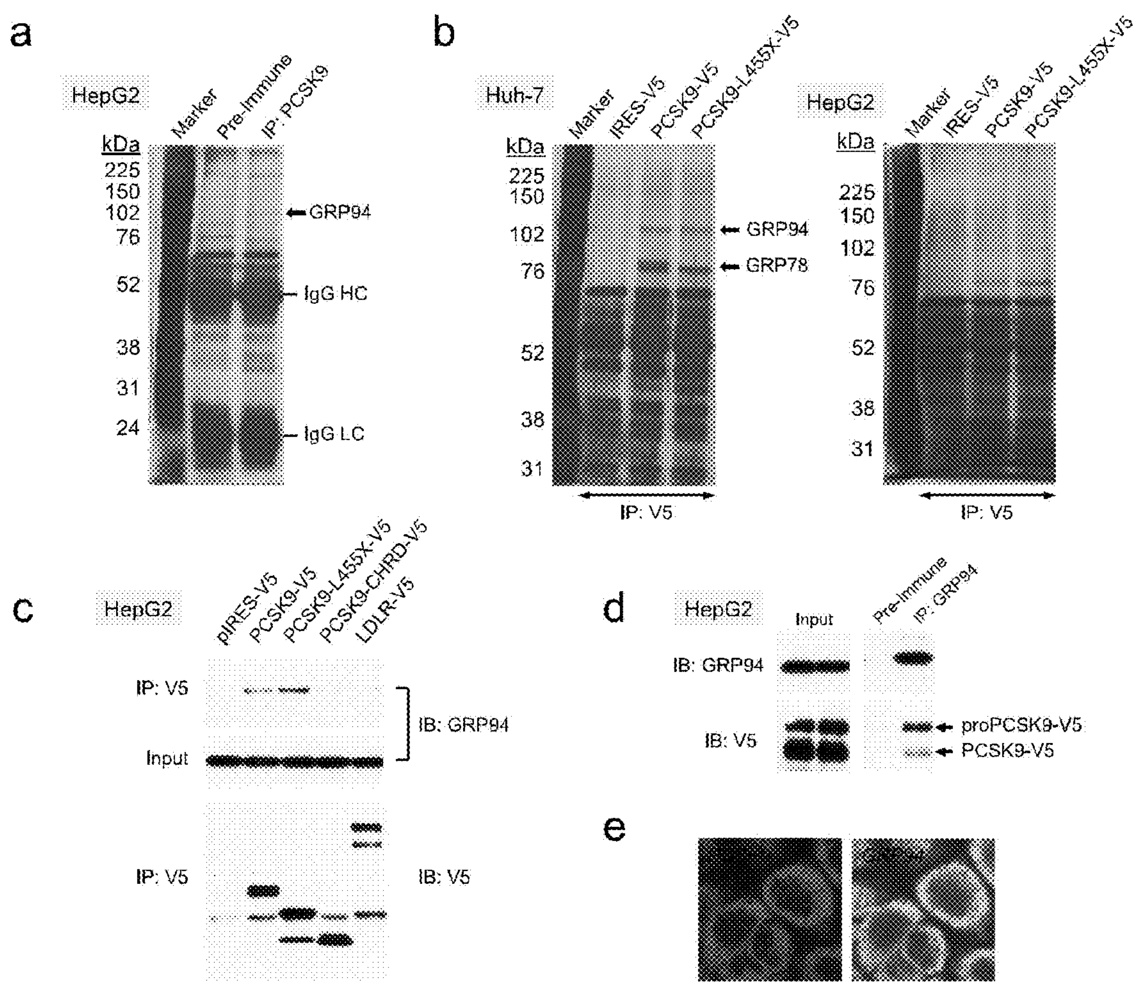
FIG. 1: Identification of GRP94 as a new PCSK9 interacting protein. (a) Endogenous PCSK9 was immunoprecipated from HepG2 cell lysates in RIPA buffer (IP: PCSK9). Pre-immune serum was used as a control. Precipitated protein samples were separated by SDS-PAGE electrophoresis and revealed by silver staining. Excised bands were analyzed by mass spectrometry. (b) Huh-7 and HepG2 cells were transfected without (IRES-V5) or with plasmids encoding either PCSK9-V5 or PCSK9-L455X-V5. PCSK9 (SEQ. ID. NO. 1) was immune-precipitated using mAb-V5 antibody, proteins were separated by SDS-PAGE and revealed by silver staining. GRP94 (SEQ. ID. NO. 3) and GRP78 were identified by mass spectrometry from excised bands. (c) HepG2 cells were transfected without (IRES-V5) or with plasmids encoding various V5-tagged PCSK9 (PCSK9-V5, PCSK9-L455X-V5, PCSK9-CHRD-V5) or human LDLR-V5. V5-tagged proteins were immune-precipitated from cell lysates (IP: V5) and immune-blotted (IB) for GRP94 and V5. Total input GRP94 protein levels were also analyzed by immune-blotting and herein used as a control. (d) HepG2 cells were transfected with PCSK9-V5. GRP94 was immune-precipitated from cell lysates and co-immuno-precipitated PCSK9 was revealed using a mAb-V5 antibody. (e) Subcellular co-localization of PCSK9 and GRP94 in Huh-7 cells was visualized by confocal microscopy. Data are representative of at least three independent experiments.

Unless indicated or defined otherwise, all terms used have their usual meaning in the art to which the present invention relates. Reference is for example made to the standard handbooks, such as Sambrook et al., “Molecular Cloning: A Laboratory Manual”, 4th. Ed. Cold Spring Harbor Laboratory Press (2012); F. Ausubel et al., eds., “Current protocols in molecular biology”, Wiley Interscience, (2012); Lewin, “Genes C”, Jones & Bartlett Learning (2011); and Janeway et al., “Immunobiology” (7th Ed.), Garland Science (2008). The terminology used herein is for the purpose of describing particular embodiments only and is not intended to be limiting.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains. Are also hereby incorporated by reference U.S. provisional patent applications 62/135,668 filed Mar. 19, 2015 and 62/259,621 filed Nov. 24, 2015 from which the present application claims priority. The present application hereby incorporates by reference the material in the text file 20111-185_SEQList 19Mar16_ST25.txt created on Mar. 19, 2016 of size 143,187 bytes and filed concurrently herewith. This text file contains all the sequences mentioned in the present application.

Definitions

Throughout this specification, unless the context requires otherwise, the word “comprise”, or variations such as “comprises” or “comprising”, will be understood to imply the inclusion of a stated element or integer or group of elements, such as a contiguous amino acid sequence within a polypeptide, or integers but not the exclusion of any other element or integer or group of elements or integers.

As used herein the singular forms “a”, “an” and “the” include plural aspects unless the context clearly dictates otherwise. Thus, for example, reference to “a cell” includes a single cell, as well as two or more cells; reference to “an agent” includes one agent, as well as two or more agents; and so forth.

Unless otherwise indicated all methods steps and techniques mentioned herein can be performed in a manner known per se, as will be clear to the skilled person.

Amino acid residues will be indicated according to the standard three-letter or one-letter code, as mentioned in Table 1. Except were specified to the contrary, the amino acids used in the polypeptides of the invention described herein are D stereoisomer's and not L stereoisomers.

TABLE 1

| Characteristics | Amino Acid | 3-letter code | 1-letter code |
|---|---|---|---|
| Non-polar uncharged at pH 6.0-7.0 | Alanine | Ala | A |
| | Valine | Val | V |
| | Leucine | Leu | L |
| | Isoleucine | Ile | I |
| | Phenylalanine | Phe | F |
| | Methionine | Met | M |
| | Tryptophan | Typ | W |
| | Proline | Pro | P |

TABLE 1-continued

| Characteristics | Amino Acid | 3-letter code | 1-letter code |
|---|---|---|---|
| Polar uncharged at pH 6.0-7.0 | Glycine | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar charged at pH 6.0-7.0 | Lysine | Lys | K |
| | Arginine | Arg | R |
| | Histidine | His | H |
| | Aspartate | Asp | D |
| | GlutamateG | Glu | E |
| Synthetic, non natural amino acids | Norleucine | Nle | Z |
| | Citrulline | Cit | |
| | Homocysteine | Hey | |
| | Ornithine | Orn | |

For the purposes of comparing two or more polypeptide sequences, percentage of "sequence identity" between a first amino acid sequence and a second amino acid sequence (also referred to herein as "amino acid identity" or "sequence homology") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%]. Each deletion, insertion, substitution or addition of an amino acid residue in the second amino acid sequence—compared to the first amino acid sequence—is considered as a difference at a single amino acid residue (position). Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Many algorithms exist to determine the degree of identity, homology or similarity between two polypeptides. Usually, the homology can be determined by means of the Lasergene software of the company DNA star Inc., Madison, Wis. (USA), using the CLUSTAL method (Higgins et al, 1989, Comput. Appl. Biosci., 5 (2), 151). Other programs that a skilled person can use for the comparison of sequences and that are based on algorithms are, e.g., the algorithms of Needleman and Wunsch or Smith and Water-man. Further useful programs are the Pile Aupa program (J. MoT Evolution. (1987), 25, 351-360; Higgins et al., (1989), Cabgos, 5, 151-153) or the Gap and Best Fit program (Needleman and Wunsch, (1970), J. MoT Biol, 48, 443-453, as well as Smith and Waterman (1981), Adv., Appl. Math., 2, 482-489) or the programs of the GCG software package of the Genetics Computer Group (575 Science Drive, Madison, Wis., USA 53711). Sequence alignments can also be performed with the ClustalW program from the internet page http://www.ebi.ac.uk/clustalw or with the NCBI Blast Sequence alignment program from the internet page www.ncbi.nlm.nih.gov/BLAST/or www.ncbi.nlm.nih.gov/blast/b12seq/wblast2.cgi. Also, the skilled person is aware of the techniques which allow him to isolate homologous sequences from other organisms. He can perform homology comparisons (via CLUSTAL, BLAST, NCBI) and then isolate the identified homologous nucleotide or amino acid sequences by means of standard laboratory methods, e.g. primer design, PCR, hybridisation or screening of cDNA libraries with adequate probes (cf. e.g. Sambrook and Russell (2001) Molecular Cloning: A Laboratory Manual, 3. edition, Cold Spring Harbour Laboratory Press, Cold Spring Harbour, N.Y., USA). The function of the identified proteins can then be determined by the method described herein.

In determining the degree of sequence identity or percent homology between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. In Particular preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Len or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Alternately amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Nad. Acad. Sci. USA 81: 140-144, 1984; Kyte & Doolittle; J. Molec. Biol. 157: 105-132, 198 I, and Goldman et al., Aim. Rev. Biophys. Chem. 15: 321-353, 1986, all incorporated herein in their entirety by reference.

"amino acid" refers to either natural and/or non-natural or synthetic amino acids, including glycine and both the D or L optical isomers, and amino acid analogs and peptidomimetics.

Peptides of the invention e.g. a polypeptide of 27 to 169 amino acids in length comprising a contiguous amino acid sequence of at least 20 amino acids in length, wherein the contiguous sequence is substantially homologous to SEQ. ID. NO. 4. can be referred to as "PCSK9 modulator" or "PCSK9 binding polypeptide" or "GRP94 polypeptide analogue".

Polypeptides of the invention bind to PCSK9 or a PCSK9-LDLR conjugate in vitro or in vivo and after binding function to prevent or slow internalization of PCSK9 or PCSK9-LDLR from the plasma membrane of hepatic cells into the cell. By virtue of this function peptides of the invention thereby increase cell surface levels of LDLR.

"Anti-atherosclerotic agent" means a polypeptide or a composition or formulation thereof that has an anti-atherosclerotic effect in vivo.

The term "antibody" is used herein in the broadest sense and specifically covers intact monoclonal antibodies, polyclonal antibodies, multi-specific antibodies (e.g. bi-specific antibodies) formed from at least two intact antibodies, and antibody fragments. "Antibody fragments" comprise only a portion of an intact antibody, generally including an antigen binding site of the intact antibody and thus retaining the ability to bind antigen. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed usually against a single antigen.

"anti-inflammatory agent" means an polypeptide or a composition or formulation thereof that has an anti-inflammatory effect in vivo "Atherogenesis" as used herein means the development process of atheromatous plaques characterized by remodelling of arteries leading to sub-endothelial accumulation of fatty substances or plaques containing excess fat, collagen and elastin. This process involves inflammation and the formation of atheromatous plaques in the region of the vessel wall located between the endothelium and the tunica media. The early stages of atherogenesis are characterized by adhesion of circulating monocytes to the vascular endothelium, migration of these monocytes into the sub-endothelial space and activation of monocyte-derived macrophages. The key driver of this process is oxidized lipoprotein particles such as low-density lipoprotein (LDL) residing within the endothelial wall of the vessel. Active atherogenesis can be present in a subject either at risk of atherosclerosis or with atherosclerosis. When active atherogenesis is detected in a subject, it may indicate either risk of atherosclerosis or with atherosclerosis. Distinguish between risk of atherosclerosis or a diagnosis of atherosclerosis, based on a variety of well-known diagnostic measures and atherosclerosis risk factors, is within the current skill in the art of cardiovascular medical care. Identifying the presence of active atherogenesis in a subject and can facilitate early diagnosis, prevention or treatment of atherosclerosis.

"Atherosclerosis" also known as arteriosclerotic vascular disease (ASVD) is characterized by a thickening of an arterial wall as a result of the accumulation of fatty materials such as cholesterol and triglyceride occurring due to atherogenesis. Atherosclerosis is a chronic disease that is asymptomatic for decades. Atherosclerotic plaques can be either stable or unstable (also called vulnerable). Stable plaques are typically asymptomatic. Unstable plaques are prone to rupture leading to intra-luminal thrombi, occluded arteries, coronary occlusion and stroke. The complications of advanced atherosclerosis are chronic, slowly progressive and cumulative. Commonly, vulnerable plaques can suddenly rupture, causing the formation of a thrombus that will rapidly slow or stop blood flow, quickly leading to death of the tissues fed by the blocked artery. This event is called an infarction, such as a myocardial infarction. Atherosclerosis can affect any part of the arterial system, but primarily occurs in larger, high-pressure vessels such as the coronary, renal, femoral, cerebral, and carotid arteries.

A "control" is an alternative subject or sample used in an experiment for comparison purpose. A control can be "positive" or "negative". For example, where the purpose of the experiment is to determine a correlation of an altered expression level of a gene with atherosclerosis or atherogenesis, it is generally preferable to use a positive control (a subject or a sample from a subject, carrying such alteration and exhibiting syndromes characteristic of atherosclerosis or atherogenesis), and a negative control (a subject or a sample from a subject lacking the altered expression and syndromes characteristic of atherosclerosis or atherogenesis).

An "expression vector" is a polynucleotide which, when introduced into an appropriate host cell, can be transcribed and translated into one or more polypeptide(s). An "expression system" usually connotes a suitable host cell comprised of an expression vector that can function to yield a desired expression product e.g. cloning of SEQ. ID. NO. 5, 6 or 7 into pET24b+ bacterial expression vector, which is transferred into appropriate bacterial cells (e.g. *E. Coli*), induction with IPTG and subsequent purification by chromatography).

"Half-life" or "serum half-life" means the time taken for the serum concentration of a polypeptide to be reduced by 50%, in vivo, for example due to the degradation, cleavage, clearance or sequestration of the polypeptide by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomologus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to Dennis et al., J. Biol. Chem. 277:35035-42 (2002), and to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. Edition (1982). As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both. For example, the half-life of an amino acid sequence or polypeptide of the invention may be determined by means of a pharmacokinetic study, performed in a rodent or non-human primate model, as follows. Groups of animals (n=2-10) are given an intravenous bolus injection of 1 mg/kg or 10 mg/kg 2D3-17D12 fusion protein. Plasma samples are obtained via a vein at different time-points after dosing (eg. 1, 2, 4, 6, 8, 12, 24, 48, 144, 192, 240, 288 and 336 h after dosing) and analyzed for the presence of the 2D3-17D12 fusion protein by ELISA. Plasma concentration versus time is fitted to a two-compartment elimination model. The pharmacokinetic parameters of clearance, V1, steady state volume (Vss), T½, AUC, and AUC corrected for actual dose administered (AUC/dose) are averaged for each treatment group. Differences between groups are determined by analysis of variance.

"Inhibition of PCSK9 expression" as used herein means a decrease or absence in the level of PCSK9 protein and/or PCSK9/LDLR complex formation. The consequences of this inhibition can be confirmed by examination of the outward properties of the cell or organism or by biochemical techniques such as antibody binding, enzyme linked immune-sorbent assay (ELISA), western blotting, radioimmunoassay (RIA), other immunoassays, fluorescence activated cell analysis (FACS), Dil-LDL internalization. Differential expression at the protein level can be determined using agents that specifically bind to the encoded protein product, in e.g., an immunoassay. PCSK9 or PCSK9-LDLR activity, its biological effects on endothelial cells, arteries, skeletal muscle, adipocytes, heart, or liver can be determined using the methods described herein as well as by methods known by those skilled in the art. In determining a reduction in the internalization of PCSK9 or PCSK9-LDLR complex mediated by a polypeptide of the present invention, measurements of PM PCSK9 or PCSK9-LDLR levels made after administration a polypeptide of the invention are compared to measurements made in the same subject before administration of a polypeptide of the invention, or are compared to a corresponding normal or pathological range of levels.

"Modulating" PCSK9 or PCSK9-LDLR complex using a polypeptide of the invention may also involve effecting a change (which may either be an increase or a decrease) in affinity, avidity, specificity and/or selectivity of PCSK9 for one or more of its ligands, binding partners, partners affecting PCKS9 association with a homomultimeric or heteromultimeric form, or substrates; and/or effecting a change in the sensitivity of PCSK9 to one or more conditions (such as pH, ion strength, the presence of co-factors, etc.), compared to the same conditions in the absence of a polypeptide of the invention (e.g. a polypeptide of 27 to 169 amino acids in length comprising a contiguous amino acid sequence of at least 20 amino acids in length, wherein the contiguous sequence is substantially homologous to SEQ. ID. NO. 4). "Modulating" PCSK9 or PCSK9-LDLR complex using a polypeptide of the invention also refers to effecting a change with respect to one or more biological or physiological mechanisms, effects, responses, functions, or activities in which PCSK9 is involved, in particular those related to internalization of PCSK9 through clathrin pits, PCSK9 binding to LDLR. Again, as will be clear to the skilled person, the change effected may be determined in any suitable manner and/or using any suitable (in vitro and usually cellular or in vivo assay) assay known per se. In particular, the intended biological or physiological activity affected is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention. Modulating may also involve allosteric modulation of PCSK9; thereby reducing the binding of PCSK9 to binding ligand or partner i.e. LDLR, ApoER2, VLDLR, in particular preventing PCSK9 binding with LDLR, ApoER2, VLDLR.

"Non-natural amino acids" are analogues of the naturally occurring amino acids (Table 1) in that they are derived from a naturally amino acid by chemical variation of the side chain of a standard amino acid. A polypeptide of the present invention (e.g. a polypeptide of 27 to 169 amino acids in length comprising a contiguous amino acid sequence of at least 20 amino acids in length, wherein the contiguous sequence is substantially homologous to SEQ. ID. NO. 4) may contain conservative substitutions of amino acid residues including equivalent non-natural amino acids. Non-natural amino acids encompass a variety of substances and examples for nonstandard amino acids include but are not limited to molecules selected from the group consisting of O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcP-serine, an L-Dopa, a fluorinated phenylalanine, isopropyl-L-phenylalanine, p-azido-L-phenylalanine, p-acyl-L-phenylalanine, p-benzoyl-L-phenylalanine, L-phospho-serine, phosphonoserine, phosphonotyrosine, p-iodo-phenylalanine, homopropargylglycine, azidohomoalanine, p-bromophenylalanine, p-amino-L-phenylalanine and isopropyl-L-phenylalanine. Additionally, other examples of non-natural amino acids optionally include but are not limited to an non-natural analogue of a tyrosine amino acid; an non-natural analogue of a glutamine amino acid, an non-natural analogue of a phenylalanine amino acid, an non-natural analogue of a serine, an non-natural analogue of a threonine, an non-natural analogue of an arginine analogue, an non-natural analogue of an asparagine, an non-natural analogue of a glycine, an non-natural analogue of a valine, an non-natural analogue of a methionine, an non-natural analogue of a lysine, an non-natural analogue of a glutamine, an alkyl, aryl, acyl, azido, cyano, halo, hydrazine, hydrazide, hydroxyl, alkenyl, alkynl, ether, thiol, sulfonyl, seleno, ester, thio-acid, borate, boronate, phospho, phosphono, phosphine, heterocyclic, enone, imine, aldehyde, hydroxylamine, keto, or amino substituted amino acid, or any combination thereof.

Amino acids of the polypeptide of the invention can also be conjugated with a photo-activatable cross-linker; a spin-labeled amino acid; a fluorescent amino acid; an amino acid with a novel functional group; an amino acid that covalently or non-covalently interacts with another molecule; a metal binding amino acid; a metal-containing amino acid; a radioactive amino acid; a photocaged amino acid; a photoisomerizable amino acid; a biotin or biotin-analogue, preferably at the C- or N-terminus of the polypeptide. Polypeptides of the invention may be conjugated to containing a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an a-hydroxy containing acid; an amino thio acid containing amino acid; an $\alpha,\alpha$-disubstituted amino acid; a $\beta$-amino acid; and a cyclic amino acid other than pro-line. Further examples and more information can be taken for example from "Engineering the genetic code" by Budisa (2005, Wiley-VCH, Weinheim, Germany) or from US 2011/027867.

The terms "polynucleotide", or "oligonucleotide" as used herein refer to a polymeric form of nucleotides of any length, either deoxyribonucleotides or ribonucleotides, analogs or modified forms thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides as well as plasmids, vectors comprising a nucleic acid encoding a polypeptide of the invention. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Substantially homologous nucleotides" "substantially homologous oligonucleotides" or "substantially homologous polynucleotides" are at least about 80% identical with each other, after alignment of the homologous regions. Preferably, the sequences are at least about 85% identical; more preferably, they are at least about 90% identical; more preferably, they are at least about 95% identical; still more preferably, the sequences are 100% identical. Sequence alignment and homology searches can be determined with the aid of computer methods. A variety of software programs are available in the art. Non-limiting examples of these programs are Blast, Fasta (Genetics Computing Group package, Madison, Wis.), DNA Star, MegAlign, Tera-BLAST (Timelogic) and GeneJocky. Any sequence databases that contains DNA sequences corresponding to a target gene or a segment thereof can be used for sequence analysis. Commonly employed databases include but are not limited to GenBank, EMBL, DDBJ, PDB, SWISS-PROT, EST, STS, GSS, and HTGS. Common parameters for determining the extent of homology set forth by one or more of the aforementioned alignment programs include p value and percent sequence identity. P value is the probability that the alignment is produced by chance. For a single alignment, the p value can be calculated according to Karlin et al. (1990) Proc. Natl. Acad. Sci 87: 2246. For multiple alignments, the p value can be calculated using a heuristic approach such as the one programmed in Blast. Percent sequence identity is defined by the ratio of the number of nucleotide matches between the query sequence and the known sequence when the two are optimally aligned. To determine that nucleotide sequences are substantially homologous, it is useful to first establish the lowest temperature at which only homologous hybridization occurs with a particular concentration of salt (e.g., SSC or SSPE). Then, assuming that 1% mismatching results in a 1° C. decrease in the Tm, the temperature of the final wash in the hybridization reaction is reduced accordingly (for example, if sequences having >95% identity are sought, the final wash temperature is decreased by 5° C.). In practice, the change in Tm can be between 0.5° C. and 1.5° C. per 1% mismatch.

The term "polypeptide" and "peptide" are used interchangeably herein. Also encompassed by this definition of "polypeptide" are substantially homologous homologs thereof, wherein homologs have sustainably similar functional properties and biological activity. For example as used herein a "polypeptide of the invention e.g. SEQ. ID. NO. 10" includes polypeptides that are substantially homologous to SEQ. ID. NO. 10, in particular a polypeptide that is at least 90% homologous, and has the same functional properties or biological activity as SEQ. ID. NO. 10. Polypeptides of the invention may be produced by any technique known in the art, such as without limitation, any chemical, biological, genetic or enzymatic technique, either alone or in combination(s). Knowing the amino acid sequence of the desired sequence, one skilled in the art can readily produce said polypeptides, by standard techniques for production of polypeptides. For instance, they can be synthesized using well-known solid phase method, preferably using a commercially available polypeptide synthesis apparatus (such as that made by Applied Biosystems, Foster City, Calif.) and following the manufacturer's instructions. Alternatively, the polypeptides of the invention can be synthesized by recombinant DNA techniques as is now well-known in the art. For example, these fragments can be obtained as DNA expression products after incorporation of DNA sequences encoding the desired polypeptide into expression vectors and introduction of such vectors into suitable eukaryotic or prokaryotic host cells, transfection of a host cell. A transfected host cell, preferably a bacterial or mammalian cell will express the desired polypeptide, from which they can be later isolated using well-known techniques. An expressed polypeptide may be linear or branched polymer, it may comprise modified amino acids, and it may be interrupted by non-natural amino acids. The term "polypeptide" also encompass an amino acid polymer that has been modified; for example, disulfide bond formation, glycosylation, lipidation, acetylation, phosphorylation, or any other manipulation, such as conjugation with a labeling component.

The term "sample" includes any biological sample taken from a patient or individual including a cell, tissue sample or body fluid. For example, a sample may include blood, biopsy sample, synovial fluid or cerebrospinal fluid. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid and lymphatic fluid.

The term "subject" includes, without limitation, humans and non-human primates, animal models, knock-out mice, livestock animals, companion animals, laboratory test animals, captive wild animals, reptiles and amphibians, fish, birds, and any other organism. The most preferred subject of the present invention is a human. A subject, regardless of whether it is a human or non-human organism may be referred to as an individual or subject.

Polypeptides of the invention also include any one of the polypeptide sequences described herein further comprising one or more of modifications to the N terminus, as described herein. Polypeptides of the invention also include any one of the polypeptide sequences described herein further comprising a modification to one or more amino acid side chains e.g. pegylation as described herein. Polypeptide variants or substantially homologous polypeptides may include 1, 2, 3 or more conservative amino acid substitutions, according to Table 2 herein, of a reference polypeptide e.g. SEQ. ID. NO. 4, 5, 6 or 7 and having substantially similar binding, and biological effects compared to the reference polypeptide. In such cases, the polypeptide variant and the reference polypeptide (e.g. SEQ. ID. NO. 4, 5, 6 or 7) are substantially homologous. A conservative change may include a substitution, addition or deletion. A conservative substitution is the substitution of an amino acid for another amino acid with similar chemical properties, similar size, charge, polarity. Basic amino acids—histidine (His or H), arginine (Arg or R), and lysine (Lys or K)—are hydrophilic amino acids with a side chain PK value greater than 7 which is typically positively charged a physiological pH. Polar hydrophilic amino acids—serine, threonine, cysteine, tyrosine, asparagine, and glutamine—are hydrophilic having a side chain that is uncharged at physiological pH. Hydrophobic non-polar amino acids—proline (Pro or P), isoleucine (Ile or I), phenylalanine (Phe of F), valine (Val or V), leucine (Leu or L), tryptophan (Trp or W), methionine (Met or M), alanine (Ala or A) and glycine (Gly or G)—exhibit a hydrophobicity of greater than zero. Acidic amino acids—glutamate (Glu or E) and aspartate (Asp or D)—have a side chain PK value less than 7 and are typically negatively charged a physiological pH. The position of conservative substitutions of SEQ. ID. NO. 10, 12 and 13 is provided in Table 2.

The term "therapeutically effective amount" refers to an amount of a pharmaceutical composition effective to treat a disease or condition in a subject. A therapeutically effective amount of a polypeptide of the invention can be used to effectively treat or to prevent atherosclerosis at a reasonable benefit/risk ratio applicable to any medical treatment. A therapeutically effective amount of a polypeptide of the invention can reduce atherosclerotic plaque burden or slow its evolution as well as reduce the inflammatory load of a subject. These measures of efficacy against atherosclerosis can be measured using methods well known in the art. It is within the capabilities of a skilled medical practitioner to determine the appropriate dosage for an individual patient in view of the patent's size, age, sex, weight, general health, disease progression and previous or current experience of side effects.

"Treatment of" or "to treat" a patient in the sense of the invention are to be understood according to its meaning in the art, in particular according to its meaning in medicine and pharmacy and include both treating a patient suffering from a condition or disease associated with chronic or excessive lipid association inflammation or atherogenesis or preventing lipid association inflammation or atherogenesis.

"Fluorophore" or "fluorescent protein" or "fluorescent protein conjugate" as used herein refers to a fluorescent protein moiety conjugated directly to PCSK-9 or LDLR that can be expressed by a cell in vitro as a single transcript following transformation of the cell with a plasmid or vector encoding the conjugate protein. In the methods and assay system of the invention one type of fluorophore is conjugated to the C-terminus of PCSK9, preferably m-Cherry or any similar photostable fluorophore that can be used to provide a dual signal in a cell-based assay. A dual signal meaning each of the 2 fusion proteins provides a distinct fluorescent signal. A PCSK9 fluorophore conjugate is referred to herein as "PCSK9 fluorescent conjugate" or "PCSK9 fusion protein". In one embodiment PCSK9 is conjugated to mCherry providing a PCSK9 fluorescent conjugate. A second fluorophore is conjugated to the intracellular C-terminus of LDLR. In one embodiment LDLR is conjugated to eGFP providing a "LDLR fluorescent conjugate" or a "LDLR fusion protein".

Examples of combinations of fluorescent PCSK9 conjugate (PCSK9 fusion proteins) and fluorescent LDLR conjugates (LDLR fusion proteins) that could be used to provide a dual signal in the assay of the invention include: PCSK9-mCherry/LDLR-EGFP and PCSK9-DsRed/LDLR-EGFP; PCSK9-mCherry/LDLR-YFP and PCSK9-DsRed/LDLR-YFP; PCSK9-EGFP/LDLR-mCherry and PCSK9-EGFP/LDLR-DsRed; PCSK9-YFP/LDLR-mCherry and PCSK9-YFP/LDLR-DsRed. Sequences corresponding to fluorophores for use in the invention as described include those corresponding to Green fluorescent protein (NCBI Accession: P42212.1, GI: 1169893), GFP-like fluorescent chromoprotein FP538; AltName: Full=zFP538; Contains: RecName: Full=GFP-like fluorescent chromoprotein FP538 chain 1; Contains: RecName: Full=GFP-like fluorescent chromoprotein FP538 chain 2 (NCBI Accession: Q9U6Y4.1 GI: 56749101), Yellow fluorescent protein; Short=YFP (NCBI Accession: P21578.1, GI: 126535), GFP-like fluorescent chromoprotein FP506; AltName: Full=zFP506 (Accession: Q9U6Y5.1 GI: 56749102), or GFP-like non-fluorescent chromoprotein; AltName: Full=Non-fluorescent pocilloporin; AltName: Full=Rtms 5 (NCBI Accession: P83690.2 GI: 55976263).

As used herein "agent" means a small molecule, antibody or other biological molecule that has or could have effects on the binding of PCSK9 to LDLR or internalization of PCSK9-LDLR complex either in vivo or in an in vitro cell-based assay. One type of agent is a 'test compound' or 'test agent'. 'Test compound' or 'test agent' refers to an agent screened in an in vitro assay.

As used herein "dual signalling" or "dual fluorescent signalling" refers to a detection of multiple distinct fluorescent signals in a cell based assay such as: a signal corresponding to a $1^{st}$ fluorophore conjugated to PCSK9, a signal corresponding to a $2^{nd}$ fluorophore conjugated to PCSK9 and a $3^{rd}$ distinct type of signal corresponding to a signal derived from both a first and second fluorophore in combination wherein the first and second fluorophore emission wave lengths are different.

"PCKS9 inhibitor" as used herein refers to any small molecule compound, polypeptide, antibody, antibody fragment or other biologic that inhibits either directly or indirectly binding of PCSK9 to LDLR or internalization (e.g. into a hepatic cell) of PCSK9 following binding to LDLR. Examples of PCSK9 inhibitors include anti-PCSK9 antibodies, adnectin, Repatha®/Evolocumab (Amgen); Praluent®/Alirocumab (Regeneron-Sanofi); Bococizumab (Pfizer, Phase III); LGT209 (Novartis, Phase II); RG7652 (Roche/Genentech, Phase II); BMS-972476 (BMS; Adnectin, pre-clinical).

"PCSK9 protein" or "PCSK9 molecule" as used herein means a mammalian PCSK9 protein or any genetic variant thereof including both naturally occurring variants or man-made designed variants or fragments of a mature PCSK9 protein sequence. In the assay methods and systems of the invention PCSK9 is conjugated to a fluorescent protein such that a fluorescent, biologically active PCSK9 protein conjugate is created. Such conjugates are referred to herein as a fluorescent PCSK9 conjugate protein or a PCSK9 fusion protein. A variety of PCSK9 variant proteins are known in the art including but not limited to the sequences corresponding to the PCSK9 protein sequences provided in UniProtKB—Q8NBP7, these sequences are herein incorporated by reference. PCSK9 proteins include PCSK9 variant sequences including but not limited to those corresponding to corresponding to rs28942111, rs28942112, wild-type human PCSK9 (UniProtKB-Q8NBP7) GOF variants hypercholesterolemia (HCHOLA3): S127R (VAR_017199), D129G (VAR_058524), R215H (VAR_058526), F216L (VAR_017200), R218S (VAR_058527), R357H (VAR_058530), D374H (VAR_058531), D374Y (VAR_058532), R496W (VAR_058534).

"LDLR protein" or "LDLR molecule" as used herein means a mammalian LDLR protein or any genetic variant thereof including both naturally occurring variants or man-made designed variants or fragments of a mature LDLR protein sequence. In the assay methods and systems of the invention LDLR is conjugated to a fluorescent protein such that a fluorescent, biologically active LDLR protein conjugate is created. Such conjugates are referred to herein as a fluorescent LDLR conjugate protein or a LDLR fusion protein. A variety of LDLR variant proteins are known in the art including but not limited to the sequences corresponding to Low-density lipoprotein receptor; e.g. Short=LDL receptor; Precursor (NCBI Accession: P01130.1, GI: 126073) or a biologically active fragment or variant thereof. Other proteins similar to LDLR in function including but not limited to: Very low-density lipoprotein receptor; Short=VLDL receptor; Short=VLDL-R; Flags: Precursor (NCBI Accession: P98156.1 GI: 1730112) a biologically active variant or fragment thereof; Low-density lipoprotein receptor-related protein 8; Short=LRP-8; AltName: Full=Apolipoprotein E receptor 2; Flags: Precursor (NCBI: Accession: Q14114.4, GI: 259016389) a biologically active variant or fragment thereof, Lysosome membrane protein 2; AltName: Full=85 kDa lysosomal membrane sialoglycoprotein; Short=LGP85; AltName: Full=CD36 antigen-like 2; AltName: Full=Lysosome membrane protein II; OR Short=LIMP II; AltName: Full=Scavenger receptor class B member 2; AltName: CD_antigen=CD36 (NCBI: Accession: Q14108.2 GI: 2498525) a biologically active variant or fragment thereof, can be used in the assays method, systems and kits of the invention in a manner analogous to LDLR, as described herein.

Polypeptides of the Invention

The endoplasmic reticulum (ER) plays a central role in the production, assembly, and modification of cholesterol, lipids, cell surface receptors and secretory proteins. Under physiological or stress conditions, ER function maintains cellular integrity with the help of crucial factors such as calnexin/calreticulin, GRP78, GRP94, PDI, etc. Glucose-regulated protein 94 (SEQ. ID NO. 2; GRP94) is a highly abundant ER-resident protein well known to function as a molecular chaperone with a restricted number of client proteins, including PCSK9 (Lee, 2014; McLaughlin and Vandenbroeck, 2011). GRP94 (SEQ. ID. NO. 3) also known as heat shock protein 90 (HSP90) is also major luminal calcium-binding protein in the ER (Macer and Koch, 1988). As compared to GRP78, (Jorgensen et al., 2000) GRP94 does not directly bind to LDLR (Pena et al., 2010; Weekes et al., 2012). The polypeptides of the present invention are derived from the GRP94 CDB-CT domain (SEQ. ID. NO. 6). While the polypeptides of the invention could hypothetically occur intracellularily during degradation of GRP94, do not occur outside the cell (extracellularily) and do not naturally function to bind plasma membrane located LDLR and block LDLR internalization.

Polypeptides of the invention range from 27 to 169 amino acids in length comprising a contiguous amino acid sequence of at least 20 amino acids in length, wherein the contiguous sequence is substantially homologous to SEQ. ID. NO. 4.

Polypeptides of the invention include substantially homologous polypeptides of as described herein. In one embodiment a substantially homologous polypeptides may comprise 1, 2 or 3 conservative amino acid substitutions selected from those provided in Table 2 below. Possible conservative substitutions, that can be included in a polypeptide of the invention, are indicated in Table 2. Amino acids are indicated using the one letter code according to Table 1 herein.

TABLE 2

Possible Conservative Amino Acid Substitutions of the Polypeptides of the Invention

| Sequence | Conc. Subst | Position on SEQ. ID. NO. 6 | Position on SEQ. ID. NO. 5 | Position on SEQ. ID. NO. 4 |
|---|---|---|---|---|
| M | M/Z | | 1 | |
| R | R/K | | 2 | |
| A | A/V | | 3 | |
| L | L/I | | 4 | |
| W | | | 5 | |
| V | V/A | | 6 | |
| L | L/I | | 7 | |
| G | | | 8 | |
| L | L/I | | 9 | |
| C | | | 10 | |
| C | | | 11 | |
| V | V/A | | 12 | |
| L | L/I | | 13 | |
| L | L/I | | 14 | |
| T | T/S | | 15 | |
| F | | | 16 | |
| G | | | 17 | |
| S | S/T | | 18 | |
| V | V/A | | 19 | |
| R | R/K | | 20 | |
| A | A/V | | 21 | |
| Y | | 1 | 22 | 1 |
| G | | 2 | 23 | 2 |
| W | | 3 | 24 | 3 |
| S | S/T | 4 | 25 | 4 |
| G | | 5 | 26 | 5 |
| N | | 6 | 27 | 6 |
| M | M/Z | 7 | 28 | 7 |
| E | | 8 | 29 | 8 |
| R | R/K | 9 | 30 | 9 |
| I | I/L | 10 | 31 | 10 |
| M | M/Z | 11 | 32 | 11 |
| K | | 12 | 33 | 12 |
| A | A/V | 13 | 34 | 13 |
| Q | Q/D | 14 | 35 | 14 |
| A | | 15 | 36 | 15 |
| Y | | 16 | 37 | 16 |
| Q | Q/D | 17 | 38 | 17 |
| T | | 18 | 39 | 18 |
| G | | 19 | 40 | 19 |
| K | K/R | 20 | 41 | 20 |
| D | | 21 | 42 | 21 |
| I | I/L | 22 | 43 | 22 |
| S | S/T | 23 | 44 | 23 |
| T | T/S | 24 | 45 | 24 |
| N | | 25 | 46 | 25 |
| Y | | 26 | 47 | 26 |
| Y | | 27 | 48 | 27 |
| A | A/V | 28 | | |
| S | S/T | 29 | | |
| Q | Q/D | 30 | | |
| K | K/R | 31 | | |
| K | K/R | 32 | | |
| T | T | 33 | | |
| F | F | 34 | | |
| E | E | 35 | | |
| I | I/L | 36 | | |
| N | N | 37 | | |
| P | P | 38 | | |
| R | R/K | 39 | | |
| H | H | 40 | | |
| P | P | 41 | | |
| L | L/I | 42 | | |
| I | I/L | 43 | | |
| R | R/K | 44 | | |
| D | D/Q | 45 | | |
| M | M/Z | 46 | | |
| L | L/I | 47 | | |
| R | R/K | 48 | | |
| R | R/K | 49 | | |
| I | I/L | 50 | | |
| K | K/R | 51 | | |
| E | E | 52 | | |

TABLE 2-continued

Possible Conservative Amino Acid Substitutions of the Polypeptides of the Invention

| Sequence | Conc. Subst | Position on SEQ. ID. NO. 6 | Position on SEQ. ID. NO. 5 | Position on SEQ. ID. NO. 4 |
|---|---|---|---|---|
| D | D/Q | 53 | | |
| E | E | 54 | | |
| D | D/Q | 55 | | |
| D | D/Q | 56 | | |
| K | K/R | 57 | | |
| T | T | 58 | | |
| V | V/A | 59 | | |
| L | L/I | 60 | | |
| D | D/Q | 61 | | |
| L | L/I | 62 | | |
| A | A/V | 63 | | |
| V | V/A | 64 | | |
| V | V/A | 65 | | |
| L | L/I | 66 | | |
| F | F | 67 | | |
| E | E | 68 | | |
| T | T | 69 | | |
| A | A/V | 70 | | |
| T | T | 71 | | |
| L | L/I | 72 | | |
| R | R/K | 73 | | |
| S | S/T | 74 | | |
| G | G | 75 | | |
| Y | Y | 76 | | |
| L | L/I | 77 | | |
| L | L/I | 78 | | |
| P | P | 79 | | |
| D | D/Q | 80 | | |
| T | T | 81 | | |
| K | K/R | 82 | | |
| A | A/V | 83 | | |
| Y | Y | 84 | | |
| G | G | 85 | | |
| D | D/Q | 86 | | |
| R | R/K | 87 | | |
| I | I/L | 88 | | |
| E | E | 89 | | |
| R | R/K | 90 | | |
| M | M/Z | 91 | | |
| L | L/I | 92 | | |
| R | R/K | 93 | | |
| L | L/I | 94 | | |
| S | S/T | 95 | | |
| L | L/I | 96 | | |
| N | N | 97 | | |
| I | I/L | 98 | | |
| D | D/Q | 99 | | |
| P | P | 100 | | |
| D | D/Q | 101 | | |
| A | A/V | 102 | | |
| K | K/R | 103 | | |
| V | V/A | 104 | | |
| E | E | 105 | | |
| E | E | 106 | | |
| E | E | 107 | | |
| P | P | 108 | | |
| E | E | 109 | | |
| E | E | 110 | | |
| E | E | 111 | | |
| P | P | 112 | | |
| E | E | 113 | | |
| E | E | 114 | | |
| T | T | 115 | | |
| A | A/V | 116 | | |
| E | E | 117 | | |
| D | D/Q | 118 | | |
| T | T | 119 | | |
| T | T | 120 | | |
| E | E | 121 | | |
| D | D/Q | 122 | | |
| T | T | 123 | | |
| E | E | 124 | | |
| Q | Q/D | 125 | | |
| D | D/Q | 126 | | |
| E | E | 127 | | |
| D | D/Q | 128 | | |
| E | E | 129 | | |
| E | E | 130 | | |
| M | M/Z | 131 | | |
| D | D/Q | 132 | | |
| V | V/A | 133 | | |
| G | G | 134 | | |
| T | T | 135 | | |
| D | D/Q | 136 | | |
| E | E | 137 | | |
| E | E | 138 | | |
| E | E | 139 | | |
| E | E | 140 | | |
| T | T | 141 | | |
| A | A/V | 142 | | |
| K | K/R | 143 | | |
| E | E | 144 | | |
| S | S/T | 145 | | |
| T | T | 146 | | |
| A | A/V | 147 | | |
| E | E | 148 | | |

Exemplary polypeptides of the invention include a polypeptide according to SEQ. ID. NO. 4, 5, 6, 7, 37, 38, 39, 40, 42, 43, 44, or 45 and having 1, 2 or 3 conservative amino acid substitutions selected from those provided in Table 2.

Substantially homologous polypeptides of the invention include a variant of SEQ. ID. NO. 4, 5, 6 or 7 having one or two conservative amino acid substitutions selected from: substitution of $Ile_{10}$ for Leu, $Ile_{22}$ for Leu, substitution of $Ala_{13}$ for Val, substitution of $Gln_{14}$ for Asp, $Gln_{17}$ for Asp, substitution of $Met_7$ for Nle, substitution of $Met_{11}$ for Nle substitution of $Ser_4$ for Thr, substitution of $Lys_{20}$ to Arg, substitution of $Ser_{23}$ to Thr, substitution of $Thr_{24}$ to Ser, substitution of $Asn_{25}$ to Gln.

In one embodiment, the polypeptides of the invention are acetylated at the N-terminal and amindated at the C-terminal as illustrated for a polypeptide according to SEQ. ID. 4 below:

CH3-CO—NH-$Tyr_1$-$Gly_2$-$Trp_3$-$Ser_4$-$Gly_5$-$Asn_6$-$Met_7$-$Glu_8$-$Arg_9$-$Ile_{10}$-$Met_{11}$-$Lys_{12}$-$Ala_{13}$-$Gln_{14}$-$Ala_{15}$-$Tyr_{16}$-$Gln_{17}$-$Thr_{18}$-$Gly_{19}$-$Lys_{20}$-$Asp_{21}$-$Ile_{22}$-$Ser_{23}$-$Thr_{24}$-$Asn_{25}$-$Tyr_{26}$-$Tyr_{27}$-CO—NH2

In other embodiments polypeptides of the invention can be acetylated at the polypeptide N-terminus. In one embodiment a polypeptide, according to SEQ. ID. NO. 4, is acetylated at the N-terminus and amidated at the C-terminal having a molecular weight of 3176.5, a chemical formula $C_{143}H_{209}N_{37}O_{44}S_2$, and an isoelectric point of 8.34.

Polypeptides of the invention may additionally include N-terminal blocking groups including but not limited to: a N-acetyl amino acid, a glycosylated amino acid, a pyrrolidone carboxylate group, an acetylated amino acid, a formylated amino acid, myristic acid, a pyroglutamate conjugated amino acid. Polypeptides of the invention may additionally include a C-terminal blocking groups such as an amidated amino acid. Other N-terminal or C-terminal blocking groups are known to a person skilled in the art and can be used to modify the polypeptides of the invention as described in Davies (2006, Royal Society of Chemistry, London, UK), "Biochemistry" by Garrett and Grisham (2010, Cengage Learning, Andover, UK) and WO 97/3903.

The polypeptides of the invention can be modified to increase their molecular weight and improve their serum half-life while retaining their therapeutic functional property i.e. reducing PCSK9 binding to LDLR or PCSK9-LDLR internalization at the PM thereby increasing PM levels of LDLR. Bulkier polypeptides have an increased resistance to cleavage by neutral endopeptidase (NEP) and to clearance via naturetic polypeptide receptor C (NPR-C). NEP preferably recognizes substrates smaller than 3 kDa (Oefner, J Mol Biol. 2000; 296:341-349). By adding 0.6 to about 5.0 kDa of amino acids, hydrophilic or water-soluble polymers, hydrophobic acids (including fatty acids) or carbohydrates the serum half-life of a small polypeptide, like those of the invention, can be improved. A longer serum half-life improves the therapeutic benefits of administration of a polypeptide of the invention SEQ. ID. NOs 4-32. In one embodiment, a polypeptide of the invention is conjugated to additional amino acids or other types of natural or synthetic polymeric groups to the polypeptide sequence at the C terminus, N terminus or side chain(s) to increase its size from about 1.4 kDa or 1.6 kDa to about 4.0 kDa, 4.4 KDa, 4.6 KDa, 4.8 KDa, 5 KDa, 5.2 KDa, 5.4 KDa, 5.6 KDa, 5.8 KDa, 6 KDa, 6.2 KDa, 6.4 KDa, or to about 7 KDa, 7.2 KDa or about 8.2 kDa. Polypeptides of the invention include a polypeptide according to Formula 2, 3 or 4 below:

```
FORMULA 2
X- YGWSGNMERIMKAQAYQTGKDISTNYY-CO-U

FORMULA 3
X- MRALWVLGLCCVLLTFGSVRAYGWSGNME

RIMKAQAYQTGKDISTNYY-CO-U

FORMULA 4
X-YGWSGNMERIMKAQAYQTGKDISTNYYASQKKTFE

INPRHPLIRDMLRRIKEDEDDKTVLDLAVVLF-ETAT

LRSGYLLPDTKAYGDRIERMLRLSLNIDPDAKVEEEP

EEEPEETAEDTTEDTEQDEDEEMDVGTDEEEETAKES

TAE-CO-U
```

Wherein (X) and (U) may be independently absent or present and are selected from a synthetic or natural polymeric group, or combination thereof. A non-limiting example of a synthetic polymeric group is polyethylene glycol (PEG). A non-limiting example of a natural polymeric group is an amino acid sequence containing from 1-35 amino acids derived from a naturetic polypeptide e.g. naturetic polypeptide precursor C (NPPC) SEQ. ID. NO. 61 or A naturetic peptide (ANP) SEQ. ID. NO. 63, or variants thereof with substitutions and/or deletions or derived from brain naturetic protein, serum albumin, IgG, histadine-rich glycoprotein, fibronectin, fibrogen, zinc finger-containing polypeptides, osteocrin or fibroblast growth factor 2.

Polypeptides of the invention further include a polypeptide according to Formula 2 having one or more conservative amino acid substitutions.

Substantially homologous variants of the polypeptides of the invention, containing 1, 2, 3 or 4 conservative amino acid substitutions, can also be modified to increase serum half-life, by conjugated a polymer group, as described above, either the C-terminus or N-terminus or both the C-terminus and N-terminus.

It is to be understood that a reference to a particular amino acid position, according to the formula shown herein, refers to the same position, with reference to a particular sequence even when the length of the polypeptide has changed due to the addition of a sequence either to the C- or N-terminus of the polypeptide.

In a preferred embodiment PEG polymer of about 0.6 kDa to 1.2 kDa is conjugated to the N-terminus of a polypeptide of the invention or a substantially identical derivative as described herein. Hydrophilic polymers (e.g. PEG) may vary in type (e.g. homopolymer or copolymer, random, alternating or block polymer, linear or branched, monodispersed or poly-dispersed); linkage (e.g. hydrolysable, or stable linkage such as aminde, imine, aminal, alkylene, or ester bond); conjugation site (N-terminus, C-terminus or internal site) and length (e.g. from about 0.2, 0.4, 0.6 to 1 kDa). Such polymers can be conjugated to a polypeptide by means of a N-hydroxy succinimide (NHS)- or aldhyde based chemistry or other chemistry as is known in the art. In a further embodiment the polypeptides of the invention can be conjugated to PEG, or a similar hydrophilic polymer, at an internal sit such as at $Gln_4$ or $Gln_8$.

The susceptibility of a polypeptide, including those of the invention, to peptidase cleavage can also be beneficially reduced by substituting one or more polypeptide bonds of the polypeptide with a polypeptide bond isostere including but not limited to: —$CH_2$—NH— or —C(═O)—NR— wherein the amide group is alkylated with a R group selected from: methyl, ethyl, n-propyl, isopropyl, cyclopropyl, n-butyl, isobutyl, sec-butyl or tert-butyl, —C(═O)—NH—$CH_2$—, $CH_2$—S—, $CH_2$—S(O)n- (where n is 1 or 2), —$CH_2$—$CH_2$—, —CH═CH—, —CH(CN)—NH—, —CH(OH)—$CH_2$—, —O—C(—O)—NH—, and —NHC(═O)NH—. The polypeptides of the invention include derivatives comprising one or more polypeptide bond isosteres.

The polypeptides of the invention can be conjugated with a detectable label or other signal-generating moieties. Suitable labels and techniques for attaching, using and detecting labeled polypeptides are well known in the art. Labels for use with the polypeptide of the invention include fluorescent labels (e.g. fluorescein, isothiocyanate, rhodamine, phycoerythrin, allophycocyanin, o-phthaldehyde, flourescamine, fluorescent metals, phosphorescent labels, chemi-luminescent labels or bioluminescent labels (e.g. luminal, isoluminol, theromatic acridinium ester), radio-isotope labels (e.g. $^{3}H$, $^{125}I$, $^{32}P$, $^{35}S$, $^{14}C$, $^{51}Cr$, $^{36}Cl$, $^{57}Co$, $^{58}Co$, $^{59}Fe$ and $^{75}Se$), metals, metal chelates or metallic cations (e.g. $^{99}mTc$, $^{123}I$, $^{111}In$, $^{131}I$, $^{97}Ru$, $^{67}Cu$, $^{67}Ga$, $^{68}Ga$, $^{157}Gd$, $^{55}Mn$, $^{162}Dy$, $^{52}Cr$ and $^{56}Fe$). Other suitable labels will be clear to the skilled person such as moieties that can be detected using NMR or ESR spectroscopy. Labelled derivatives can be used for in vitro assays or for in vivo imaging or diagnostic purposes. Such labels are preferably conjugated to the C- or N-terminus of the polypeptides of the invention or polypeptide variant thereof.

Another useful modification of the polypeptides of the invention includes conjugation with a member of a binding pair such as biotin and streptavidin. Such binding pairs may be useful for binding a polypeptide of the invention to a pharmaceutical carrier such as in some liposomal formulations known in the art (Swaminathan J, Ehrhardt C. Expert Opin Drug Deliv. 2012; 9:1489-1503).

Encoding Polynucleotides and Vectors

The invention further includes polynucleotides encoding a polypeptide of the invention e.g. SEQ. ID. NO. 33, 34, 35, or 36, 49, 50, 51, 52, 53, 54, 55, 56, 57, 58, 59 or 60, a fragment or variant thereof. Exemplary polynucleotides of the invention include SEQ. ID. NO. 33, 34, 35, or 36, a fragment or variant thereof. The invention also includes vectors comprising SEQ. ID. NO. 33, 34, 35, or 36, 49, 50, 51, 52, 53, 54, 55, 56, 57, 58, 59 or 60 which are useful for producing a polypeptide of the invention (e.g. using pcDNA3.1 or pIRES for mammalian expression into media or pET24b+ for recombinant bacterial expression).

Compositions comprising one or more of the polypeptides of the invention can be used to treat acute or chronic conditions, in particular conditions causally associated with biological responses to circulating lipids that bind to LDL or to prevent a pathology associated circulating lipids that bind to LDL e.g. atherosclerosis and cardiovascular diseases.

Pharmaceutical Formulations

Polypeptides of the present invention may be combined with pharmaceutically acceptable excipients, and optionally sustained-release matrices, such as biodegradable polymers, to form therapeutic compositions. The pharmaceutical compositions of the present invention contain an active agent, a polypeptide, alone or in combination with another active agent. The therapeutic compositions of the invention can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intra-peritoneal, intra-muscular, intravenous, subdermal, transdermal, intrathecal and intranasal administration forms and rectal administration forms.

Preferably, the pharmaceutical compositions and formulations for injection contain vehicle, which is pharmaceutically acceptable. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising polypeptides as a free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Polypeptides of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium-monostearate and gelatin.

Oral Formulations

Polypeptides of the invention can be used in formulations for oral administration of polypeptides such as those described in Renukuntla et al., International Journal of Pharmaceutics 447 (2013) 75-93, herein incorporated by reference. Formulations known in the art for oral delivery of polypeptides and for use in pharmaceutical formulations of the polypeptides of the invention include: absorption enhancers, enzyme inhibitors, hydrogels, muco adhesive systems, liposomes, nanoparticles microparticles, cylodextrins, and prodrug derivatization.

Polypeptides of the invention may also be co-administered or administered in series with enzyme inhibitors that reduce proteolytic cleavage of the polypeptide in vivo. Inhibitors such as aprotinin (trypsin/chymotrypsin inhibitor), amastatin, bestatin, boroleucine, and puromycin (aminopeptidase inhibitors) have been widely employed to improve formulations therapeutic polypeptide formulations. Other protease inhibitors include: sodium glycocholate, camostat, mesilate, bacitracin, and soybean trypsin inhibitor.

Hydrogel formulations, comprising polypeptides encapsulated in a polymer network are useful in the formulations of the present invention. Hydrogel formulations are well known in the art as described in (Ichikawa and Peppas, 2003; Peppas et al., 2000; Ridgley and Wilkins, 1991). Hydrogels can be classified info neutral hydrogels and ionic hydrogels. Hydrogels can respond physically to the environment such as temperature, ionic strength and pH. Hydrogels can be made of either synthetic or natural polymers and are biodegradable. The polymer network can be comprised of either homopolymers or copolymers. Monomers widely used for preparation of hydrogels for protein or polypeptide delivery include 2-hydroxyethyl methacrylate, ethylene glycol dimethacrylate, N-isopropyl acrylamide, acrylic acid and methacrylic acid, Poly(ethylene glycol) (PEG), poly[methacrylic acid-grafted-poly (ethylene glycol)] and poly(vinyl alcohol).

Muco-adhesive polymers are also useful in the preparation of hydrogen polypeptide formulations for oral delivery. Muco-adhesive polymers included in polypeptide formulations bind to the mucosal membranes and improve the oral bioavailability of polypeptides. Muco-adhesive polymers can also reduce the rate of clearance of the polypeptide from the mucosal membrane and prolong absorption time. In this way they are useful for controlled release polypeptide formulations. Muco-adhesive polymers are generally classified into synthetic or semi-natural. Synthetic bioadhesive polymers are either polyacrylic acid or cellulose derivatives. Polyacrylic acid-based polymers include carbopol, polycarbophil, polyacrylic acid, polyacrylate, poly(methylvinylether-co-methacrylic acid), poly(2-hydroxyethyl methacrylate), poly(methacrylate), poly(alkylcyanoacrylate), poly (isohexylcyanoacrylate) and poly(isobutylcyanoacrylate). Examples of cellulose derivatives are carboxymethyl cellulose, hydroxyethyl cellulose, hydroxypropyl cellulose, sodium carboxymethyl cellulose, methyl cellulose, and methylhydroxyethyl cellulose. Chitosan and various gums such as guar, xanthan, crylamide-acrylate polymer (PHPA), poly (vinylpyrrolidone), and poly (vinyl alcohol) constitute semi-natural bioadhesive polymers.

The polypeptides of the present invention can be formulated as part of polymeric micro/nanoparticles or liposomes compositions using methods known in the art or oral administration or injection. Liposome formulations comprising polypeptides are also useful in the present invention. Methods for preparing small uni-lamellar vesicles (SUV) of 10-100 nm, large uni-lamellar vesicles (LUV) of 100-300 nm and multi-lamellar vesicles are well known in the art such as described in U.S. Pat. Application 20130251783A1 and U.S. Pat. Application 20120039990 A1. Liposome formulations have proven beneficial for therapeutic delivery of polypeptides. Such vesicles are made of naturally derived phospholipids such as egg phosphatidylethanolamine or dioleoylphosphatidylethanolamine (DOPE), phosphotidyl choline or phosphotidyl inositol (Dharma et al., 1986). In particular dehydrated-rehydrated vesicles are useful for delivery of the polypeptides of the invention.

Nanoparticles or colloidal carriers with a size ranging between 1 and 100 nm are also useful for delivery of the polypeptides of the present invention. Formulations comprising the polypeptides of the invention as part of either nanocapsules or nanospheres are contemplated herein. Nanoparticles are a preferred delivery method as they are stable in the GI environment, can be tailed for controlled or targeted release as described in Panyam and Labhastwar, 2003.

Absorption enhancers act to enable mucosal (i.e. Intestinal mucosa or nasal mucosa) absorption of a polypeptide by disrupting the structural integrity of the mucosal membrane, decreasing mucus viscosity, opening tight junctions or increasing membrane fluidity (Aungst, 2012; Checkoway et al., 2012; Jitendra et al., 2011; Williams and Barry, 2004). Absorption enhancers include: (i) surfactants; such as sodium lauryl sulfate, laureth-9, sodium dodecylsulfate, sodium taurodihydrofusidate, poly oxyethylene ethers; (ii) chelating agents such as edta, citric acid, salicylates; (iii) bile salts such as sodium deoxycholate, sodium taurocholate, sodium glycodeoxycholate, sodium taurodihydrofusidate, sodium glycodihydrofudisate; (iv) cationic polymers such as chitosan and its derivatives; (v) anionic polymers such as carbopol and polyacrylic acid; acylcarnitines such as lauroyl-l-carnitine chloride, palmitoylcarnitine chloride; fatty acids such as oleic acid, linoleic acid, caprylic acid, capric acid, acylcarnitines, mono and di-glycerides; and their derivatives.

Nasal or intranasal delivery is effective for small polypeptides such as those of the present invention, weighing between 1.5-4 kDa. Nasal delivery is a good route of administration for the Polypeptides of the invention as it provides a direct route, which circumvents liver metabolism and the harsh conditions of the gastrointestinal system. The pharmaceutical compositions of the invention may be in the form of a nasal spray, nose drops, nose ointment, nose powder or nose oil. Liquid compositions for nasal administration typically include water as a carrier with the polypeptide dispersed in water or ringer solution.

Compositions comprising a polypeptide of the invention in the form of an oil-in-water, water-in-oil emulsions are also contemplated. Such compositions may additionally include absorption enhancers or promoters such as those disclosed in U.S. Pat. No. 5,023,252. Absorption promoters for formulation with the polypeptides of the invention for nasal administration include surfactants or chelators. Other strategies for nasal delivery of polypeptide include powder formulations as described in European Pat. Nos. 2,359 and 122,023 and admixtures of mucosa-absorptive substances and powered polypeptide as disclosed in U.S. Pat. No. 4,250,163. Various other strategies including PEG-polypeptide conjugates and micro-particles as described in detail in U.S. Pat. No. 6,506,730. The pH of a pharmaceutical composition comprising a polypeptide, for nasal delivery is preferably in the range from 6.0 to 8.0, or 6.5 to 8.0, or preferably 7.0 to 7.5.

Emulsifying agents for use in emulsions of the polypeptides of the invention include acacia, tragacanth, agar, pectin, carrageenan, gelatine, lanolin, cholesterol, lecithin, methylcellulose, carboxymethylcellulose, acrylic emulsifying agents, such as carbomers and combinations thereof. In general the emulsifying agent is present in the emulsion at a ratio of 0.001:5% weight emulsifying agent:composition, or at a ratio of 0.001:5% weight emulsifying agent:composition, or at a ratio of 0.1:2% weight emulsifying agent: composition.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Polypeptides of the invention may be formulated for parenteral administration, such as intravenous or intramuscular injection, other pharmaceutically acceptable forms include, e.g. tablets or other solids for oral administration; liposomal formulations; time release capsules; and any other form currently used. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. The polypeptides of the invention may be formulated within a therapeutic mixture to comprise about 0.0001 to 1.0 milligrams, or about 0.001 to 0.1 milligrams, or about 0.1 to 1.0 or even about 10 milligrams per kilogram per dose or so. Multiple doses can also be administered.

Co Administration with Other Drugs and Combination Therapies

The polypeptides of the invention may also be used in combination with other therapeutic agents, for instance. HMG-CoA reductase inhibitors such as statins; PCSK9 monoclonal antibodies, PCSK9 immunizing polypeptides, PCSK9 siRNA, niacin; cholesterol absorption-inhibiting supplements such as ezetimibe and fibrates; CETP inhibitors such as evacetrapib, anacetrapib, dalcetrapib; HDL-mimetics, angiotensin-converting enzyme inhibitors such as perindopril, captopril, enalapril, lisinopril, and ramipril; angiotensin receptor antagonists such aslosartan, candesartan, telmisartan, valsartan; beta-blocker drugs such as bisoprolol, carvedilol and sustained-release metoprolol; cardio tonic agents such as ivabradine; calcium channel blockers such as amlodipine, aranidipine, azelnidipine, barnidipine, benidipine, cilnidipine, clevidipine, isradipine, efonidipine; folic acid, aspirin, anti-inflammatory drugs or other drugs commonly used in standard cardiovascular care are likely to be co-administered with the polypeptides of the invention in the treatment of patients with cardiovascular or coronary artery disease. Steroids, non-nonsteroidal anti-inflammatory drugs (NSAIDS), Immune Selective Anti-Inflammatory Derivatives (ImSAIDs) and other types of anti-inflammatory drugs known in the art are commonly used in the treatment of inflammatory diseases and are likely to be co-administered with the polypeptides of the invention, in patients with inflammatory disease, for example arthritis. Moreover when the polypeptides of the invention are co-administered with another drug, if they are contained in different pharmaceutical compositions, said compositions may be administered to the patient at the same time or successively. The foregoing therapeutically active agents are listed by way of example and are not meant to be limiting. Other therapeutically active agents which are currently available or that may be developed in the future are equally applicable to the methods of the present invention.

The therapeutic efficacy of the polypeptides of the invention, and of compositions comprising the same, can be tested using any suitable in vitro assay, cell based assay or in vivo assay and/or animal model known or in any combination thereof. Exemplary assays include solid phase binding assays, lipid-lowering effect (LDL-Cholesterol measurements), LDL internalisation, competitive in vitro PCSK9 binding to LDLR, intravascular ultrasound (IVUS); in vivo atherogenesis assay, as well as the in vivo and in vitro assay method described in the methods section included herein.

Anti-inflammatory activities may be detected or monitored in vivo through measures of known inflammation biomarkers including: cytokines such as TNF-α, IL6, IL1 and measures of adhesion molecules such as P-selectin, ICAM1. Measures for use in the invention include expression of such inflammatory biomarkers by cells comprising or within arteries or measures circulating levels of cytokines or adhesion molecules in blood, serum or plasma. Pro-atherogenesis activities measured as part of the screening methods of the present invention include: measures of the evolution of the atherosclerotic plaque size through time, measure of the burden of oxidative stress using the measure of 4-HNE, isoprostane, nitrosylated proteins and the like as well as measure of the macrophage load in the atherosclerotic plaque.

The anti-inflammatory activities of the polypeptides of the invention can be evaluated by measuring: the level of cytokines such as TNF-α, IL6, IL1 and measures of adhesion molecules such as P-selectin, ICAM1.

Pro-atherogenesis activities of the polypeptides of the invention can be evaluated by measuring of the evolution of the atherosclerotic plaque size through time, measure of the burden of oxidative stress using the measure of 4-HNE, isoprostane, nitrosylated proteins and the like as well as measure of the macrophage load in the atherosclerotic plaque, as further described herein. Methods for measuring isoprostane are known in the art and described in Leblond F, et al. Pflugers Arch. 2013; 465:197-208, herein incorporated by reference. Methods for measuring 4-HNE are known in the art and described in Voghel G, et al. Mech Ageing Dev. 2008; 129:261-270, herein incorporated by reference. Methods for measuring nitrosylated proteins are known in the art and described in Qin Y, et al. Methods Enzymol. 2013; 522:409-25, herein incorporated by reference.

A level of PCSK9 protein and LDL-Cholesterol in a biological sample may be determined by known methods. Protein levels can be assayed in a biological sample using an Enzyme-linked immunosorbent assay (ELISA) or using a mass spectrometry based assay. The methods and technologies for Indirect ELISA (Biochemistry. 7th edition. Berg J M, Tymoczko J L, Stryer L. New York: W H Freeman; 2012), Sandwich ELISA, Competitive ELISA as well as Multiple and Portable ELISA assays (U.S. Pat. No. 7,510,687; European Patent EP1499894) are well known in the art and widely used Determining a protein level in a sample typically involves a) contacting the polypeptides contained in the biological sample with an agent that specifically binds a PCSK9 polypeptide; and (b) detecting any agent:polypeptide complex formed. In one aspect of the invention, the agent that specifically binds PCSK9 is a polypeptide of the present invention or an antibody targeting PCSK9-polypeptide interaction, preferably a monoclonal antibody. The formation of an agent:polypeptide complex can be detected directly or indirectly according to standard procedures known in the art. In the direct detection method, the agents are supplied with a detectable label and unreacted agents may be removed from the complex; the amount of remaining label thereby indicating the amount of complex formed. In the alternative, an indirect detection procedure requires the agent to contain a label introduced either chemically or enzymatically, that can be detected by affinity cytochemistry. A desirable label generally does not interfere with binding or the stability of the resulting agent:polypeptide complex. However, the label is typically designed to be accessible to an antibody for an effective binding and hence generating a detectable signal. A wide variety of labels are known in the art. Non-limiting examples of the types of labels that can be used in the present invention include radioisotopes, enzymes, colloidal metals, fluorescent compounds, bioluminescent compounds, and chemiluminescent compounds.

A variety of techniques for protein analysis are available in the art. They include but are not limited to radioimmunoassays, ELISA (enzyme linked immunoradiometric assays), "sandwich" immunoassays, immuno-radiometric assays, in situ immunoassays (using e.g., colloidal gold, enzyme or radioisotope labels), western blot analysis, immuno-precipitation assays, immuno-fluorescent assays, and SDS-PAGE. In addition, cell sorting analysis can be employed to detect cell surface antigens. Such analysis involves labelling target cells with antibodies coupled to a detectable agent, and then separating the labelled cells from the unlabeled ones in a cell sorter. A sophisticated cell separation method is fluorescence-activated cell sorting (FACS). Cells traveling in single file in a fine stream are passed through a laser beam, and the fluorescence of each cell bound by the fluorescently labelled antibodies is then measured. Antibodies that specifically recognize and bind to the protein products of interest are required for conducting the aforementioned protein analyses. These antibodies may be purchased from commercial vendors or generated and screened using methods described herein.

In some embodiments of the invention subjects at risk of atherosclerosis are treated with a polypeptide of the present invention. Risk factors for atherosclerosis include: unhealthy blood cholesterol levels, high LDL-C or low HDL; high blood triglyceride levels; high blood pressure; Smoking; insulin resistance; diabetes; overweight or obesity; family history of early coronary artery disease; lack of physical activity; high levels of C-reactive protein (CRP) in blood; heart attack; chronic inflammation and diseases associated with chronic inflammation; sleep apnea; stress and alcoholism or heavy drinking. Other risk factors include high circulating levels of PCSK9, ICAM-1, P-Selectin and ANGPTL2. Elevated plasma level of one or more of ICAM-1, P-Selectin, ANGPTL2 and PCSK9 possibly indicate the presence of active atherogenesis in a subject and constitute an atherosclerosis risk factor or diagnostic measure. These risk factors can be used in combination with the diagnostic and treatment selection methods described herein to identify subjects at risk of atherosclerosis.

Screening Assays and Assay Systems

Assay systems of the invention are comprised of: (i) cultured cells transformed to stably express a fluorescent LDLR conjugate protein at the cell surface and (ii) extracellular fluorescently labelled PCSK9 conjugate under physiological conditions.

The cell-based assay of the invention can be used to evaluate the effect of variants or mutations in PCSK9 on binding of PCSK9 to cell surface LDLR and internalization of PCSK9-LDLR complex. Such variant PCSK9 sequences can be conjugated to a fluorescent protein and used in the assay methods or systems described herein. The approach can be used for identification or comparison of the effect of gain-of-function or loss-of-function PCSK9 mutations compared to wild type PCSK9.

The assay system and methods of the invention can be used to identify PCSK9 inhibitors (either small molecule or biological), small molecule compounds or biologics that bind to LDLR and block the interaction between LDLR and PCSK9 or compounds (small molecules or biologics) that modulate the PCSK-9-LDLR interaction through a different mechanism of action.

In one aspect the assay can be used to determine map the functional impacts of mutations or polymorphisms in PCSK9, LDLR or any other protein that modifies the PCSK9-LDLR interaction by binding to PCSK9 or LDLR. Such studies can be based on screening of CRISPR-Cas9 sgRNA-mediated knockout libraries in large functional screens.

Additional assay components for cell based assays are well known in the art. These include without limitation diluents, salts, buffers, chelating agents, preservatives, drying agents, antimicrobials, growth factors, needles, syringes, packaging materials, tubes, bottles, flasks, beakers, and the like.

The assay system of the invention may be in the form of an assay kit comprising one or more components selected from: vectors or plasmids encoding a fluorescent PCSK9 fusion protein e.g. SEQ ID NO. 70 or 68, vectors or plasmids encoding LDLR fluorescent fusion protein e.g. SEQ ID NO. 69, or PCSK9 fluorescent fusion protein e.g. SEQ. NO. 74 or 75. Kit components are in a container, stored and shipped at room temperature, chilled, in liquid nitrogen or on dry ice. Instructions may include instructions for culturing, using, modifying, mixing, diluting, preserving, assembling or storing the cell samples and/or other components according to the assay methods and systems described herein. The instructions may also include instructions for a specific assay to be performed with the cell samples, e.g. their use in screening assay. Instructions may be also be in the form of directions to a website, they may also contain links to computer systems and/or computer memory storage devices.

The invention will be further illustrated by the following figures and examples. However, these examples and figures should not be interpreted in any way as limiting the scope of the present invention.

In yet other embodiments, assay systems of the invention are comprised of: cultured cells transformed to stably express a fluorescent LDLR conjugate protein at the cell surface and also stably express and excrete extracellular fluorescently labelled PCSK9 conjugate protein.

EXAMPLES

From a screening experiment design to identify new PCSK9 (SEQ. ID. NO. 1) interacting proteins, this invention is based on the identification of GRP94 (SEQ. ID. NO. 3) as a new specific binding partner of PCSK9. A secretable form of human GRP94 (lacking its C-terminal KDEL sequence; GRP94-ΔKDEL; SEQ. ID NO. 66) was shown to specifically binds to PCSK9 within the cells and can be used as a binding protein for pharmacological treatments or screening assays as described herein. Overexpression of SEQ. ID. NO. 66 or incubation of cells with recombinant GRP94 block PCSK9 internalization and have inhibitory effects on PCSK9-induced LDLR degradation.

Alanine Scanning

Alanine-scanning mutations within the client-binding domain (CBD) of GRP94 (aa652-678), identified as AA1 ($^{652}$YAASAAAAAIMKAQAYQTGKDISTNYY; SEQ. ID NO. 78) and AA2 ($^{652}$YGWSGNMERIMKAQAYATGKAISTNAA; SEQ. ID NO. 79), (Wu et al., 2012)), abolished PCSK9 binding to GRP94.

Domain mapping revealed that neither GRP94 N-Terminal domain (aa22-651), nor PCSK9 C-Terminal domain (aa456-692) participate in complex formation.

Experimental Methods

Chemicals and Plasmids

Geldanamycin (Cat. #BML-EI280) was purchased from Enzo Life Sciences. Full-length human V5-tagged PCSK9 and LDLR were subcloned into pIRES2-EGFP (Cat. #6029-1, Clonetech) vector as described (Poirier et al., 2014). Plasmids encoding truncated PCSK9 cDNAs PCSK9-L455X (amino acids; aa 1-455) and PCSK9-CHRD (aa 1-33(Q31N)-405-692) were kindly provided by Dr. N. Seidah (Clinical Research Institute of Montreal). Plasmid encoding His-tagged human PCSK9 (pIRES-hPCSK9-V5-His$_6$) was generated by overlapping PCR. SEQ ID. NO. 2 (Cat. #HsCD00339553; pCMV-SPORT6-hHSP90B1, Accession BC066656) was obtained from DF/HCC DNA Resource Core (Harvard Medical School). SEQ ID. NO. 3 (aa 800-803) sequence was PCR amplified and fused at its C-terminus with the human influenza hemagglutinin (HA) epitope tag (YPYDVPDYA) using the Phusion High-Fidelity DNA polymerase (Cat. #M0530S, New England Biolabs) and subcloned into pCMV-SPORT6 vector at EcoRV/XhoI (New England Biolabs) endonuclease sites. Alanine-scanning mutants (AA1: $^{652}$YAASAAAAAIMKAQAYQTGKDISTNYY, SEQ ID. NO. 78 and AA2: 652YGWSGNMERIMKAQAYATGKAISTNAA SEQ ID. NO. 79; (Wu et al., 2012)) were generated by PCR amplification using SEQ ID. NO. 66 as template and inserted into PmlI/XhoI sites. SEQ ID. NO. 46 comprising its signal polypeptide (SP; aa 1-21), client-binding domain (CBD; aa 652-678) and C-terminal domain (aa 679-799) lacking its KDEL terminal sequence was PCR amplified and subcloned into pcDNA3.1neo+ vector (Invitrogen) at BamHI/XhoI restriction sites as described (Aimiuwu et al., 2012).

The monomeric fluorescent Cherry coding cDNA was fused to PCSK9 C-terminus using pCMV-Cav1-mCherry as a template (Cat. #27705, Addgene). Prior to subcloned human PCSK9 in frame at the AgeI cloning site, one nucleotide deletion was performed by QuickChange II site-directed mutagenesis (Cat. #200523, Agilent) using the following oligonucleotides: 5'-CAGACCGGTCGC-CA-CATGGTGAGCAAGG; 5'-CCTTGCTCAC-CATGTGGCGACCGGTCTG. The caveolin-1 cassette was then replaced by human PCSK9 cDNA at the BglII/AgeI cloning sites. Enhanced green fluorescence protein (EGFP) was fused to LDLR cDNA at its C-terminal (pCMV-hLDLR-GFP) by PCR amplification and subcloned at AgeI/NotI into pIRES-hLDLR-V5 resulting in deletion of the V5-tag sequence and the internal ribosomal entry site (IRES).

Cell Culture and Transfections

Human hepatoma cell lines HepG2 and Huh-7 were routinely cultivated in Dulbecco's modified Eagle's medium (DMEM; Cat. #319-005-CL, Wisent) supplemented with 10% Fetal Bovine Serum (FBS; Cat. #080-350, Wisent). Human embryonic kidney 293 (HEK293 and HEK293T) cells were cultivated in complete DMEM without sodium pyruvate (Cat. #319-015-CL, Wisent). HepG2 were transfected with Lipofectamine 3000 (Cat. #L3000008, Life Technologies) according to the manufacturer's recommendations. Small interfering RNAs (siGenome Non-Targeting pool; Cat. #D-001206-14-05 and siGenome SMART pool; HSP90B1, Cat. #M-006417-02) were obtained from GE HealthCare Dharmacon and were transfected using Lipofectamine RNAiMax reagent (Cat. #13778075, Life Technologies). HEK293 and HEK293T cells were transfected with linear polyethylenimine MW 25,000 (PEI; Cat. #23966, Polysciences) at ratio of 0.8:0.2 PEI (μg):DNA (μg) per $cm^2$ of cell surface area.

Immunoprecipitation and Western Blot Analysis

For identification of novel PCSK9 interactors, HepG2 or Huh-7 cells (55 cm2) were washed three times in phosphate-buffered saline (PBS) and incubated with 1 mM dithiobis [succinimidylpropionate] (DSP; Cat. #22585, Thermo Scientific), a thiol-cleavable cross-linking reagent, for 30 min at room temperature and subsequently switch for 15 min into a stop solution (15 mM Tris, pH 7.5). Cells were then lysed in complete radio-immune precipitation assay (RIPA) buffer (50 mM Tris/HCl, pH 8.0, 1% (v/v) Nonidet P40, 0.5% sodium deoxycholate, 150 mM NaCl and 0.1% (v/v) sodium dodecyl sulfate (SDS)) supplemented with a complete protease inhibitor mixture (Cat. #11 697 498 001, Roche Applied Science), passed 25 times through a 22-gauge needle and centrifuged at 11,000 g for 15 min at 4° C. Supernatants were incubated and rotated overnight with pre-immune serum, rabbit anti-hPCSK9 (amino acids 31-454) (1:250; Dr. Nabil Seidah, Clinical Research Institute of Montreal) or mouse anti-V5-tag (1:500; Cat. #R96025, Life Technologies) together with 50 μl protein A/G PLUS-agarose (Cat. #sc-2003, Santa Cruz). Following overnight incubation, beads were washed six times in RIPA buffer and resuspended in 75 μl Laemmli sample buffer. Co-immunoprecipitated (Co-IP) proteins were separated by 8% SDS-polyacrylamide gel electrophoresis and visualized using the Pierce silver stain kit (Cat. #24600, Thermo Scientific) according the manufacturer's instructions. All other Co-IP experiments were performed as described without the cross-linking step and in SDS-deprived RIPA buffer. HA-tagged proteins and GRP94 were immunoprecipitated with mouse anti-HA-tag (1:500; Cat. #H3663, Sigma-Aldrich) or rat anti-Grp94 (9G10, 1:1000; Cat. #ADI-SPA-850, Enzo Life Sciences).

For Western blot analyses, SDS-polyacrylamide gels were blotted on nitrocellulose membranes (Cat. #162-0115, Bio-Rad), and blocked for 1 h in Tris-Buffered Saline-Tween 20 (TBS-T; 50 mM Tris-HCl, pH 7.5, 150 mM NaCl, 0.1% Tween 20) containing 5% non-fat dry milk. Membranes were then incubated overnight in TBS-T supplemented with 1% non-fat milk and indicated antibodies: rabbit anti-PCSK9 (1:2500, custom made, GenScript), goat anti-human or anti-mouse LDLR (1:1000; Cat. #AF2148 or #A2255, R&D Systems), rat anti-Grp94 (1:30,000), rabbit anti-GRP78 (1:2500; Cat. #ab21685, Abcam), rabbit anti-GFP (1:2000; Cat. #A11122, Life Sciences), mouse anti-V5-tag (1:5000; Cat. #A00641, GenScript), mouse anti-HA-tag (1:5000), rabbit anti-β-actin (1:5000; Cat. #A2066, Sigma-Aldrich). Appropriate HRP-conjugated secondary antibodies (1:10,000, GE healthcare) were used for detection using the Western Lightning Ultra chemiluminescence kit (Cat. #NE1112001EA, PerkinElmer) and BioFlex EC Films (Cat. #CLEC810, InterScience).

Mass Spectrometry Analysis

Following electrophoresis, selected gel lanes were excised into 1 $mm^3$ pieces and protein complexes were identified by LC-MS/MS as described previously (Cloutier et al., 2009). Briefly, bands were extensively washed, destained and re-hydrated at 4° C. for 40 min in trypsin solution (6 ng/μl; Cat. #V5111, Promega, 25 mM ammonium bicarbonate). Protein digestions were performed at 58° C. for 1 h and stopped with 1% formic acid/2% acetonitrile (ACN) solution and polypeptides were extracted from supernatants with 1% formic acid/50% ACN and dried until LC-MS/MS analyses. Resuspended polypeptides were run on a C18 reversed phase column mounted on a nanoLC-2D system (Eksigent) coupled to the LTQ Orbitrap (ThermoFisher Scientific). LC-MS/MS acquisitions were accomplished using a four-scan event cycle enabling high resolution/high mass accuracy. Protein database searching was performed with Mascot 2.1 (Matrix Science) against the human NCBInr protein database.

Immunocytochemistry and Confocal Microscopy Analysis

Huh-7 cells were washed three times with PBS, fixed with Bouin's solution (0.9% picric acid, 9% paraformaldehyde, 5% acetic acid/PBS) for 15 min. Following extensive PBS washes, cells were permeabilized with 0.1% Triton X-100/PBS for 10 min and incubated with 150 mM glycine to stabilize the aldehydes. The cells were then incubated for 30 min with 1% BSA (Fraction V; Cat. #BP1605, Sigma) containing 0.1% Triton X-100, followed by overnight incubation at 4° C. with rabbit anti-human PCSK9 (1:250) and rat anti-Grp94 (9G10, 1:1000; Cat. #ADI-SPA-850, Enzo Life Sciences). Afterward, cells were incubated for 60 min with corresponding Alexa Fluor-conjugated secondary antibodies (Molecular Probes) and mounted in 90% glycerol containing 5% 1,4-diazabicyclo[2.2.2]octane (DABCO; Cat. #D27802, Sigma). For PCSK9-mCherry (SEQ. ID. NO. 75 or 76) and LDLR-GFP (SEQ. ID. NO. 77) subcellular visualization, cells were transfected with corresponding plasmids or swapped with conditioned media containing PCSK9-mCherry. Twenty to forty-hours post-treatments, cells were washed three times with PBS and fixed with 4% paraformaldehyde/PBS for 15 min. Immunofluorescence analyses were performed with an Olympus FluoView FV10i confocal microscope.

Reverse Transcription and Quantitative Real-Time PCR

The integrity of total RNA samples, isolated using TRIzol (Cat. #15596026, Invitrogen), was verified by agarose gel electrophoresis or by an Agilent 2100 Bioanalyzer profile. Afterwards, cDNA was prepared using the SuperScript II Reverse transcriptase according the manufacturer's instructions (Cat. #18064-014, Invitrogen). Quantitative Real-Time PCR was performed with the MX3000p real-time thermal cycler (Agilent) using the PerfeCTa SYBR Green SuperMix, UNG, Low ROX (Cat. #95070-100, Quanta Biosciences). For each gene of interest, dissociation curves and agarose gel electrophoresis were performed to ensure unique PCR product. Arbitrary unit was determined from PCR duplicates for each sample using the ribosomal protein S16 as a normalizer. Oligonucleotides sequences used were: mouse Ldlr (5'-GGAGATGCACTTGCCATCCT, 5'-AGGCTG-TCCCCCCAAGAC), mouse S16 (5'-AGGAGCGAT-TTGCTGGTGTGG; 5'-GCTACCAGGGCCTTT-GAGATG).

Recombinant Protein Production and Purification

Full-length recombinant SEQ ID. NO. 67 (Cat. #ADI-SPP-766) was obtained from Enzo Life Sciences. For recombinant SEQ ID. NO. 43, the coding sequence of human GRP94 (aa 652-799) was PCR amplified and cloned into NheI/XhoI sites of pET24b(+) T7-inducible vector (Cat. #69750, EMD Millipore). SHuffle T7 Competent *E. Coli* (Cat. #C3026H, New England Biolabs) bearing the resulting pET24b(+)-SEQ ID. NO. 43 plasmid were grown at 30° C. in DYT media under Kanamycin selection to an $A_{600}$ of 0.6 at which protein production was induced by addition of 1 mM isopropyl-β-D-thiogalactopyranoside (IPTG; Cat. #IPT001.5, BioShop) and kept growing for an additional 5 h. Following centrifugation at 6,000 g for 15 min, bacterial pellet was resuspended and sonicated in 60 ml of Buffer A (20 mM sodium phosphate, 500 mM NaCl, pH 7.4) and centrifuged at 11,000 g to remove debris. Resulting supernatant containing SEQ ID. NO. 43 recombinant protein was kept at 4° C. until purification. For human PCSK9 recombinant production, HEK293T cells (20×75 $cm^2$) were transiently transfected with pIRES-hPCSK9-V5-$His_6$ using PEI for which media was replaced 7 h post-transfection. Thirty hours post-transfection, each plate was replenished with 40 ml DMEM for 24 h. The following day, media was collected and fresh DMEM was added for another 24 h. A total of ~1.5 L of conditioned media were filter sterilized (0.45 μm; Cat. #83.1822, Sarstedt) in which imidazole was added at a final concentration of 5 mM. After equilibration in Buffer A, conditioned media or bacterial lysate containing SEQ ID. NO. 43 were loaded on a HisTRAP excel column (Cat. #17-3712-05, GE healthcare). Prior to elution, the column was washed with 10 bead volumes of Buffer A containing 5 mM or 40 mM imidazole for PCSK9-V5-$His_6$ or SEQ ID. NO. 43, respectively. Afterwards, proteins were eluted by a continuous gradient of imidazole ranging from 5 to 500 mM (10 ml) and 500 mM imidazole was maintained for a total 25 ml elution volume. Eluted fractions monitored by absorbance at 280 nm were verified by western blotting and SDS-electrophoresis followed by coomassie staining (0.25% coomassie brilliant blue 250, 45% methanol, 10% acetic acid). Selected fractions were pooled and concentrated using Amicon centrifugal filters (Cat. #UFC500396, #UFC903024, EMD Millipore) down to 100 μl and loaded on a pre-equilibrated Superose 12 10/300 GL column (Cat. #17-5173-01, GE healthcare) for size exclusion chromatography. All FPLC protein purifications were performed using an ÄKTA explorer system (GE healthcare). Purity and specificity of purified recombinant proteins were verify by gel electrophoresis and coomassie staining as well as Western blotting for which pure protein concentration was determined either by using extinction coefficient calculation at $A_{280}$ for SEQ ID. NO. 43 (NanoDrop 2000, Thermo Fisher Scientific) or by ELISA for PCSK9-V5-$His_6$ (CircuLex Human PCSK9 ELISA Kit; Cat. #CY-8079, MBL International) according to the manufacturer's recommendations.

Animal Studies

Hepatocyte-specific Grp94-deficient mice (cGrp94f/f) were obtained by crossing Alb-Cre with Grp94f/f for which littermates lacking Alb-Cre served as WT controls (Chen et al., 2014). Wild-type C57BL/6 male mice were obtained from Charles River and maintained on a standard rodent diet for 3 days in a 12 h light/12 h dark cycle for acclimatization. Pcsk9-deficient male mice (Pcsk9−/−; Jackson Laboratories) were continuously backcrossed to C57BL/6 mice at least six generations prior to experimentations. Animals were anesthetized by isoflurane inhalation, blood was collected by cardiac puncture and dissected livers were snap-frozen in liquid nitrogen for further analyses. Plasma LDL-Cholesterol was measured using L-Type LDL-C Reagents (Cat. #993-00404, -00504, Wako Diagnostics). Circulating mouse Pcsk9 was immunoprecipitated and analyzed by Western blotting, as described previously (Poirier et al., 2014). All animal studies were approved by the Montreal Heart Institute Animal Care and Ethical committee.

PCSK9 Competitive Assays

Solid phase PCSK9-LDLR epidermal growth factor precursor homology domain A and B (LDLR EGF-AB) in vitro competitive binding assay (Circulex; Cat. #CY-8150) was performed with 100 ng (13.46 nM) of recombinant PCSK9-His6 together with increasing amount of recombinant SEQ ID NO. 6 according to manufacturer's recommendations. Using this in vitro competitive assay, SEQ ID NO. 6 was shown to specifically inhibit binding of WT PCSK9 to the LDLR-EGF-AB domain with an IC50 ~113 nM.

High-Throughput/content (HT/CS) Assay

HEK293 cells or human hepatic cell lines (HepG2 or Huh-7) were stably transformed with a vector comprising the cDNA according to SEQ ID NO. 69 corresponding to the human LDLR-EGFP fluorescent conjugated protein.

HEK293 cells were transformed with a vector comprising the cDNA according to SEQ ID NO. 68 or 74) corresponding to the PCSK9-WT-mCherry (SEQ. ID. NO. 75) or PCSK9-D374Y-mCherry (SEQ. ID NO. 76) fluorescent fusion protein. Prepare PCSK9-D374Y-mCherry conditioned media from stably expressing HEK293_PCSK9-D374Y-mCherry cells by plating 12×T75 flasks. At >80% confluence, remove media and add 10 ml DMEM without phenol red (Cat. #319-050-CL, Wisent) to each flask (total 120 ml).

Following overnight incubation, vacuum filter media (0.45 μM filter; Cat. #83.1822, Sarstedt) and keep at 4 C or −20 C. Addition of 10 ml DMEM to each flasks can be done for another day resulting in a total of ~240 ml of filtered media containing PCSK9-WT- or D374Y-mCherry (enough for 2 runs). Trypsinize HepG2 or HEK293_LDLR-EGFP cells (low passage) from ~5× confluent T75 flasks (~12×10^6 cells/flask) and dilute in DMEM (Cat. #319-005-CL, Wisent) supplemented with 10% FBS (Cat. #080-350, Wisent) to a final concentration of 4×10^5 cells/ml. Plate HepG2 cells at density of 4×10^4/well (100 μl/well from 4×105 cells/ml suspension).

The assay could also be performed on cells co-expressing SEQ ID NO. 69 together with SEQ ID NO. 68 or 74 corresponding to human LDLR-EGFP and PCSK9-wt-mCherry and PCSK9-D374Y-mCherry fluorescent conjugated proteins.

The effect of negative and positive control solutions on PCSK9-LDLR binding or PCSK9 internalization were tested by incubating the transformed HEK239 cells as follows:

Negative Control: 10 μl DMSO 2% (stock 2 μl in 100 μl DMEM)+190 μl DMEM (final conc. DMSO 0.1%). Positive Ctrl: 4 nM (10×IC50) of PCSK9 neutralizing antibody (1.6 μg, 2.5 μl of 0.67 mg/ml; Cat. #71297, lot #121204-D, BPS Bioscience) in 1 ml of conditioned media obtained from HEK293 stably expressing PCSK9-D374Y-mCherry.

The effect of negative and positive control solutions on PCSK9-LDLR binding or PCSK9 internalization were tested by incubating the transformed HEK239 cells as follows:

Typical inhibitory assay experiment using the dual fluorescent cell-based assay.

Forty-eight hours after plating of HEK293-LDLR-EGFP of HepG2-LDLR-EGFP expressing cells, remove the media, wash 3× with 150 μl of DMEM without serum and without phenol red (to wash residual endogenous PCSK9 in the media; only case for hepatic cell lines) and add 190 μl of DMEM_PCSK9-WT-mCherry or PCSK9-D374Y-mCherry+10 μl of 20× compounds, polypeptides, etc. to be tested to each well and mix gently. Also add negative (0.1% DMSO), positive (1.6 μg neutralizing Ab). Following 4-6 hours incubation, analyze LDLR-EGFP+PCSK9-mCherry residual fluorescence.

Validation of Dual Fluorescent PCSK9-LDLR Cell-Based Assay

As reference readout, ineffective inhibitors, removal of irrelevant proteins (not modulators of PCSK9-LDLR interaction), or variation/mutations in participating proteins with no functional impact, will result in low LDLR-EGFP levels and high PCSK9-mC (FIG. 15; top panel) and a red fluorescent signal will be detected. The predominant signal detected will be from the fluorophore conjugated to PCSK9 in this example m-Cherry, however any other suitable fluorophore that would function in the same way as m-Cherry could be used.

Figure 15:
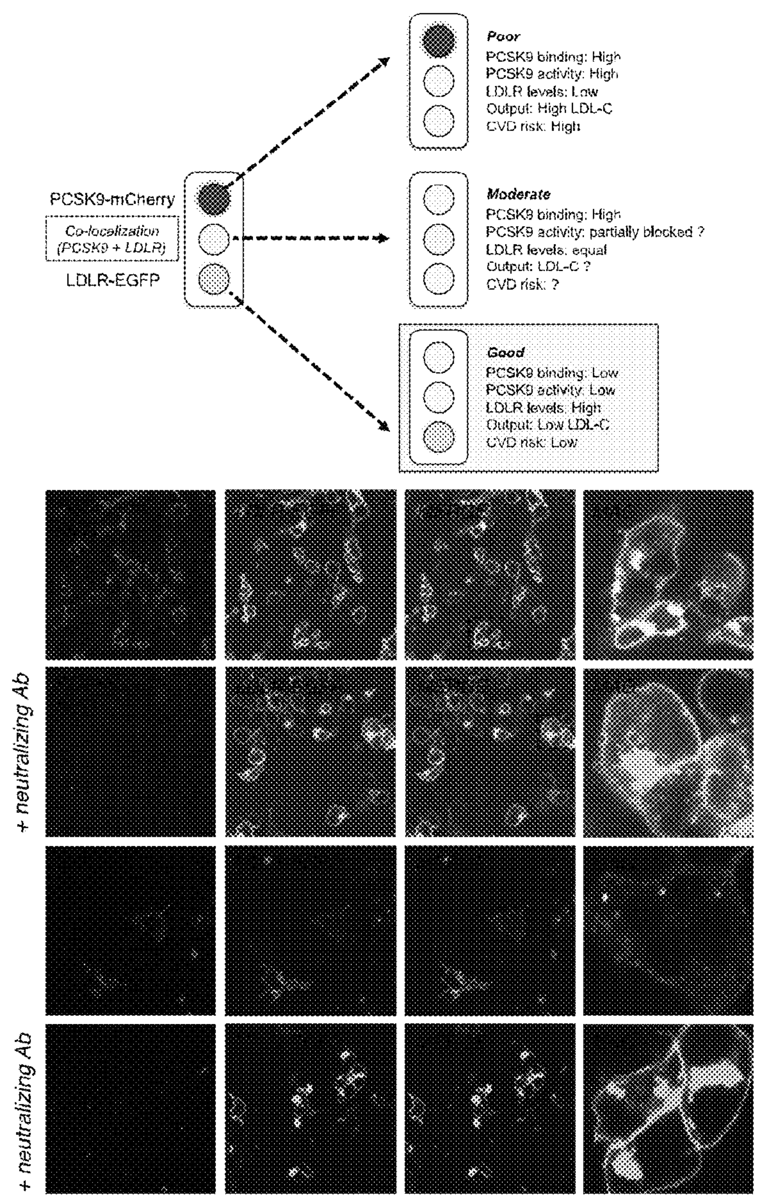
FIG. 15: Dual fluorescence cell-based assay using PCSK9-WT-mCherry (SEQ. ID. NO. 75) or PCSK9-D374Y-mCherry (SEQ. ID. NO. 76) and LDLR-EGFP (SEQ. ID. NO. 77). Schematic representation of different readouts that could be obtained from PCSK9-mC and LDLR-EGFP co-expressing cells is shown (higher panels). HEK293 were transfected with LDLR-EGFP and incubated for 4 h with WT or D374Y PCSK9-mC containing media obtained from transfected cells without or with 4 nM PCSK9 neutralizing antibody pre-incubated overnight. Selected regions (dashed squares) were 5× zoomed numerically (MAG). Data are representative of at least three independent experiments.

In the case of blockade of PCSK9 internalization and degradation by the hepatic cells but not PCSK9 binding to LDLR, a yellow signal i.e. composite signal of extracellular LDLR conjugated GFP and intracellular PCSK9 conjugated mCherry. A yellow signal indicates cell surface and intracellular localization of PCSK9-mC-LDLR-EGFP complex without degradation (FIG. 15; top panel). In this case any combination of fluorophores can be used that will provide a composite signal that can be reliably distinguished from the signal derived either from a PCSK9 conjugated fluorophore or a LDLR conjugate fluorophore alone.

In a third scenario, a potent PCSK9 inhibitor or removal of critical protein (on that modulates the LDLR-PCSK9 interaction) will give high LDLR-EGFP and low PCSK9-mC levels i.e. a green signal (FIG. 15; top panel). This result would indicate a potential for the compound tested to have lipid-lowering effects in vivo. The predominant signal detected will be from the fluorophore conjugated to LDLR. To validate the dual fluorescence PCSK9-LDLR cell-based assay, it was tested with WT PCSK9-mC (SEQ ID NO 75), or PCSK9-mC with a gain of function (GOF) D374Y mutant (SEQ ID NO 76). The assay comprising each of these 2 PCSK9 variants and LDLR-EGFP expressing HEK293 cells was validated without or with a PCSK9-LDLR neutralizing antibody. Confocal microscopy data clearly showed that the PCSK9 neutralizing antibody strongly prevent binding of WT and D374Y PCSK9-mC (FIG. 15; lower left panels) to LDLR-EGFP and protect LDLR from PCSK9-induced degradation (FIG. 15; lower middle left panels, green), enabling PCSK9-mC and LDLR-EGFP as a simple, specific and cost-effective cell-based assay.

Identification of GRP94 as a New PCSK9 Binding Protein

This study was designed to identify new PCSK9 interacting proteins. Accordingly, we selected the human hepatic HepG2 cell line, which has been commonly used to study LDLR degradation by PCSK9 as it endogenously expresses both proteins. Confluent HepG2 cells from 100 $mm^2$ plates were washed three times in PBS and incubated with 1 mM DSP (dithiobis[succinimidylpropionate]), a thiol-cleavable and cell-permeable cross-linking reagent as described in Materials and Methods. Co-interacting PCSK9 proteins were immunoprecipitated (IP) with anti-PCSK9 polyclonal antibody and separated by SDS-PAGE electrophoresis under reducing conditions (FIG. 1*a*). Following silver staining, we identified a ~100 kDa band co-IP with PCSK9 that was undetectable in cell lysate incubated with the pre-immune serum (−), herein used as a control. Mass spectrometry data from the excised bands revealed SEQ ID. NO. 2 (GRP94/gp96) as the ~100 kDa migrating protein in complex with PCSK9 (Table 1). To further substantiate this interaction, human hepatic Huh-7 and HepG2 cells were transfected with either an empty vector (IRES-V5) or with cDNAs encoding V5-tagged human PCSK9 (PCSK9-V5; FIG. 1*b*). Forty-eight hours post-transfection, cells were cross-linked, proteins IP with mAb-V5 antibody and separated under reducing conditions. More intensely than in HepG2 cells, silver staining highlighted the ~100 kDa band co-IP with PCSK9-V5 in addition to ~76 kDa extra bands (FIG. 1*b*). Mass spectrometry data confirmed the presence of GRP94 in complex with PCSK9 together with GRP78 (also known as the ER stress-related molecular chaperone BiP; FIG. 1*b* and Table 2), the latter most likely due to overexpressing conditions. PCSK9 was also found by mass spectrometry at ~76 kDa corresponding to proPCSK9, the uncleaved PCSK9 form present within the ER. (Seidah et al., 2003) Interestingly, the ~100 kDa band was also detected in HepG2 and Huh-7 cells upon IP of PCSK9 lacking its Cys/His-rich C-terminal domain (CHRD; PCSK9-L455X-V5; FIG. 1*b*). In parallel experiments, immunoblotting confirmed that PCSK9-V5 and PCSK9-L455X-V5 specifically interact in complex with SEQ ID. NO. 3 (FIG. 1*c*). SEQ ID. NO. 3 was barely detectable in lysates IP with mAb-V5 overexpressing either the CHRD alone (PCSK9-CHRD-V5) or human LDLR-V5 (FIG. 1*c*). Conversely, we showed that both proPCSK9 and mature PCSK9-V5 were IP using anti-GRP94 (FIG. 1*d*) and that endogenous PCSK9 and GRP94 were highly co-localized in Huh-7 (FIG. 1*d*), suggesting the ER as a major subcellular interacting compartment. Therefore, we have identified GRP94 as a new PCSK9 intracellular binding protein in human hepatic cell lines both under overexpression and at endogenous levels.

Critical Role of the SEQ ID. NO. 4 for PCSK9 Interaction

Figure 2:
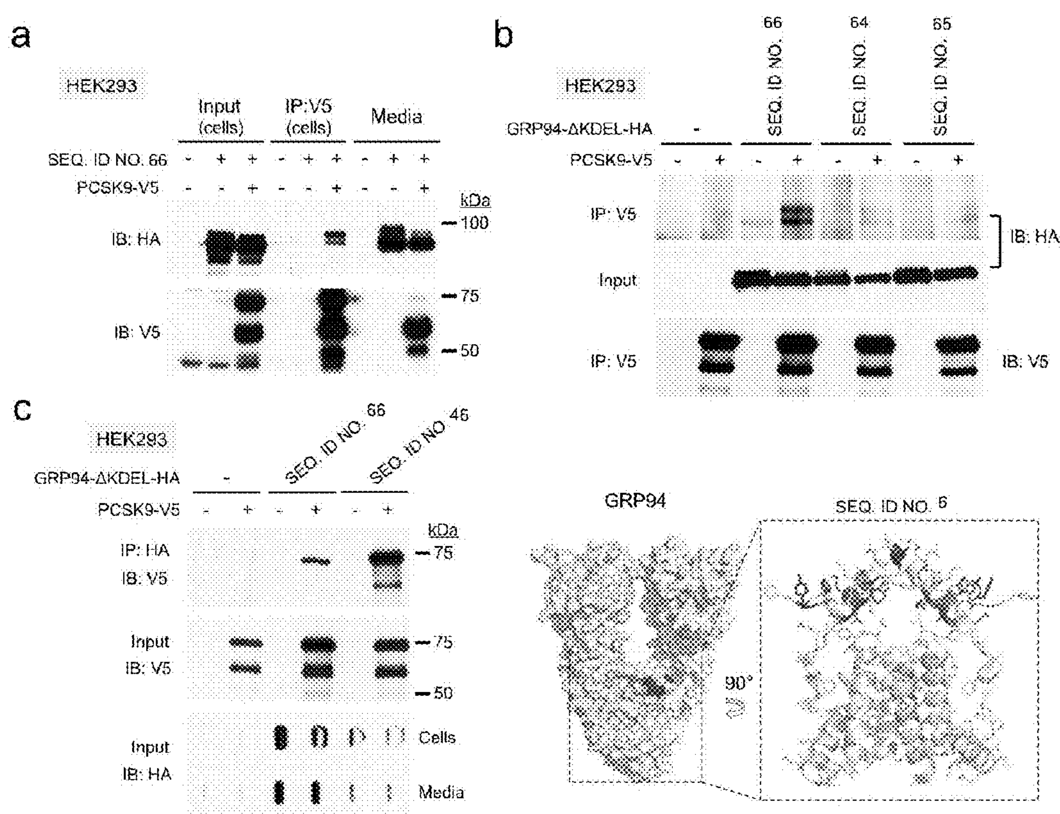
FIG. 2: Mapping of the PCSK9-GRP94 interacting domain. (a-b) HEK293 cells were transfected without (−) or with (+) PCSK9-V5 or SEQ ID NO. 66, 64 or 65. A PCSK9 V5 epitope-tag fusion protein (PCSK9-V5) was immune-precipitated from cell lysates using mAb-V5 antibody (IP: V5) and immune-blotted as indicated. Total GRP94 (SEQ. ID. NO. 3) and PCSK9 (SEQ. ID. NO. 1) protein levels were analyzed by immune-blotting in cell lysates (input) and conditioned media. (c) Left panel; HEK293 cells were transfected without (−) or with (+) PCSK9-V5, SEQ. ID. NO. 66 or 46. PCSK9-V5 was immune-precipitated for cell lysates (IP: V5) and immune-blotted (IB) as indicated. Total GRP94 and PCSK9 protein levels were also analyzed by immune-blotting and herein used as a control (input). Right panel; GRP94 homodimer (gray and yellow) crystal structure was determined from PDB file #2O1V using MacPymol software. This work demonstrates the importance of SEQ ID NO. 6 in which critical residues for PCSK9 binding determined in (b) are indicated in blue for SEQ. ID. NO. 64 and red for SEQ. ID. NO. 65. Data are representative of at least three independent experiments.

We next decided to map GRP94 domain(s) important for PCSK9 protein-protein interaction. The overall domain structure of GRP94 includes a signal polypeptide (amino acids; aa1-21) followed by a N-terminal enzymatic ATP-binding domain (aa22-651), client-binding domain (CBD; aa652-678), C-terminal dimerization domain (aa679-799) and a KDEL polypeptide sequence (aa800-803) allowing retention of GRP94 in the endoplasmic reticulum. (Dollins et al., 2007; Maki et al., 1990; Wu et al., 2012) Thus, we first generated cDNA constructs encoding secretable HA-tagged forms of human GRP94 lacking its C-terminal KDEL polypeptide (SEQ ID. NO. 66; FIG. 2). HEK293 cells were transfected without or with SEQ ID. NO. 66 in absence or presence of PCSK9-V5 (FIG. 2*a*). Immunoblot analysis revealed that SEQ ID. NO. 66 is well expressed (Input; IB: HA) and secreted into media and that SEQ ID. NO. 66 interacts in complex with PCSK9 following immunoprecipitation (IP: V5; FIG. 2*b*). Therefore, we conclude that has endogenous GRP94 (FIG. 1), truncation of the KDEL did not impair interaction with PCSK9 (FIG. 2*a*), which was subsequently used as screening template. It was reported that a 27 aa C-terminal hydrophobic loop structure within GRP94 client-binding domain (CBD, amino acids aa652-678; $^{652}$YGWSGNMERIMKAQAYQTGKDISTNYY, SEQ ID. NO. 4) was important for folding and interaction with Toll-like receptors and integrins. (Wu et al., 2012) Deletion or alanine-scan mutations in SEQ ID. NO. 4 region of GRP94 was shown to not alter its overall structure nor its N-terminal ATPase activity and binding to co-chaperone CNPY3 but prevented interaction with its client proteins. (Wu et al., 2012) Similarly, we generated two mutated constructs in which critical residues within the GRP94-CBD domain where mutated into alanine (AA1: $^{652}$YAAS AAAAAIMKAQAYQTGKDISTNYY, SEQ ID. NO. 78 and AA2: $^{652}$YGWSGNMERIMKAQAYATGKAISTNAA, SEQ ID. NO. 79). HEK293 cells were transfected with either an empty vector (−) or with SEQ ID. NO. 66, 64 or 65 constructs in presence or absence of PCSK9-V5 (FIG. 2*b*). Although SEQ ID. NO. 64 and 65 are expressed at similar levels as GRP94 (FIG. 2*b*; Input), mutations within the region of SEQ ID. NO. 4 abrogate binding to PCSK9 (IP: V5), demonstrating that interaction of PCSK9 with GRP94 require a functional CBD domain. Thence, we truncated the N-terminal enzymatic domain (aa 22-651) encoding a secretable ~20 kDa HA-tagged (SEQ ID. NO. 66) protein containing the CDB and C-terminal domains (CBD-CT; SEQ ID. NO. 46), which have been shown to be sufficient for interaction with client proteins. (Wu et al., 2012) HEK293 cells were transfected with either an empty vector (−), SEQ ID. NO. 66 or SEQ ID. NO. 46 in absence (−) or presence of PCSK9-V5 (+) and protein lysates IP with mAb-HA antibody and immunoblotted for PCSK9 (IB: V5; FIG. 2*c*, left panel). Slot blot analysis revealed that PCSK9 did not affect intra- or extracellular protein levels of SEQ ID. NO. 66 (IB: HA, FIG. 2*c*, Input). Whereas that SEQ ID. NO. 7 was ~5-fold less produced as compared to SEQ ID. NO. 66, truncation of the N-terminal domain of GRP94 significantly enhanced its interaction to PCSK9 (FIG. 2*c*). These data are consistent with the identification of important residues within the solvent exposed 27-aa stretch SEQ ID. NO. 4 (highlighted in red and blue from SEQ ID. NO. 64 and SEQ ID. NO. 65; FIGS. 2*b* and 2*c*, right panel), which reinforce the direct implication of SEQ ID. NO. 4 as an important PCSK9 modulating polypeptide.

GRP94 is not a Molecular Chaperone for PCSK9

It has been demonstrated that proper folding and functions of GRP94 client proteins directly corroborate with their CBD binding. (Wu et al., 2012) Despite its limited number of client proteins, (McLaughlin and Vandenbroeck, 2011) we next wanted to determine whether GRP94 is a direct molecular chaperone for PCSK9. HepG2 cells were incubated for 24 h with vehicle (DMSO) or with 1 or 5 μM Geldanamycin (GA), a small molecule competitive inhibitor of the N-terminal ATP binding site of GRP94 (also known as HSP90b1) and its cytosolic paralog Hsp90. (Dollins et al., 2007; McLaughlin and Vandenbroeck, 2011; Stebbins et al., 1997) Immunoblot analysis revealed that geldanamycin treatment did not affect PCSK9 and LDLR total protein levels, proPCSK9 to PCSK9 autocatalytic activation, and PCSK9 secretion in the media (FIG. 3*a*), eliminating a role for GRP94 as a PCSK9 direct chaperone. To further substantiate those observations, HEK293 cells were transfected with either non-targeting siRNA (−) or with siRNAs against human GRP94 (+) alone or together with wild-type PCSK9-V5 or its high LDLR affinity gain-of-function D374Y mutant (FIG. 3*b*). (Poirier and Mayer, 2013) Forty-hours later, cells were washed, incubated in DMEM for 24 h and PCSK9 immunoprecipiated from cell lysates 72 h post-transfection with mAb-V5 antibody. Immunoblotting revealed efficient siRNA-mediated knockdown (KD) of endogenous GRP94, which clearly demonstrated the specificity of GRP94-PCSK9 interaction by the almost undetectable signal of GRP94 followed PCSK9 IP (FIG. 3*b*; IP: V5, IB: GRP94). Interestingly, both WT and PCSK9-D374Y mutant were comparably co-IP in complex with GRP94 and were able to induce intracellular LDLR degradation even in absence of GRP94 in HEK293 cells (FIG. 3*b*; Input, left panel) or following media swap on naïve HepG2 cells (FIG. 3*b*; Input, right panel). Consistent with enzymatic inhibition of GRP94 (FIG. 3*a*), KD of GRP94 did not alter PCSK9 total protein levels, autocatalytically (proPCSK9→PCSK9) and furin-regulated processing (PCSK9-$\Delta N_{218}$)(Benjannet et al., 2006), nor its secretion (FIG. 3*b*; IB: V5, Cond. Media) maintaining its full capacity to induce LDLR degradation both via intra- and extracellular pathways (FIG. 3*b*). This suggests that binding of PCSK9 to GRP94-CBD (FIG. 2) would not correlated with its chaperoning function in the ER but (FIG. 3), according to our knowledge, would rather be the first evidence of a role as an interacting protein.

GRP94 KD Increase Sensitivity to PCSK9-Induced LDLR Degradation

Figure 4:
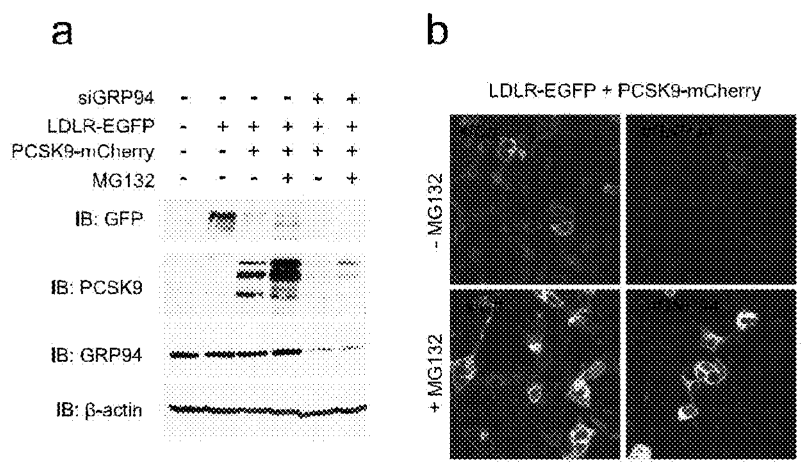
FIG. 4: Knockdown of GRP94 increases LDLR degradation by PCSK9. At day 0, HEK293 cells were transfected either with a non-targeting siRNA (−) or with siRNAs against GRP94 (+). At day 1, cells were transfected with an empty vector (−) or with plasmids encoding for LDLR-EGFP (SEQ. ID. NO. 69) alone or in combination with PCSK9-mCherry (SEQ. ID. NO. 70). At day 2, cells were washed and incubated overnight with DMSO (−) or 5 μM MG132 overnight in complete media. (a) Total LDLR-EGFP, PCSK9-mCherry, GRP94 and β-actin protein levels were analyzed by immune-blotting in cell lysates as indicated. (b) LDLR-GFP and PCSK9-mCherry were visualized in live cells by confocal microscopy as conditions described above. Data are representative of at least three independent experiments.

To decipher the role of GRP94 on PCSK9, we took advantage of HEK293 cells, as they are easily transfectable in addition to be PCSK9-negative. (Seidah et al., 2003) Cells were transfected with either non-targeting siRNA (−) or with siRNAs against human GRP94 (+) and 24 h later without (−) or plasmids encoding for fluorescent PCSK9-mCherry or LDLR-EGFP (FIG. 4). Twenty-hours post cDNA transfections, cells were incubated either with vehicle (DMSO) or 5 μM MG132, a proteasome inhibitor. As shown in FIG. 4*a*, C-terminal fusion of either EGFP to LDLR (lane 2) or mCherry to PCSK9 (lane 3) are well tolerated upon transfection in HEK293 cells and that PCSK9-mCherry preserve its capacity to induced LDLR-EGFP degradation (lane 3). Interestingly, immunoblot (FIG. 4*a*, lane 5) and confocal microscopy (FIG. 4*b*, top panels) analyses revealed that KD of GRP94 renders LDLR much more sensitive to PCSK9-induce degradation that was not blocked by addition of the proteasome inhibitor MG132 similar as previously described. (Maxwell et al., 2005) These data suggest that, while not being involved in chaperoning of PCSK9, GRP94-PCSK9 complex formation could prevent early PCSK9 binding to LDLR and thus limiting its subsequent degradation.

SEQ ID. NO. 4 Reduces PCSK9 Internalization and LDLR Degradation

Figure 5:
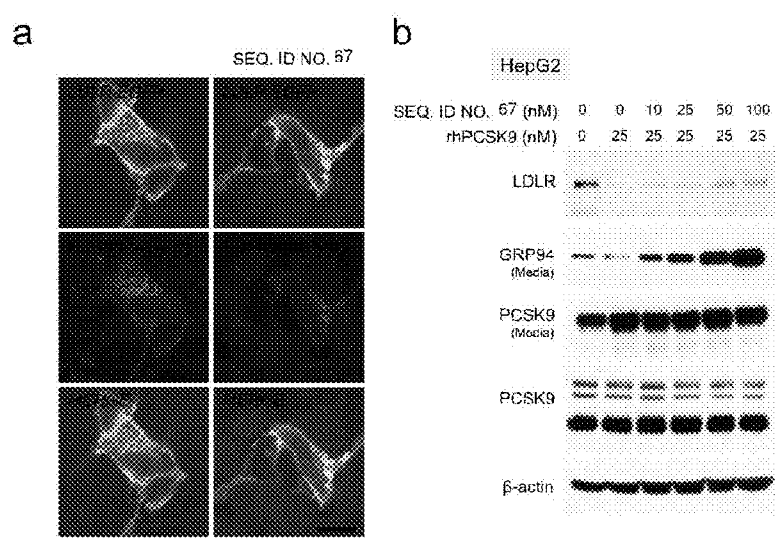
FIG. 5: SEQ ID NO. 67 blocks PCSK9 internalization and LDLR degradation. Recombinant SEQ ID NO. 67 was added to conditioned media obtained from HEK293 transfected with PCSK9-mCherry or in DMEM together with recombinant human PCSK9, rotated 4 h at 4° C. and added overnight on HepG2 cells as indicated. (a) Following 24 h post-transfection with LDLR-EGFP cDNA (SEQ. ID. NO. 69), HepG2 cells were incubated with PCSK9-mCherry without (−) or with 10 nM SEQ ID NO. 67. Fluorescent proteins were visualized in fixed cells by confocal microscopy. (b) Cells were incubated without or with 25 nM PCSK9 alone or with 0, 10, 25 or 100 nM SEQ ID NO. 67. Total LDLR, SEQ ID NO. 67, PCSK9 and β-actin protein levels were analyzed by immunoblotting in cell lysates and conditioned media as indicated. Data are representative of at least three independent experiments.

To validate this hypothesis, we therefore first tested the effect of extracellular SEQ ID. NO. 67 on PCSK9 internalization. Recombinant SEQ ID. NO. 67 was added to conditioned media obtained from HEK293 cells transfected with PCSK9-mCherry and incubated by rotation 4 h at 4° C. and incubated overnight on HepG2 cells transiently transfected with LDLR-EGFP (FIG. 5*a*). Confocal microscopy analysis revealed that PCSK9-mCherry internalization was significantly reduced in LDLR-EGFP expressing cells in the presence of extracellular (+ rcGRP94, SEQ ID. NO. 67) as compared to control (− rcGRP94, SEQ ID. NO. 67; FIG. 5*a*). Thereafter, we wanted to study the impact of extracellular SEQ ID. NO. 67 on PCSK9-induced LDLR degradation. HepG2 cells were incubated overnight without or with recombinant PCSK9 in presence of an increasing amount of rcGRP94 (SEQ ID. NO.67; FIG. 5*b*). Immunoblot data revealed that PCSK9 significantly induces LDLR degradation, which can be reverted in a dose-dependent manner by exogenous addition of SEQ ID. NO. 67. We also noted that HepG2 cells endogenously secrete ~5 nM SEQ ID. NO. 3 that has not prevented LDLR degradation following addition of 25 nM PCSK9 (FIG. 5*b*; lane 2) but rather might be sufficient under PCSK9 endogenous conditions. Those data demonstrated that exogenous addition of SEQ ID. NO. 67 inhibits PCSK9-induced LDLR degradation by blocking its internalization by the LDLR.

In Vitro Competitive Assay of SEQ ID. NO. 6 on PCSK9-LDLR Binding

Figure 6:
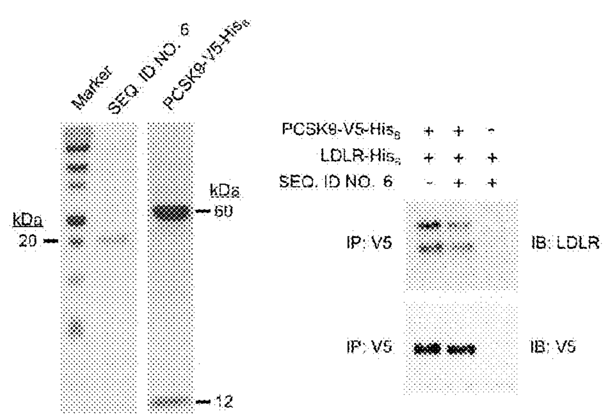
FIG. 6: SEQ ID NO. 6 reduces PCSK9 binding to LDLR in vitro. Left; Coomassie staining of $His_6$ tag purified recombinant SEQ ID NO. 6 and PCSK9 produced as described in Material and Methods. Right; PCSK9-V5-$His_6$ (1 μg) was incubated without (−) or with (+) recombinant SEQ ID NO. 6 (2 μg) in 500 μl of immune-precipitation (IP) buffer (PBS, 1 mM $CaCl_2$, 1% Tween-20 and protease inhibitors) for 4 h at 4° C. on a rotator. Following incubation, 1 μg of recombinant human LDLR ectodomain was added together with 50 μl of A/G-agarose beads and 1 μg of mAb-V5 antibody and incubated with rotation overnight. Samples were then centrifuged at 3,000×g for 5 min and pellets washed three times with 1 ml IP buffer and rotated for 10 min 4° C. and resuspended in 2× Laemmli loading buffer. Samples were separated by SDS-PAGE and immune-blotted as indicated. Data are representative of two independent experiments.

Biochemical and crystallographic studies demonstrated that surface of PCSK9 catalytic domain directly binds to the extracellular EGF-A domain of LDLR. (Kwon et al., 2008; Zhang et al., 2007) By co-IP experiments, we showed that PCSK9-GRP94 complex formation involves the PCSK9 proregion-catalytic domains (FIG. 1*c*) and the SEQ ID. NO. 6 (FIG. 2), suggesting that the inhibitory effect of SEQ ID. NO. 3 might be due to direct competition for PCSK9 binding to the LDLR. To test this hypothesis, we subcloned the SEQ ID. NO. 6 into the pET-24 bacterial expressing vector of which recombinant protein were retrieved from *E. coli* and purified by metal affinity and size exclusion chromatography. The homogeneity of purified SEQ ID. NO. 6(~20 kDa) and recombinant PCSK9 purified from conditioned media of HEK293 transfected cells were assessed by SDS-PAGE and coomassie staining (FIG. 6; left panels). For in vitro PCSK9-LDLR competitive assays, 1 μg PCSK9 was prior incubated without (−) or with 1 μg of SEQ ID. NO. 6 for 4 h and incubated by rotation overnight at 4° C. with 1 μg LDLR together with mAb-V5 antibody and A/G-agarose beads. Immunoblot analysis showed that LDLR was specifically pull-down with PCSK9 that can be partially inhibited in the presence of SEQ ID. NO. 6 (FIG. 6; right panel, lane 2).

SEQ ID. NO. 10 Inhibits PCSK9-Induced LDLR Degradation

Figure 7:
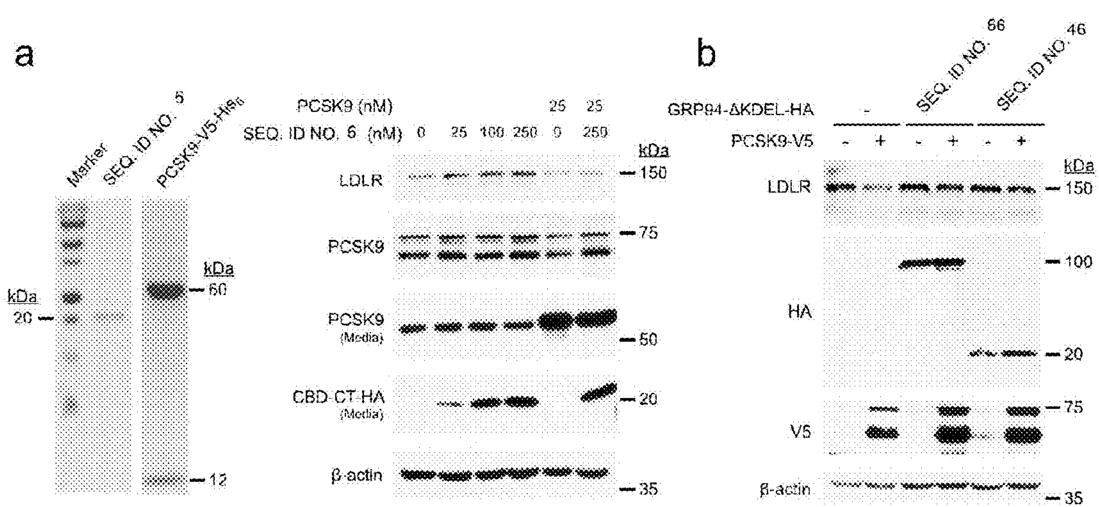
FIG. 7: SEQ ID NO. 6 prevents PCSK9-induced LDLR degradation. (a) Left; Coomassie staining of purified recombinant SEQ ID NO. 6 and PCSK9 separated by SDS-PAGE is shown. Right; HepG2 cells were incubated in DMEM without or with 0, 25, 100 or 250 nM SEQ ID NO. 6 alone or in presence of recombinant PCSK9. (b) HepG2 cells were transfected without (–) or with PCSK9-V5 in absence (–) or presence SEQ ID NO. 66 or SEQ ID NO. 46. Total LDLR, PCSK9, SEQ ID NO. 66, SEQ ID NO. 46 and β-actin protein levels were analyzed by immunoblotting in cell lysates and conditioned media as indicated. Data are representative of at least three independent experiments.

We next tested whether SEQ ID. NO. 6 could alter the capacity of PCSK9 to induce LDLR degradation. HepG2 cells were incubated overnight with an increasing amount of recombinant SEQ ID. NO. 6 in absence or presence of exogenous PCSK9 (FIG. 7*a*). Immunoblot revealed that extracellular addition of SEQ ID. NO. 6 significantly increases total LDLR protein levels, for which maximum effect was already saturated at 25 nM. Although that SEQ ID. NO. 6 appears to significantly block endogenously secreted PCSK9, 250 nM SEQ ID. NO. 6 was not sufficient to block exogenously added PCSK9 (~6-fold endogenous levels; FIG. 7*a*). (Poirier et al., 2009) As PCSK9 was also shown to induce LDLR degradation via an intracellular pathway, (Poirier et al., 2009) we evaluated to ability of SEQ ID. NO. 66 or SEQ ID. NO. 46 to neutralize PCSK9 in HepG2 cells following co-expression (FIG. 7*b*). Similar to the extracellular pathway (FIGS. 5*b* and 7*a*), both SEQ ID. NO. 66 and SEQ ID. NO. 46 significantly block LDLR degradation induced by overexpression of PCSK9 in HEK293 cells (FIG. 7*b*). Overall, these data demonstrated that SEQ ID. NO. 66 and specifically SEQ ID. NO. 46 as inhibitory effect on PCSK9 binding to LDLR and its subsequent degradation most likely via a direct protein-protein interaction.

Hepatic Grp94 Controls Circulating LDL-C by Maintaining LDLR Protein Levels

Figure 8:
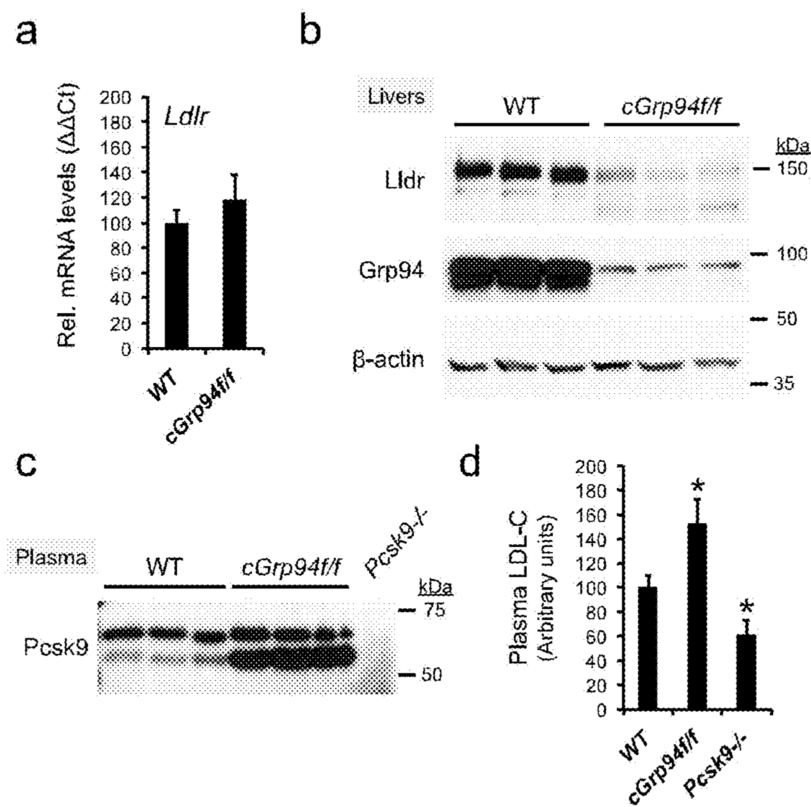
FIG. 8: Lldr protein levels are strongly decreased in cGrp94$^{f/f}$ mice. (a) Relative mRNA levels of Ldlr were measured by quantitative RT-PCR in 2 months-old wild-type littermates (WT) and hepatocyte-specific Grp94 knockout male mice (cGrp94$^{f/f}$. (b) Total LDLR, Grp94 and β-actin protein levels were analyzed by immune-blotting in livers of WT and cGrp94$^{f/f}$ mice. (c) Circulating Pcsk9 was immune-precipitated and relative circulating levels were determined by immune-blotting in WT and cGrp94$^{f/f}$ mice. Plasma from Pcsk9$^{-/-}$ mice was used as negative control. (d) Plasma LDL-Cholesterol levels were measured in WT, cGrp94$^{f/f}$ and Pcsk9$^{-/-}$ mice a normalized to that of WT littermates. Data and error bars are representative of n=6 animals/group analyzed in duplicate.

We next wanted to extend our observations and study the role of Grp94 in vivo. The liver plays a major role in the regulation of circulating LDL-Cholesterol through cell surface LDLR in addition to be the far most abundant tissue expressing Pcsk9, exclusively secreted in plasma by hepatocytes. (Goldstein and Brown, 1987; Seidah et al., 2003; Zaid et al., 2008) Accordingly, floxed-Grp94 mice were crossed with albumin-Cre transgenic mice to generate hepatocyte-specific Grp94 deficient mice therefore named cGrp94f/f. (Chen et al., 2014) While Ldlr mRNA levels were not affected by the absence of Grp94 (FIG. 8*a*), we observed a severe decrease in total Ldlr protein levels in livers of cGrp94f/f reminiscent of PCSK9-overexpressing transgenic mice (FIG. 8*b*). (Zaid et al., 2008) Similar to Ldlr-deficient mice, we also noticed that total and furin-cleaved circulating Pcsk9 levels were elevated in plasma of cGrp94f/f mice (FIG. 8*c*). As observed in our ex vivo GRP94 KD experiments (FIG. 3*b*), we confirmed that Grp94 is not a direct chaperone of Pcsk9 as reflected by its large amount secreted into the plasma of cGrp94f/f mice (FIG. 8*c*). In agreement with low Ldlr levels in cGrp94f/f mice livers, we measured a significant ~50% increase in circulating LDL-Cholesterol (FIG. 8*d*). Interestingly, this difference is similar to the reduction observed in Pcsk9-deficient mice (FIG. 8*d*; Pcsk9−/−). Those cumulative data revealed that GRP94 is a master regulator of LDL-C and LDLR protein levels both ex vivo and in vivo, likely by preventing PCSK9 binding to the LDLR.

Proposed Model for GRP94 Inhibitory Effect on PCSK9-Induced LDLR Degradation

Based on our data, we showed that in absence of GRP94, LDLR total protein levels are severely decreased leading to increase circulating PCSK9 and LDL-C in the plasma (FIG. 9; left panel). This can be explained by the observations that LDLR was much more sensitive to degradation by PCSK9 upon GRP94 KD in HEK293 cells (FIG. 4), suggesting that GRP94 binding to PCSK9 as an underlying mechanism. Conversely, we speculate that in physiological conditions, GRP94 within the ER acts as a protein-protein binding partner to PCSK9 preventing hasty binding to LDLR thus avoiding early degradation of the receptor via intra- or extracellular pathways (FIG. 9; Right panel). This new underline protection mechanism allows the liver to control LDL-C by maintaining LDLR total protein levels without leading to complete degradation within hepatocytes.

Structure of the SEQ ID. NO. 4 Polypeptide Binding to PCSK9

Figure 10:
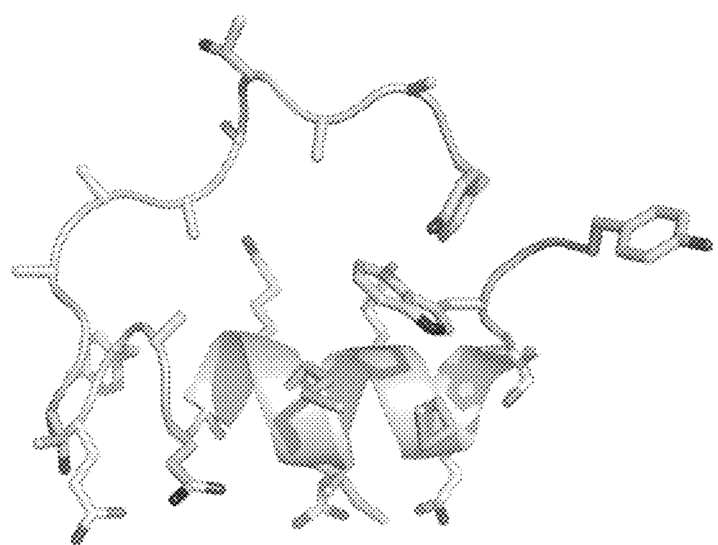
FIG. 10: Crystal structure of the SEQ ID NO. 4 interacting with PCSK9. Structure of the SEQ ID NO. 4 was determined by MacPymol and derived from SEQ ID NO. 3 homodimer crystal (PDB #2O1V).
Figure 14:
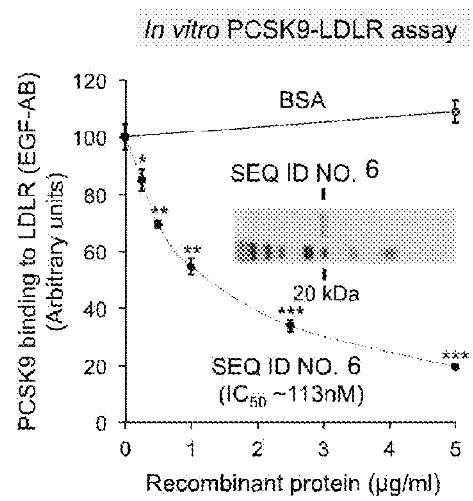
FIG. 14: The inhibitory effect of SEQ ID NO. 6 on PCSK9-LDLR (EGF-AB) binding was analyzed by in vitro competitive assay. Recombinant human SEQ ID NO. 6 was purified and inhibits PCSK9 binding to LDLR (EGF-AB domain) with an IC50 of ~113 nM). Coomassie staining of SEQ ID NO. 6 is shown. Data represent means of two independent experiments analyzed in duplicate±S.D. *p<0.05; p<0.01; *p<0.001.

APCSK9 interacting domain of GRP94 was determined from the full-length GRP94 crystal structure PDB #2O1V (FIG. 10). Ribbon structure of the SEQ ID. NO. 4 (aa652-678; $^{652}$YYGWSGNMERIMKAQAYQTGKDISTNYY) with side chains are represented and propose to be used as a PCSK9 interacting polypeptide or peptidomimetic template to inhibit PCSK9 activities such in the context of LDLR degradation and/or systemic inflammation.

Example 2

Peptide encoded by SEQ ID. NO. 4 (YGWSGNMERIMKAQAYQTGKDISTNYY) was synthesized on rink amide resin using a Tribute peptide synthesizer (Protein Technologies) by standard Fmoc chemistry. After cleavage from the solid support, crude peptide was precipitated and washed with diethyl ether, recovered by vacuum filtration, and dissolved in distilled water before being lyophilized. Peptide was purified by reverse-phase high performance liquid chromatography (RP-HPLC) on a preparative Luna C18 column (250 mm×21.2 mm, 5 μm, 100 Å, Phenomenex) with a linear gradient of acetonitrile (ACN) in TFA/H2O (0.06% v/v). Collected fractions were analyzed by analytical RP-HPLC using a Kinatex EVO C18 column (150 mm×4.6 mm, 3.6 μm, Phenomenex) and mass-verified by electrospray ionization time-of-flight mass spectrometry (ESI-TOF MS). Fractions containing SEQ 04 at 95% purity or greater as measured by RP-HPLC were pooled and lyophilized. Peptides were stored dry at −20° C.

Figure 16:
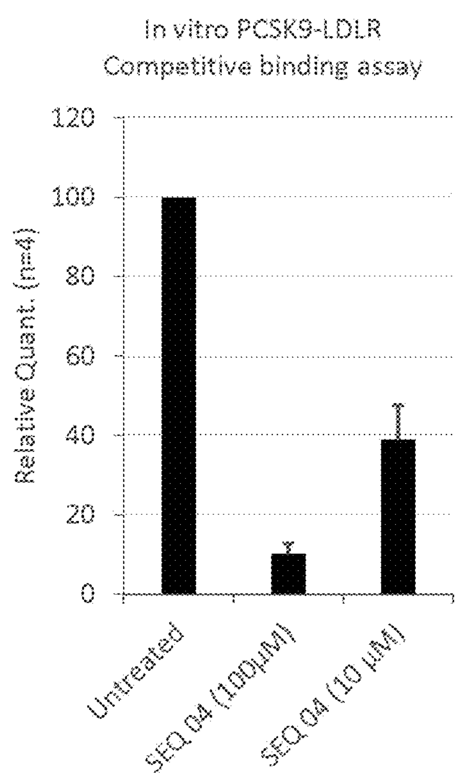
FIG. 16: A peptide including SEQ. ID. NO. 4. inhibits binding of PCSK9 to the LDLR EGFA domain.

SEQ ID. NO. 4 peptide was dissolved to 10 mM (working dilution) in DMEM media (Wisent Cat. #319-005-CL). In a total of 100 μl reaction buffer (HEPES buffer containing NaCl, $CaCl_2$), BSA and proclin 300, pH6.1), SEQ ID. NO. 4 were added to a final concentration of 100 or 10 μM together with 100 ng wild-type human recombinant His-tagged PCSK9. Reaction buffer was added to 96 wells coated with recombinant LDLR-EGFA domain (involved in PCSK9-LDLR interaction) and incubated at room temperature for 2 h on an orbital microplate shaker (300 rpm). Following incubation, wells were washed 4 times with wash buffer and biotinylated anti-His-tag monoclonal antibody was added into each well and incubated for 1 h at room temperature. Following incubation wells were washed 4 times, and HRP-conjugated streptatvidin was added to each well and incubated for 20 min. Following 4 washes, 100 μl substrate reagent (TMB, tetra-methylbenzidine) were added for 15 min to each wells and enzymatic reaction stopped by adding 100 μl stop solution (1N NH2SO4). For each well, absorbance at 450 nm and 540 nm was measure and relative PCSK9 binding to LDLR-EGFA was determined according to a standard curve (100 ng to 1.56 ng). Inhibitory activities of SEQ ID. No. 4 was tested in separated triplicates and dose-response for PCSK9-LDLR inhibition (Evolocumab, PCSK9 mAbs; herein used as comparator positive control) was also performed in parallel on each plate. Results are shown in FIG. 16.

It has been previously shown that the surface of PCSK9 catalytic domain directly interacts with the EGF-A domain of the low-density lipoprotein receptor (LDLR). Therefore, this underlying mechanism of action was the premise that lead to the development of neutralizing humanized PCSK9 monoclonal antibodies (such as Evolocumab™), currently indicated to treat patients with familial hypercholesterolemia and/or history of atherosclerotic cardiovascular diseases on top of statins. It has been observed clinically that antibodies binding to the surface of PCSK9 catalytic domain result in lowering of circulating LDL Using an in vitro PCSK9-LDLR(EGFA) competitive assay, data showed that peptide encoding SEQ ID. NO. 4 (first 27 aa of SEQ 06) inhibit binding of PCSK9 to the LDLR EGFA domain. Thus, we conclude that similar to Evolocumab, binding of SEQ ID. NO. 4 to PCSK9 is concomitant to its inhibitory effect on PCSK9-LDLR a validated molecular target to reduce circulating LDL-cholesterol. Similarly to Evolocumab, the proposed peptides of the invention will reduce circulating LDL-cholesterol without all the disadvantages related to monoclonal antibody therapy. Of course, peptides shorter or longer than those of SEQ. ID. 4 are usable to reduce circulating LDL-cholesterol, as long as the portion of SEQ. ID. 4 or homologous portions thereof that bind to PCSK9 are exposed after folding of the peptide.

In some embodiments, the polypeptide preserves the residues identified in the results of FIG. 2 as reducing binding to PCSK9 when replaced with Ala, optionally with the substitutions set forth in table 2 which are known to have little effect on protein functions. Peptide of the present invention may be less than 40, less than 60, less than 80, less than 100, less than 120, or less than 140 amino acids in length in some embodiments. The structure of such small peptides can be computed before synthesis, which allows to determine a sequence of amino acids that will expose a subsequence having a structure and properties close to those of SEQ. ID. 4, and which therefore will bind to PCSK9. For example, the peptides could include as a subsequence YGWX1GNX2EX3X4X5X6DX7YY Wherein X1 is S or T, X2 is M or Z, X3 is R or K, X4 is IMKAQAY, or any suitable amino acid sequence of between 3 and 10 amino acids in length, X5 is Q or D, X6 is TGK or any suitable amino acid sequence of between 2 and 6 amino acids in length, X7 is ISTN or any suitable amino acid sequence of between 2 and 10 amino acids in length.

REFERENCES

Abifadel, M., Rabes, J. P., Devillers, M., Munnich, A., Erlich, D., Junien, C., Varret, M., and Boileau, C. (2009). Mutations and polymorphisms in the proprotein convertase subtilisin kexin 9 (PCSK9) gene in cholesterol metabolism and disease. Hum. Mutat. 30, 520-529.

Abifadel, M., Varret, M., Rabes, J. P., Allard, D., Ouguerram, K., Devillers, M., Cruaud, C., Benjannet, S., Wickham, L., Erlich, D., et al. (2003). Mutations in PCSK9 cause autosomal dominant hypercholesterolemia. Nat. Genet. 34, 154-156.

Aimiuwu, J., Wang, H., Chen, P., Xie, Z., Wang, J., Liu, S., Klisovic, R., Mims, A., Blum, W., Marcucci, G., et al. (2012). RNA-dependent inhibition of ribonucleotide reductase is a major pathway for 5-azacytidine activity in acute myeloid leukemia. Blood 119, 5229-5238.

Baigent, C., Blackwell, L., Emberson, J., Holland, L. E., Reith, C., Bhala, N., Peto, R., Barnes, E. H., Keech, A., Simes, J., et al. (2010). Efficacy and safety of more intensive lowering of LDL cholesterol: a meta-analysis of data from 170,000 participants in 26 randomised trials. Lancet 376, 1670-1681.

Benjannet, S., Rhainds, D., Essalmani, R., Mayne, J., Wickham, L., Jin, W., Asselin, M. C., Hamelin, J., Varret, M., Allard, D., et al. (2004). NARC-1/PCSK9 and its natural mutants: zymogen cleavage and effects on the low density lipoprotein (LDL) receptor and LDL cholesterol. J. Biol. Chem. 279, 48865-48875.

Benjannet, S., Rhainds, D., Hamelin, J., Nassoury, N., and Seidah, N. G. (2006). The proprotein convertase (PC) PCSK9 is inactivated by furin and/or PC5/6A: functional consequences of natural mutations and post-translational modifications. J. Biol. Chem. 281, 30561-30572.

Berge, K. E., Ose, L., and Leren, T. P. (2006). Missense mutations in the PCSK9 gene are associated with hypocholesterolemia and possibly increased response to statin therapy. Arterioscler. Thromb. Vasc. Biol. 26, 1094-1100.

Brown, M. S., and Goldstein, J. L. (1986). A receptor-mediated pathway for cholesterol homeostasis. Science 232, 34-47.

Bruckert, E., Hayem, G., Dejager, S., Yau, C., and Begaud, B. (2005). Mild to moderate muscular symptoms with high-dosage statin therapy in hyperlipidemic patients—the PRIMO study. Cardiovasc. Drugs Ther. 19, 403-414.

Chan J C, Piper D E, Cao Q et al. A proprotein convertase subtilisin/kexin type 9 neutralizing antibody reduces serum cholesterol in mice and nonhuman primates. *Proc Natl Acrid Sci USA*. 2009; 106(24):9820-9825.

Chen, W. T., Tseng, C. C., Pfaffenbach, K., Kanel, G., Luo, B., Stiles, B. L., and Lee, A. S. (2014). Liver-specific knockout of GRP94 in mice disrupts cell adhesion, activates liver progenitor cells, and accelerates liver tumorigenesis. Hepatology 59, 947-957.

Cloutier, P., Al-Khoury, R., Lavallee-Adam, M., Faubert, D., Jiang, H., Poitras, C., Bouchard, A., Forget, D., Blanchette, M., and Coulombe, B. (2009). High-resolution mapping of the protein interaction network for the human transcription machinery and affinity purification of RNA polymerase II-associated complexes. Methods 48, 381-386.

Cohen, J., Pertsemlidis, A., Kotowski, I. K., Graham, R., Garcia, C. K., and Hobbs, H. H. (2005). Low LDL cholesterol in individuals of African descent resulting from frequent nonsense mutations in PCSK9. Nat. Genet. 37, 161-165.

Cohen, J. C., Boerwinkle, E., Mosley, T. H., Jr., and Hobbs, H. H. (2006). Sequence variations in PCSK9, low LDL, and protection against coronary heart disease. N. Engl. J. Med. 354, 1264-1272.

Cunningham, D., Danley, D. E., Geoghegan, K. F., Griffor, M. C., Hawkins, J. L., Subashi, T. A., Varghese, A. H., Ammirati, M. J., Culp, J. S., Hoth, L. R., et al. (2007). Structural and biophysical studies of PCSK9 and its mutants linked to familial hypercholesterolemia. Nat Struct Mol Biol 14, 413-419.

Dollins, D. E., Warren, J. J., Immormino, R. M., and Gewirth, D. T. (2007). Structures of GRP94-nucleotide complexes reveal mechanistic differences between the hsp90 chaperones. Mol. Cell 28, 41-56.

Dubuc, G., Chamberland, A., Wassef, H., Davignon, J., Seidah, N. G., Bernier, L., and Prat, A. (2004). Statins upregulate PCSK9, the gene encoding the proprotein convertase neural apoptosis-regulated convertase-1 implicated in familial hypercholesterolemia. Arterioscler. Thromb. Vasc. Biol. 24, 1454-1459.

Goldstein, J. L., and Brown, M. S. (1987). Regulation of low-density lipoprotein receptors: implications for pathogenesis and therapy of hypercholesterolemia and atherosclerosis. Circulation 76, 504-507.

Heidenreich, P. A., Trogdon, J. G., Khavjou, O. A., Butler, J., Dracup, K., Ezekowitz, M. D., Finkelstein, E. A., Hong, Y., Johnston, S. C., Khera, A., et al. (2011). Forecasting the future of cardiovascular disease in the United States: a policy statement from the American Heart Association. Circulation 123, 933-944.

Hooper, A. J., Marais, A. D., Tanyanyiwa, D. M., and Burnett, J. R. (2007). The C679X mutation in PCSK9 is present and lowers blood cholesterol in a Southern African population. Atherosclerosis 193, 445-448.

Horton, J. D., Shah, N. A., Warrington, J. A., Anderson, N. N., Park, S. W., Brown, M. S., and Goldstein, J. L. (2003). Combined analysis of oligonucleotide microarray data from transgenic and knockout mice identifies direct SREBP target genes. Proc. Natl. Acad. Sci. U.S.A. 100, 12027-12032.

Hou, R., and Goldberg, A. C. (2009). Lowering low-density lipoprotein cholesterol: statins, ezetimibe, bile acid sequestrants, and combinations: comparative efficacy and safety. Endocrinol. Metab. Clin. North Am. 38, 79-97.

Jorgensen, M. M., Jensen, O. N., Holst, H. U., Hansen, J. J., Corydon, T. J., Bross, P., Bolund, L., and Gregersen, N. (2000). Grp78 is involved in retention of mutant low density lipoprotein receptor protein in the endoplasmic reticulum. J. Biol. Chem. 275, 33861-33868.

Kannel, W. B., Dawber, T. R., Kagan, A., Revotskie, N., and Stokes, J., 3rd (1961). Factors of risk in the development of coronary heart disease—six year follow-up experience. The Framingham Study. Ann. Intern. Med. 55, 33-50.

Kapur, N. K., and Musunuru, K. (2008). Clinical efficacy and safety of statins in managing cardiovascular risk. Vasc Health Risk Manag 4, 341-353.

Kwon, H. J., Lagace, T. A., McNutt, M. C., Horton, J. D., and Deisenhofer, J. (2008). Molecular basis for LDL receptor recognition by PCSK9. Proc. Natl. Acad. Sci. U.S.A. 105, 1820-1825.

Lagace, T. A., Curtis, D. E., Garuti, R., McNutt, M. C., Park, S. W., Prather, H. B., Anderson, N. N., Ho, Y. K., Hammer, R. E., and Horton, J. D. (2006). Secreted PCSK9 decreases the number of LDL receptors in hepatocytes and in livers of parabiotic mice. J. Clin. Invest. 116, 2995-3005.

Lee, A. S. (2014). Glucose-regulated proteins in cancer: molecular mechanisms and therapeutic potential. Nature reviews. Cancer 14, 263-276.

Leigh, S. E., Foster, A. H., Whittall, R. A., Hubbart, C. S., and Humphries, S. E. (2008). Update and analysis of the University College London low density lipoprotein receptor familial hypercholesterolemia database. Ann. Hum. Genet. 72, 485-498.

Leigh, S. E., Leren, T. P., and Humphries, S. E. (2009). Commentary PCSK9 variants: A new database. Atherosclerosis 203, 32-33.

Lusis, A. J. (2000). Atherosclerosis. Nature 407, 233-241.

Macer, D. R., and Koch, G. L. (1988). Identification of a set of calcium-binding proteins in reticuloplasm, the luminal content of the endoplasmic reticulum. J. Cell Sci. 91 (Pt 1), 61-70.

Mackay, J., and Mensah, G. A. (2004). The Atlas of Heart Disease and Stroke. World Health Organization, 112p.

Maki, R. G., Old, L. J., and Srivastava, P. K. (1990). Human homologue of murine tumor rejection antigen gp96: 5'-regulatory and coding regions and relationship to stress-induced proteins. Proc. Natl. Acad. Sci. U.S.A. 87, 5658-5662.

Marduel, M., Ouguerram, K., Serre, V., Bonnefont-Rousselot, D., Marques-Pinheiro, A., Erik Berge, K., Devillers, M., Luc, G., Lecerf, J. M., Tosolini, L., et al. (2013). Description of a large family with autosomal dominant hypercholesterolemia associated with the APOE p. Leu167del mutation. Hum. Mutat. 34, 83-87.

Maxwell, K. N., and Breslow, J. L. (2004). Adenoviral-mediated expression of Pcsk9 in mice results in a low-density lipoprotein receptor knockout phenotype. Proc. Natl. Acad. Sci. U.S.A. 101, 7100-7105.

Maxwell, K. N., Fisher, E. A., and Breslow, J. L. (2005). Overexpression of PCSK9 accelerates the degradation of the LDLR in a post-endoplasmic reticulum compartment. Proc. Natl. Acad. Sci. U.S.A. 102, 2069-2074.

Maxwell, K. N., Soccio, R. E., Duncan, E. M., Sehayek, E., and Breslow, J. L. (2003). Novel putative SREBP and LXR target genes identified by microarray analysis in liver of cholesterol-fed mice. J. Lipid Res. 44, 2109-2119.

McLaughlin, M., and Vandenbroeck, K. (2011). The endoplasmic reticulum protein folding factory and its chaperones: new targets for drug discovery? Br. J. Pharmacol. 162, 328-345.

McNutt, M. C., Lagace, T. A., and Horton, J. D. (2007). Catalytic activity is not required for secreted PCSK9 to reduce low density lipoprotein receptors in HepG2 cells. J. Biol. Chem. 282, 20799-20803.

Müller, C. (1938). Xanthoma, hypercholesterolemia, angina pectoris. Acta Med Scand Suppl., 75-84.

Nassoury, N., Blasiole, D. A., Tebon Oler, A., Benjannet, S., Hamelin, J., Poupon, V., McPherson, P. S., Attie, A. D., Prat, A., and Seidah, N. G. (2007). The cellular trafficking of the secretory proprotein convertase PCSK9 and its dependence on the LDLR. Traffic 8, 718-732.

O'Keefe, J. H., Jr., Cordain, L., Harris, W. H., Moe, R. M., and Vogel, R. (2004). Optimal low-density lipoprotein is 50 to 70 mg/dl: lower is better and physiologically normal. J. Am. Coll. Cardiol. 43, 2142-2146.

Park, S. W., Moon, Y. A., and Horton, J. D. (2004). Post-transcriptional regulation of low density lipoprotein receptor protein by proprotein convertase subtilisin/kexin type 9a in mouse liver. J. Biol. Chem. 279, 50630-50638.

Pena, F., Jansens, A., van Zadelhoff, G., and Braakman, I. (2010). Calcium as a crucial cofactor for low density lipoprotein receptor folding in the endoplasmic reticulum. J. Biol. Chem. 285, 8656-8664.

Poirier, S., and Mayer, G. (2013). The biology of PCSK9 from the endoplasmic reticulum to lysosomes: new and emerging therapeutics to control low-density lipoprotein cholesterol. Drug design, development and therapy 7, 1135-1148.

Poirier, S., Mayer, G., Benjannet, S., Bergeron, E., Marcinkiewicz, J., Nassoury, N., Mayer, H., Nimpf, J., Prat, A., and Seidah, N. G. (2008). The proprotein convertase PCSK9 induces the degradation of low density lipoprotein receptor (LDLR) and its closest family members VLDLR and ApoER2. J. Biol. Chem. 283, 2363-2372.

Poirier, S., Mayer, G., Poupon, V., McPherson, P. S., Desjardins, R., Ly, K., Asselin, M. C., Day, R., Duclos, F. J., Witmer, M., et al. (2009). Dissection of the endogenous cellular pathways of PCSK9-induced low density lipoprotein receptor degradation: evidence for an intracellular route. J. Biol. Chem. 284, 28856-28864.

Poirier, S., Samami, S., Mamarbachi, M., Demers, A., Chang, T. Y., Vance, D. E., Hatch, G. M., and Mayer, G. (2014). The epigenetic drug 5-azacytidine interferes with cholesterol and lipid metabolism. J. Biol. Chem. 289, 18736-18751.

Rader, D. J., Cohen, J., and Hobbs, H. H. (2003). Monogenic hypercholesterolemia: new insights in pathogenesis and treatment. J. Clin. Invest. 111, 1795-1803.

Rashid, S., Curtis, D. E., Garuti, R., Anderson, N. N., Bashmakov, Y., Ho, Y. K., Hammer, R. E., Moon, Y. A., and Horton, J. D. (2005). Decreased plasma cholesterol and hypersensitivity to statins in mice lacking Pcsk9. Proc. Natl. Acad. Sci. U.S.A. 102, 5374-5379.

Sabatine M S, Giugliano R P, Wiviott S D, et al. Efficacy and safety of evolocumab in reducing lipids and cardiovascular events. *N Engl J Med.* 2015; 372(16):1500-1509.

Seidah, N. G., Benjannet, S., Wickham, L., Marcinkiewicz, J., Jasmin, S. B., Stifani, S., Basak, A., Prat, A., and Chretien, M. (2003). The secretory proprotein convertase neural apoptosis-regulated convertase 1 (NARC-1): liver regeneration and neuronal differentiation. Proc. Natl. Acad. Sci. U.S.A. 100, 928-933.

Stebbins, C. E., Russo, A. A., Schneider, C., Rosen, N., Hartl, F. U., and Pavletich, N. P. (1997). Crystal structure of an Hsp90-geldanamycin complex: targeting of a protein chaperone by an antitumor agent. Cell 89, 239-250.

Walley, K. R., Thain, K. R., Russell, J. A., Reilly, M. P., Meyer, N.J., Ferguson, J. F., Christie, J. D., Nakada, T. A., Fjell, C. D., Thair, S. A., et al. (2014). PCSK9 is a critical regulator of the innate immune response and septic shock outcome. Science translational medicine 6, 258ra143.

Wang, Y., Huang, Y., Hobbs, H. H., and Cohen, J. C. (2012). Molecular characterization of proprotein convertase subtilisin/kexin type 9-mediated degradation of the LDLR. J. Lipid Res. 53, 1932-1943.

Weekes, M. P., Antrobus, R., Talbot, S., Hor, S., Simecek, N., Smith, D. L., Bloor, S., Randow, F., and Lehner, P. J. (2012). Proteomic plasma membrane profiling reveals an essential role for gp96 in the cell surface expression of LDLR family members, including the LDL receptor and LRP6. J Proteome Res 11, 1475-1484.

Wenner Moyer, M. The search beyond statins. Nat. Med. 16, 150-153.

Wu, S., Hong, F., Gewirth, D., Guo, B., Liu, B., and Li, Z. (2012). The molecular chaperone gp96/GRP94 interacts with Toll-like receptors and integrins via its C-terminal hydrophobic domain. J. Biol. Chem. 287, 6735-6742.

Yamamoto, T., Lu, C., and Ryan, R. O. (2011). A two-step binding model of PCSK9 interaction with the low density lipoprotein receptor. J. Biol. Chem. 286, 5464-5470.

Yusuf, S., Hawken, S., Ounpuu, S., Dans, T., Avezum, A., Lanas, F., McQueen, M., Budaj, A., Pais, P., Varigos, J., et al. (2004). Effect of potentially modifiable risk factors associated with myocardial infarction in 52 countries (the INTERHEART study): case-control study. Lancet 364, 937-952.

Zaid, A., Roubtsova, A., Essalmani, R., Marcinkiewicz, J., Chamberland, A., Hamelin, J., Tremblay, M., Jacques, H., Jin, W., Davignon, J., et al. (2008). Proprotein convertase subtilisin/kexin type 9 (PCSK9): hepatocyte-specific low-density lipoprotein receptor degradation and critical role in mouse liver regeneration. Hepatology 48, 646-654.

Zhang, D. W., Garuti, R., Tang, W. J., Cohen, J. C., and Hobbs, H. H. (2008). Structural requirements for PCSK9-mediated degradation of the low-density lipoprotein receptor. Proc. Natl. Acad. Sci. U.S.A. 105, 13045-13050.

Zhang, D. W., Lagace, T. A., Garuti, R., Zhao, Z., McDonald, M., Horton, J. D., Cohen, J. C., and Hobbs, H. H. (2007). Binding of proprotein convertase subtilisin/kexin type 9 to epidermal growth factor-like repeat A of low density lipoprotein receptor decreases receptor recycling and increases degradation. J. Biol. Chem. 282, 18602-18612.

Zhao, Z., Tuakli-Wosornu, Y., Lagace, T. A., Kinch, L., Grishin, N. V., Horton, J. D., Cohen, J. C., and Hobbs, H. H. (2006). Molecular characterization of loss-of-function mutations in PCSK9 and identification of a compound heterozygote. Am. J. Hum. Genet. 79, 514-523.

The invention claimed is:

1. A method of reducing circulating LDL-cholesterol levels in a subject in need thereof, the method comprising administering to the subject a therapeutically effective amount of a conjugated polypeptide comprising the amino acid sequence of SEQ. ID. NO. 4, wherein the conjugated polypeptide is conjugated to one or more polymer moieties, and wherein the conjugated polypeptide binds to PSCK9.

2. The method according to claim 1, wherein the polypeptide consists of SEQ. ID. NO. 4.

3. The method according to claim 1, wherein the polypeptide is conjugated to NH2- group at its C-terminus.

4. The method according to claim 1, wherein the polypeptide is conjugated to CH3-CO— group at its N-terminus.

5. The method according to claim 1, wherein the polypeptide is conjugated to an N terminal blocking group selected from a N-acetyl amino acid, a glycosylated amino acid, a pyrrolidone carboxylate group, an acetylated amino acid, a formylated amino acid, myristic acid, and pyroglutamate.

6. The method according to claim 1 wherein said polymer moiety is conjugated to at least one of the N-terminus, the C-terminus, a lysine side chain, and an arginine side chain.

7. The method according to claim 1 wherein said polymer moiety is conjugated by means of at least one of an amine bond, a hydroxy succinimide bond, and an aldehyde bond.

8. The method according to claim 1 wherein said polymer moiety has a molecular weight between 0.6 and 5.0 kDa.

9. The method according to claim 1 wherein said polymer moiety is polyethylene glycol.

10. The method according to claim 1, wherein said pharmaceutically effective amount is between 0.0001 to 1.0 milligrams per kilogram.

11. The method according to claim 1, wherein the polypeptide is between 27 and 169 amino acids in length.

12. The method according to claim 1, wherein the subject has hyperlipidemia.

13. The method according to claim 1, wherein the conjugated polypeptide is a competitive inhibitor of proprotein convertase subtilisin/kexin type 9 (PCSK9) binding to low-density lipoprotein receptors (LDLR).

* * * * *